(12) United States Patent
Kaku et al.

(10) Patent No.: US 8,030,547 B2
(45) Date of Patent: Oct. 4, 2011

(54) GENE CODING FOR ACETOLACTATE SYNTHASE

(75) Inventors: Koichiro Kaku, Shizuoka (JP); Tsutomu Shimizu, Shizuoka (JP); Kiyoshi Kawai, Shizuoka (JP); Kozo Nagayama, Shizuoka (JP); Atsunori Fukuda, Ibaraki (JP); Yoshiyuki Tanaka, Ibaraki (JP)

(73) Assignees: Kumiai Chemical Industry Co., Ltd., Tokyo (JP); National Institute of Agrobiolgical Sciences, Tsukuba-Shi (JP)

( * ) Notice: Subject to any disclaimer, the term of this patent is extended or adjusted under 35 U.S.C. 154(b) by 643 days.

(21) Appl. No.: 12/053,101

(22) Filed: Mar. 21, 2008

(65) Prior Publication Data

US 2009/0300803 A1 Dec. 3, 2009

Related U.S. Application Data

(62) Division of application No. 10/509,121, filed as application No. PCT/JP03/01917 on Feb. 21, 2003, now abandoned.

(30) Foreign Application Priority Data

Mar. 29, 2002 (JP) ................................ 2002-095721

(51) Int. Cl.
*C12N 15/29* (2006.01)
*C12N 15/82* (2006.01)

(52) U.S. Cl. ..................... 800/300; 435/320.1; 536/23.2; 800/278

(58) Field of Classification Search .......................... None
See application file for complete search history.

(56) References Cited

U.S. PATENT DOCUMENTS 7,119,256 B2 * 10/2006 Shimizu et al. ............... 800/300

FOREIGN PATENT DOCUMENTS

| WO | WO-00/27182 A1 | 5/2000 |
|---|---|---|
| WO | WO 01/58970 | 8/2001 |
| WO | WO 01/85970 A2 * | 11/2001 |
| WO | WO-01/85970 A2 | 11/2001 |
| WO | WO-02/44385 A1 | 6/2002 |

OTHER PUBLICATIONS

Wright et al 1998, Weed Science 46: 13-23.*
Webster et al 2001 Weed Science 49: 652-657.*
Bernasconi, P. et al., "A Naturally Occurring Point Mutatioin Confers Broad Range Tolerance to Herbicides That Target Acetolactate Synthase", J. Biol. Chem. (1995), vol. 270, No. 29, pp. 17381 to 17385.
Mourad, G. et al., "Intragenic Recomination in the CSR1 Locus of *Arabidopsis*", Mol. Gen. Genet. (1994), vol. 243, No. 2, pp. 178 to 184.
David Chipman et al., "Biosynthesis of 2-Aceto-2-Hydroxy Acids: Acetolactate Synthases and Acetohydroxyacid Synthases", Biochem.Biophys.Acta (1998), vol. 1385, pp. 401 to 419.
Chong, C.K. et al., "Role of Tryptophanyl Residues in Tobacco Acetolactate Synthase", Biochem. Biophys.Res.Commun. (1999), vol. 259, No. 1, pp. 136 to 140.
Chong, C.K. et al., "Amino Acid Residues Conferring Herbicide Tolerance in Tobacco Acetolactate Synthase", Biochem.Biophys. Res.Commun. (2000), vol. 279, No. 2, pp. 462 to 467.
Kathleen Y. Lee et al., "The Molecular Basis of Sulfonylurea Herbicide Resistance in Tobacco", The EMBO J. (1988), vol. 7, No. 5, pp. 1241 to 1248.
K.-H. Ott et al, *J. Mol. Biol.* (1996) 263,359-368.
Kaku et al., The Pesticide Science Society of Japan, 2002 Annual Meeting, A summary of lectures, lectures, pp. 1-2.
Eberlein et al., Weed Science, vol. 45, pp. 212-217 (1997).
Korean Notice of Allowance mailed Feb. 16, 2010 in Application No. 10-2004-7015479.

* cited by examiner

*Primary Examiner* — David H Kruse
(74) *Attorney, Agent, or Firm* — Birch, Stewart, Kolasch & Birch, LLP

(57) ABSTRACT

Disclosed is a gene coding for a protein (a) or (b) showing a high level of resistance to PC herbicides or sulfonylurea herbicides. The protein (a) consists of an amino acid sequence of any one of SEQ ID NOS: 2, 4, 6 and 8, and the protein (b) consists of an amino acid sequence derived from the amino acid sequence of any one of SEQ ID NOS: 2, 4, 6 and 8 by substitution, deletion or addition of at least one or more amino acids, has resistance to a pyrimidinyl carboxy herbicide, and has acetolactate synthase activity.

6 Claims, 34 Drawing Sheets

Fig. 1A

```
Wild          1 MATTAAAAAAALSAAATAKTGRKNHQRHHVLPARGRVGAAAVRCSAVSPVTPPSPAPPAT   60
P/R Mutant    1 MATTAAAAAAALSAAATAKTGRKNHQRHHVLPARGRVGAAAVRCSAVSPVTPPSPAPPAT   60
P/W Mutant    1 MATTAAAAAAALSAAATAKTGRKNHQRHHVLPARGRVGAAAVRCSAVSPVTPPSPAPPAT   60
P/S Mutant    1 MATTAAAAAAALSAAATAKTGRKNHQRHHVLPARGRVGAAAVRCSAVSPVTPPSPAPPAT   60
P/S/W Mutant  1 MATTAAAAAAALSAAATAKTGRKNHQRHHVLPARGRVGAAAVRCSAVSPVTPPSPAPPAT   60
                ************************************************************

Wild         61 PLRPWGPAEPRKGADILVEALERCGVSDVFAYPGGASMEIHQALTRSPVITNHLFRHEQG  120
P/R Mutant   61 PLRPWGPAEPRKGADILVEALERCGVSDVFAYPGGASMEIHQALTRSPVITNHLFRHEQG  120
P/W Mutant   61 PLRPWGPAEPRKGADILVEALERCGVSDVFAYPGGASMEIHQALTRSPVITNHLFRHEQG  120
P/S Mutant   61 PLRPWGPAEPRKGADILVEALERCGVSDVFAYPGGASMEIHQALTRSPVITNHLFRHEQG  120
P/S/W Mutant 61 PLRPWGPAEPRKGADILVEALERCGVSDVFAYPGGASMEIHQALTRSPVITNHLFRHEQG  120
                ************************************************************

Wild        121 EAFAASGYARASGRVGVCVATSGPGATNLVSALADALLDSVPMVAITGGVPRRMIGTDAF  180
P/R Mutant  121 EAFAASGYARASGRVGVCVATSGPGATNLVSALADALLDSVPMVAITGGVHSRMIGTDAF  180
P/W Mutant  121 EAFAASGYARASGRVGVCVATSGPGATNLVSALADALLDSVPMVAITGGVHRRMIGTDAF  180
P/S Mutant  121 EAFAASGYARASGRVGVCVATSGPGATNLVSALADALLDSVPMVAITGGVHRRMIGTDAF  180
P/S/W Mutant 121 EAFAASGYARASGRVGVCVATSGPGATNLVSALADALLDSVPMVAITGGVHRRMIGTDAF  180
                ***********************************************  *********

Wild        181 QETPIVEVTRSITKHNYLVLDVEDIPRVIQEAFFLASSGRPGPVLVDIPKDIQQMAVPV   240
P/R Mutant  181 QETPIVEVTRSITKHNYLVLDVEDIPRVIQEAFFLASSGRPGPVLVDIPKDIQQMAVPV   240
P/W Mutant  181 QETPIVEVTRSITKHNYLVLDVEDIPRVIQEAFFLASSGRPGPVLVDIPKDIQQMAVPV   240
P/S Mutant  181 QETPIVEVTRSITKHNYLVLDVEDIPRVIQEAFFLASSGRPGPVLVDIPKDIQQMAVPV   240
P/S/W Mutant 181 QETPIVEVTRSITKHNYLVLDVEDIPRVIQEAFFLASSGRPGPVLVDIPKDIQQMAVPV   240
                ************************************************************

Wild        241 WDTSMNLPGYIARLPKPPATELLEQVLRLVGESRRPILYVGGGCSASGDELRWFVELTGI  300
P/R Mutant  241 WDTSMNLPGYIARLPKPPATELLEQVLRLVGESRRPILYVGGGCSASGDELRWFVELTGI  300
P/W Mutant  241 WDTSMNLPGYIARLPKPPATELLEQVLRLVGESRRPILYVGGGCSASGDELRWFVELTGI  300
P/S Mutant  241 WDTSMNLPGYIARLPKPPATELLEQVLRLVGESRRPILYVGGGCSASGDELRWFVELTGI  300
P/S/W Mutant 241 WDTSMNLPGYIARLPKPPATELLEQVLRLVGESRRPILYVGGGCSASGDELRWFVELTGI  300
                ************************************************************

Wild        301 PVTTTLMGLGNFPSDDPLSLRMLGMHGTVYANYAVDKADLLLAFGVRFDDRVTGKIEAFA  360
P/R Mutant  301 PVTTTLMGLGNFPSDDPLSLRMLGMHGTVYANYAVDKADLLLAFGVRFDDRVTGKIEAFA  360
P/W Mutant  301 PVTTTLMGLGNFPSDDPLSLRMLGMHGTVYANYAVDKADLLLAFGVRFDDRVTGKIEAFA  360
P/S Mutant  301 PVTTTLMGLGNFPSDDPLSLRMLGMHGTVYANYAVDKADLLLAFGVRFDDRVTGKIEAFA  360
P/S/W Mutant 301 PVTTTLMGLGNFPSDDPLSLRMLGMHGTVYANYAVDKADLLLAFGVRFDDRVTGKIEAFA  360
                ************************************************************

Wild        361 SRAKIVHIDIDPAEIGKNKQPHVSICADVKLALQGLNALLQQSTTKTSSDFSAWHNELDQ  420
P/R Mutant  361 SRAKIVHIDIDPAEIGKNKQPHVSICADVKLALQGLNALLQQSTTKTSSDFSAWHNELDQ  420
P/W Mutant  361 SRAKIVHIDIDPAEIGKNKQPHVSICADVKLALQGLNALLQQSTTKTSSDFSAWHNELDQ  420
P/S Mutant  361 SRAKIVHIDIDPAEIGKNKQPHVSICADVKLALQGLNALLQQSTTKTSSDFSAWHNELDQ  420
P/S/W Mutant 361 SRAKIVHIDIDPAEIGKNKQPHVSICADVKLALQGLNALLQQSTTKTSSDFSAWHNELDQ  420
                ************************************************************

Wild        421 QKREFPLGYKTFGEEIPPQYAIQVLDELTKGEAIIATGVGQHQMWAAQYYTYKRPRQWLS  480
P/R Mutant  421 QKREFPLGYKTFGEEIPPQYAIQVLDELTKGEAIIATGVGQHQMWAAQYYTYKRPRQWLS  480
P/W Mutant  421 QKREFPLGYKTFGEEIPPQYAIQVLDELTKGEAIIATGVGQHQMWAAQYYTYKRPRQWLS  480
P/S Mutant  421 QKREFPLGYKTFGEEIPPQYAIQVLDELTKGEAIIATGVGQHQMWAAQYYTYKRPRQWLS  480
P/S/W Mutant 421 QKREFPLGYKTFGEEIPPQYAIQVLDELTKGEAIIATGVGQHQMWAAQYYTYKRPRQWLS  480
                ************************************************************

Wild        481 SAGLGAMGFGLPAAAGASVANPGVTVVDIDGDGSFLMNIQELALIRIENLPVKVMVLNNQ  540
P/R Mutant  481 SAGLGAMGFGLPAAAGASVANPGVTVVDIDGDGSFLMNIQELALIRIENLPVKVMVLNNQ  540
P/W Mutant  481 SAGLGAMGFGLPAAAGASVANPGVTVVDIDGDGSFLMNIQELALIRIENLPVKVMVLNNQ  540
```

Fig. 1 B

```
P/S Mutant    481 SAGLGAMGFGLPAAAGASVANPGVTVVDIDGDGSFLMNIQELALIRIENLPVKVMVLNNQ    540
P/S/W Mutant  481 SAGLGAMGFGLPAAAGASVANPGVTVVDIDGDGSFLMNIQELALIRIENLPVKVMVLNNQ    540
                  ************************************************************

Wild          541 HLGMVVQWEDRFYKANRAHTYLGNPECESEIYPDFVTIAKGFNIPAVRVTKKSEVRAAIK    600
P/R Mutant    541 HLGMVVQWEDRFYKANRAHTYLGNPECESEIYPDFVTIAKGFNIPAVRVTKKSEVRAAIK    600
P/W Mutant    541 HLGMVVQLEDRFYKANRAHTYLGNPECESEIYPDFVTIAKGFNIPAVRVTKKSEVRAAIK    600
P/S Mutant    541 HLGMVVQWEDRFYKANRAHTYLGNPECESEIYPDFVTIAKGFNIPAVRVTKKSEVRAAIK    600
P/S/W Mutant  541 HLGMVVQLEDRFYKANRAHTYLGNPECESEIYPDFVTIAKGFNIPAVRVTKKSEVRAAIK    600
                  *******·****************************************************

Wild          601 KMLETPGPYLLDIIVPHQEHVLPMIPSGGAFKDMILDGDGRTVY    644
P/R Mutant    601 KMLETPGPYLLDIIVPHQEHVLPMIPSGGAFKDMILDGDGRTVY    644
P/W Mutant    601 KMLETPGPYLLDIIVPHQEHVLPMIPSGGAFKDMILDGDGRTVY    644
P/S Mutant    601 KMLETPGPYLLDIIVPHQEHVLPMIPIGGAFKDMILDGDGRTVY    644
P/S/W Mutant  601 KMLETPGPYLLDIIVPHQEHVLPMIPIGGAFKDMILDGDGRTVY    644
                  *************************·*****************
```

Fig. 2 A

| | | | |
|---|---|---|---|
| Wild | 1 | CCCAAACCCAGAAACCCTCGCCGCCGCCGCCGCCGCCACCACCCACCATGGCTACGACCG | 60 |
| P/R Mutation | 1 | CCCAAACCCAGAAACCCTCGCCGCCGCCGCCGCCGCCACCACCCACCATGGCTACGACCG | 60 |
| P/W Mutation | 1 | CCCAAACCCAGAAACCCTCGCCGCCGCCGCCGCCGCCACCACCCACCATGGCTACGACCG | 60 |
| P/S Mutation | 1 | CCCAAACCCAGAAACCCTCGCCGCCGCCGCCGCCGCCACCACCCACCATGGCTACGACCG | 60 |
| P/W/S Mutation | 1 | CCCAAACCCAGAAACCCTCGCCGCCGCCGCCGCCGCCACCACCCACCATGGCTACGACCG | 60 |
| | | ************************************************************ | |
| Wild | 61 | CCGCGGCCGCGGCCGCCGCCCTGTCCGCCGGCCGCGACGGCCAAGACCGGCCGTAAGAACC | 120 |
| P/R Mutation | 61 | CCGCGGCCGCGGCCGCCGCCCTGTCCGCCGGCCGCGACGGCCAAGACCGGCCGTAAGAACC | 120 |
| P/W Mutation | 61 | CCGCGGCCGCGGCCGCCGCCCTGTCCGCCGGCCGCGACGGCCAAGACCGGCCGTAAGAACC | 120 |
| P/S Mutation | 61 | CCGCGGCCGCGGCCGCCGCCCTGTCCGCCGGCCGCGACGGCCAAGACCGGCCGTAAGAACC | 120 |
| P/W/S Mutation | 61 | CCGCGGCCGCGGCCGCCGCCCTGTCCGCCGGCCGCGACGGCCAAGACCGGCCGTAAGAACC | 120 |
| | | ************************************************************ | |
| Wild | 121 | ACCAGCGACACCACGTCCTTCCCGCTCGAGGCCGGGTGGGGGCGGCGGCGGTCAGGTGCT | 180 |
| P/R Mutation | 121 | ACCAGCGACACCACGTCCTTCCCGCTCGAGGCCGGGTGGGGGCGGCGGCGGTCAGGTGCT | 180 |
| P/W Mutation | 121 | ACCAGCGACACCACGTCCTTCCCGCTCGAGGCCGGGTGGGGGCGGCGGCGGTCAGGTGCT | 180 |
| P/S Mutation | 121 | ACCAGCGACACCACGTCCTTCCCGCTCGAGGCCGGGTGGGGGCGGCGGCGGTCAGGTGCT | 180 |
| P/W/S Mutation | 121 | ACCAGCGACACCACGTCCTTCCCGCTCGAGGCCGGGTGGGGGCGGCGGCGGTCAGGTGCT | 180 |
| | | ************************************************************ | |
| Wild | 181 | CGGCGGTGTCCCCGGTCACCCGGCGGTGCCCGGCGGCGCCGGCCACGCGCTCCGGCCGT | 240 |
| P/R Mutation | 181 | CGGCGGTGTCCCCGGTCACCCGGCGGTGCCCGGCGGCGCCGGCCACGCGCTCCGGCCGT | 240 |
| P/W Mutation | 181 | CGGCGGTGTCCCCGGTCACCCGGCGGTGCCCGGCGGCGCCGGCCACGCGCTCCGGCCGT | 240 |
| P/S Mutation | 181 | CGGCGGTGTCCCCGGTCACCCGGCGGT CCCGGCGGCGCCGGCCACGCGCTCCGGCCGT | 240 |
| P/W/S Mutation | 181 | CGGCGGTGTCCCCGGTCACCCGGCCG CCCGGCGCCGCCGGCCACGCGCTCCGGCCGT | 240 |
| | | ************************************************************ | |
| Wild | 241 | GGGGGCCGGCCGAGCCCCGCAAGGGCGCGGACATCCTCGTGGAGGCGCTGGAGCGGTGCG | 300 |
| P/R Mutation | 241 | GGGGGCCGGCCGAGCCCCGCAAGGGCGCGGACATCCTCGTGGAGGCGCTGGAGCGGTGCG | 300 |
| P/W Mutation | 241 | GGGGGCCGGCCGAGCCCCGCAAGGGCGCGGACATCCTCGTGGAGGCGCTGGAGCGGTGCG | 300 |
| P/S Mutation | 241 | GGGGGCCGGCCGAGCCCCGCAAGGGCGCGGACATCCTCGT GGAGGCGCTGGAGCGGTGCG | 300 |
| P/W/S Mutation | 241 | GGGGGCCGGCCGAGCCCCGCAAGGGCGCGGACATCCTCGTGGAGGCGCTGGAGCGGTGCG | 300 |
| | | ************************************************************ | |
| Wild | 301 | GCGTCAGCGACGTCTTCGCCTACCCGGGCGGCGCGTCCATGGAGATCCACCAGGCGCTGA | 360 |
| P/R Mutation | 301 | GCGTCAGCGACGTGTTCGCCTACCCGGGCGGCGCGTCCATGGAGATCCACCAGGCGCTGA | 360 |
| P/W Mutation | 301 | GCGTCAGCGACGTGTTCGCCTACCCGGGCGGCGCGTCCATGGAGATCCACCAGGCGCTGA | 360 |
| P/S Mutation | 301 | GCGTCAGCGACGTGTTCGCCTACCCGGGCGGCGCGTCCATGGAGATCCACCAGGCGCTGA | 360 |
| P/W/S Mutation | 301 | GCGTCAGCGACGTGTTCGCCTACCCGGGCGGCGCGTCCATGGAGATCCACCAGGCGCTGA | 360 |
| | | ************************************************************ | |
| Wild | 361 | CGCGCTCCCCGGTCATCACCAACCACCTCTTCCGCCACGAGCAGGGCGAGGCGTTCGCGG | 420 |
| P/R Mutation | 361 | CGCGCTCCCCGGTCATCACCAACCACCTCTTCCGCCACGAGCAGGGCGAGGCGTTCGCGG | 420 |
| P/W Mutation | 361 | CGCGCTCCCCGGTCATCACCAACCACCTCTTCCGCCACGAGCAGGGCGAGGCGTTCGCGG | 420 |
| P/S Mutation | 361 | CGCGCTCCCCGGTCATCACCAACCACCTCTTCCGCCACGAGCAGGGCGAGGCGTTCGCGG | 420 |
| P/W/S Mutation | 361 | CGCGCTCCCCGGTCATCACCAACCACCTCTTCCGCCACGAGCAGGGCGAGGCCTTCGCGG | 420 |
| | | ************************************************************ | |
| Wild | 421 | CGTCCGGGTACGCGCGCGCGTCCGGCCGCGTCGGGGTCTGCGTCGCCACCTCCGGCCCCG | 480 |
| P/R Mutation | 421 | CGTCCGGGTACGCGCGCGCGTCCGGCCGCGTCGGGGTCTGCGTCGCCACCTCCGGCCCCG | 480 |
| P/W Mutation | 421 | CGTCCGGGTACGCGCGCGCGTCCGGCCGCGTCGGGGTCTGCGTCGCCACCTCCGGCCCCG | 480 |
| P/S Mutation | 421 | CGTCCGGGTACGCGCGCGCGTCCGGCCGCGTCGGGGTCTGCGTCGCCACCTCCGGCCCCG | 480 |
| P/W/S Mutation | 421 | CGTCCGGGTACGCGCGCGCGTCCGGCCGCGTCGGGGTCTGCGTCGCCACCTCCGGCCCCG | 480 |
| | | ************************************************************ | |
| Wild | 481 | GGGCAACCAACCTCGTGTCCGCGCTCGCCGACGCGCTGCTCGACTCCGTCCCGATGGTCG | 540 |
| P/R Mutation | 481 | GGGCAACCAACCTCGTGTCCGCGCTCGCCGACGCGCTGCTCGACTCCGTCCCGATGGTCG | 540 |
| P/W Mutation | 481 | GGGCAACCAACCTCGTGTCCGCGCTCGCCGACGCGCTGCTCGACTCCGTCCCGATGGTCG | 540 |
| P/S Mutation | 481 | GGGCAACCAACCTCGTGTCCGCGCTCGCCGACGCGGTGCTCGACTCCGTCCCGATGGTCG | 540 |
| P/W/S Mutation | 481 | GGGCAACCAACCTCGTGTCCGCGCTCGCCGACGCGGTGCTCGACTCCGTCCCGATGGTCG | 540 |
| | | ************************************************************ | |
| Wild | 541 | CCATCACGGGCCAGGTCCCCCGCCGCATGATCGGCACCGACGCCTTCCAGGAGACGCCCA | 600 |
| P/R Mutation | 541 | CCATCACGGGCCAGGTCCACAGCCGCATGATCGGCACCGACGCCTTCCAGGAGACGCCCA | 600 |
| P/W Mutation | 541 | CCATCACGGGCCAGGTCCACCGCCGCATGATCGGCACCGACGCCTTCCAGGAGACGCCCA | 600 |
| P/S Mutation | 541 | CCATCACGGGCCAGGTCCACCGCCGCATGATCGGCACCGACGCCTTCCAGGAGACGCCCA | 600 |
| P/W/S Mutation | 541 | CCATCACGGGCCAGGTCCACCGCCGCATGATCGGCACCGACGCCTTCCAGGAGACGCCCA | 600 |
| | | ************* * ************************************** | |
| Wild | 601 | TAGTCGAGGTCACCCGCTCCATCACCAAGCACAATTACCTTGTCCTTGATGTGGAGGACA | 660 |
| P/R Mutation | 601 | TAGTCGAGGTCACCCGCTCCATCACCAAGCACAATTACCTTGTCCTTGATGTGGAGGACA | 660 |
| P/W Mutation | 601 | TAGTCGAGGTCACCCGCTCCATCACCAAGCACAATTACCTTGTCCTTGATGTGGAGGACA | 660 |

Fig. 2 B

```
P/S Mutation    601 TAGTCGAGGTCACCCGCTCCATCACCAAGCACAATTACCTTGTCCTTGATGTGGAGGACA 660
P/W/S Mutation  601 TAGTCGAGGTCACCCGCTCCATCACCAAGCACAATTACCTTGTCCTTGATGTGGAGGACA 660
                    ************************************************************

Wild            661 TCCCCCGCGTCATACAGGAAGCCTTCTTCCTCGCGTCCTCGGGCCGTCCTGGCCCGGTGC 720
P/R Mutation    661 TCCCCCGCGTCATACAGGAAGCCTTCTTCCTCGCGTCCTCGGGCCGTCCTGGCCCGGTGC 720
P/W Mutation    661 TCCCCCGCGTCATACAGGAAGCCTTCTTCCTCGCGTCCTCGGGCCGTCCTGGCCCGGTGC 720
P/S Mutation    661 TCCCCCGCGTCATACAGGAAGCCTTCTTCCTCGCGTCCTCGGGCCGTCCTGGCCCGGTGC 720
P/W/S Mutation  661 TCCCCCGCGTCATACAGGAAGCCTTCTTCCTCGCGTCCTCGGGCCGTCCTGGCCCGGTGC 720
                    ************************************************************

Wild            721 TGGTCGACATCCCCAAGGACATCCAGCAGCAGATGGCCGTGCCGGTCTGGGACACCTCGA 780
P/R Mutation    721 TGGTCGACATCCCCAAGGACATCCAGCAGCAGATGGCCGTGCCGGTCTGGGACACCTCGA 780
P/W Mutation    721 TGGTCGACATCCCCAAGGACATCCAGCAGCAGATGGCCGTGCCGGTCTGGGACACCTCGA 780
P/S Mutation    721 TGGTCGACATCCCCAAGGACATCCAGCAGCAGATGGCCGTGCCGGTCTGGGACACCTCGA 780
P/W/S Mutation  721 TGGTCGACATCCCCAAGGACATCCAGCAGCAGATGGCCGTGCCGGTCTGGGACACCTCGA 780
                    ************************************************************

Wild            781 TGAATCTACCAGGGTACATCGCACGCCTGCCCAAGCCACCCGCGACAGAATTGCTTGAGC 840
P/R Mutation    781 TGAATCTACCAGGGTACATCGCACGCCTGCCCAAGCCACCGCGGACAGAATTGCTTGAGC 840
P/W Mutation    781 TGAATCTACCAGGGTACATCGCACGCCTGCCCAAGCCACCCGCGACAGAATTGCTTGAGC 840
P/S Mutation    781 TGAATCTACCAGGGTACATCGCACGCCTGCCCAAGCCACCCGCGACAGAATTGCTTGAGC 840
P/W/S Mutation  781 TGAATCTACCAGGGTACATCGCACGCCTGCCCAAGCCACCCGCGACAGAATTGCTTGAGC 840
                    ************************************************************

Wild            841 AGGTCTTGCGTCTGGTTGGCGAGTCACGGCGCCCGATTCTCTATGTCGGTGGTGGCTGCT 900
P/R Mutation    841 AGGTCTTGCGTCTGGTTGGCGAGTCACGGCGCCCGATTCTCTATGTCGGTGGTGGCTGCT 900
P/W Mutation    841 AGGTCTTGCGTCTGGTTGGCGAGTCACGGCGCCCGATTCTCTATGTCGGTGGTGGCTGCT 900
P/S Mutation    841 AGGTCTTGCGTCTGGTTGGCGAGTCACGGCGCCCGATTCTCTATGTCGGTGGTGGCTGCT 900
P/W/S Mutation  841 AGGTCTTGCGTCTGGTTGGCGAGTCACGGCGCCCGATTCTCTATGTCGGTGGTGGCTGCT 900
                    ************************************************************

Wild            901 CTGCATCTGGTGACGAATTGCGCTGGTTTGTTGAGCTGACTGGTATCCCAGTTACAACCA 960
P/R Mutation    901 CTGCATCTGGTGACGAATTGCGCTGGTTTGTTGAGCTGACTGGTATCCCAGTTACAACCA 960
P/W Mutation    901 CTGCATCTGGTGACGAATTGCGCTGGTTTGTTGAGCTGACTGGTATCCCAGTTACAACCA 960
P/S Mutation    901 CTGCATCTGGTGACGAATTGCGCTGGTTTGTTGAGCTGACTGGTATCCCAGTTACAACCA 960
P/W/S Mutation  901 CTGCATCTGGTGACGAATTGCGCTGGTTTGTTGAGCTGACTGGTATCCCAGTTACAACCA 960
                    ************************************************************

Wild            961 CTCTGATGGGCCTCGGCAATTTCCCCAGTGACGACCCGTTGTCCCTGCGCATGCTTGGGA 1020
P/R Mutation    961 CTCTGATGGGCCTCGGCAATTTCCCCAGTGACGACCCGTTGTCCCTGCGCATGCTTGGGA 1020
P/W Mutation    961 CTCTGATGGGCCTCGGCAATTTCCCCAGTGACGACCCGTTGTCCCTGCGCATGCTTGGGA 1020
P/S Mutation    961 CTCTGATGGGCCTCGGCAATTTCCCCAGTGACGACCCGTTGTCCCTGCGCATGCTTGGGA 1020
P/W/S Mutation  961 CTCTGATGGGCCTCGGCAATTTCCCCAGTGACGACCCGTTGTCCCTGCGCATGCTTGGGA 1020
                    ************************************************************

Wild           1021 TGCATGGCACGGTGTACGCAAATTATGCCGTGGATAAGGCTGACCTGTTGCTTGCGTTTG 1080
P/R Mutation   1021 TGCATGGCACGGTGTACGCAAATTATGCCGTGGATAAGGCTGACCTGTTGCTTGCGTTTG 1080
P/W Mutation   1021 TGCATGGCACGGTGTACGCAAATTATGCCGTGGATAAGGCTGACCTGTTGCTTGCGTTTG 1080
P/S Mutation   1021 TGCATGGCACGGTGTACGCAAATTATGCCGTGGATAAGGCTGACCTGTTGCTTGCGTTTG 1080
P/W/S Mutation 1021 TGCATGGCACGGTGTACGCAAATTATGCCGTGGATAAGGCTGACCTGTTGCTTGCGTTTG 1080
                    ************************************************************

Wild           1081 GTGTGCGGTTTGATGATCGTGTGACAGGGAAAATTGAGGCTTTTGCAAGCAGGGCCAAGA 1140
P/R Mutation   1081 GTGTGCGGTTTGATGATCGTGTGACAGGGAAAATTGAGGCTTTTGCAAGCAGGGCCAAGA 1140
P/W Mutation   1081 GTGTGCGGTTTGATGATCGTGTGACAGGGAAAATTGAGGCTTTTGCAAGCAGGGCCAAGA 1140
P/S Mutation   1081 GTGTGCGGTTTGATGATCGTGTGACAGGGAAAATTGAGGCTTTTGCAAGCAGGGCCAAGA 1140
P/W/S Mutation 1081 GTGTGCGGTTTGATGATCGTGTGACAGGGAAAATTGAGGCTTTTGCAAGCAGGGCCAAGA 1140
                    ************************************************************

Wild           1141 TTGTGCACATTGACATTGATCCAGCAGAGATTGGAAAGAACAAGCAACCACATGTGTCAA 1200
P/R Mutation   1141 TTGTGCACATTGACATTGATCCAGCAGAGATTGGAAAGAACAAGCAACCACATGTGTCAA 1200
P/W Mutation   1141 TTGTGCACATTGACATTGATCCAGCAGAGATTGGAAAGAACAAGCAACCACATGTGTCAA 1200
P/S Mutation   1141 TTGTGCACATTGACATTGATCCAGCAGAGATTGGAAAGAACAAGCAACCACATGTGTCAA 1200
P/W/S Mutation 1141 TTGTGCACATTGACATTGATCCAGCAGAGATTGGAAAGAACAAGCAACCACATGTGTCAA 1200
                    ************************************************************

Wild           1201 TTTGCGCAGATGTTAAGCTTGCTTTACAGGGCTTGAATGCTCTGCTACAACAGAGCACAA 1260
P/R Mutation   1201 TTTGCGCAGATGTTAAGCTTGCTTTACAGGGCTTGAATGCTCTGCTACAACAGAGCACAA 1260
P/W Mutation   1201 TTTGCGCAGATGTTAAGCTTGCTTTACAGGGCTTGAATGCTCTGCTACAACAGAGCACAA 1260
P/S Mutation   1201 TTTGCGCAGATGTTAAGCTTGCTTTACAGGGCTTGAATGCTCTGCTACAACAGAGCACAA 1260
P/W/S Mutation 1201 TTTGCGCAGATGTTAAGCTTGCTTTACAGGGCTTGAATGCTCTGCTACAACAGAGCACAA 1260
                    ************************************************************

Wild           1261 CAAAGACAAGTTCTGATTTTAGTGCATGGCACAATGAGTTGGACCAGCAGAAGAGGGAGT 1320
P/R Mutation   1261 CAAAGACAAGTTCTGATTTTAGTGCATGGCACAATGAGTTGGACCAGCAGAAGAGGGAGT 1320
```

Fig. 2 C

```
P/W Mutation    1261 CAAAGACAAGTTCTGATTTTAGTGCATGGCACAATGAGTTGGACCAGCAGAAGAGGGAGT 1320
P/S Mutation    1261 CAAAGACAAGTTCTGATTTTAGTGCATGGCACAATGAGTTGGACCAGCAGAAGAGGGAGT 1320
P/W/S Mutation  1261 CAAAGACAAGTTCTGATTTTAGTGCATGGCACAATGAGTTGGACCAGCAGAAGAGGGAGT 1320
                     ************************************************************

Wild            1321 TTCCTCTGGGGTACAAAACTTTTGGTGAAGAGATCCCACCGCAATATGCCATTCAGGTGC 1380
P/R Mutation    1321 TTCCTCTGGGGTACAAAACTTTTGGTGAAGAGATCCCACCGCAATATGCCATTCAGGTGC 1380
P/W Mutation    1321 TTCCTCTGGGGTACAAAACTTTTGGTGAAGAGATCCCACCGCAATATGCCATTCAGGTGC 1380
P/S Mutation    1321 TTCCTCTGGGGTACAAAACTTTTGGTGAAGAGATCCCACCGCAATATGCCATTCAGGTGC 1380
P/W/S Mutation  1321 TTCCTCTGGGGTACAAAACTTTTGGTGAAGAGATCCCACCGCAATATGCCATTCAGGTGC 1380
                     ************************************************************

Wild            1381 TGGATGAGCTGACGAAAGGTGAGGCAATCATCGCTACTGGTGTTGGGCAGCACCAGATGT 1440
P/R Mutation    1381 TGGATGAGCTGACGAAAGGTGAGGCAATCATCGCTACTGGTGTTGGGCAGCACCAGATGT 1440
P/W Mutation    1381 TGGATGAGCTGACGAAAGGTGAGGCAATCATCGCTACTGGTGTTGGGCAGCACCAGATGT 1440
P/S Mutation    1381 TGGATGAGCTGACGAAAGGTGAGGCAATCATCGCTACTGGTGTTGGGCAGCACCAGATGT 1440
P/W/S Mutation  1381 TGGATGAGCTGACGAAAGGTGAGGCAATCATCGCTACTGGTGTTGGGCAGCACCAGATGT 1440
                     ************************************************************

Wild            1441 GGGCGGCACAATATTACACCTACAAGCGGCCACGGCAGTGGCTGTCTTCGGCTGGTCTGG 1500
P/R Mutation    1441 GGGCGGCACAATATTACACCTACAAGCGGCCACGGCAGTGGCTGTCTTCGGCTGGTCTGG 1500
P/W Mutation    1441 GGGCGGCACAATATTACACCTACAAGCGGCCACGGCAGTGGCTGTCTTCGGCTGGTCTGG 1500
P/S Mutation    1441 GGGCGGCACAATATTACACCTACAAGCGGCCACGGCAGTGGCTGTCTTCGGCTGGTCTGG 1500
P/W/S Mutation  1441 GGGCGGCACAATATTACACCTACAAGCGGCCACGGCAGTGGCTGTCTTCGGCTGGTCTGG 1500
                     ************************************************************

Wild            1501 GCGCAATGGGATTTGGGCTGCCTGCTGCAGCTGGTGCTTCTGTGGCTAACCCAGGTGTCA 1560
P/R Mutation    1501 GCGCAATGGGATTTGGGCTGCCTGCTGCAGCTGGTGCTTCTGTGGCTAACCCAGGTGTCA 1560
P/W Mutation    1501 GCGCAATGGGATTTGGGCTGCCTGCTGCAGCTGGTGCTTCTGTGGCTAACCCAGGTGTCA 1560
P/S Mutation    1501 GCGCAATGGGATTTGGGCTGCCTGCTGCAGCTGGTGCTTCTGTGGCTAACCCAGGTGTCA 1560
P/W/S Mutation  1501 GCGCAATGGGATTTGGGCTGCCTGCTGCAGCTGGTGCTTCTGTGGCTAACCCAGGTGTCA 1560
                     ************************************************************

Wild            1561 CAGTTGTTGATATTGATGGGGATGGTAGCTTCCTCATGAACATTCAGGAGCTGGCATTGA 1620
P/R Mutation    1561 CAGTTGTTGATATTGATGGGGATGGTAGCTTCCTCATGAACATTCAGGAGCTGGCATTGA 1620
P/W Mutation    1561 CAGTTGTTGATATTGATGGGGATGGTAGCTTCCTCATGAACATTCAGGAGCTGGCATTGA 1620
P/S Mutation    1561 CAGTTGTTGATATTGATGGGGATGGTAGCTTCCTCATGAACATTCAGGAGCTGGCATTGA 1620
P/W/S Mutation  1561 CAGTTGTTGATATTGATGGGGATGGTAGCTTCCTCATGAACATTCAGGAGCTGGCATTGA 1620
                     ************************************************************

Wild            1621 TCCGCATTGAGAACCTCCCTGTGAAGGTGATGGTGTTGAACAACCAACATTTGGGTATGG 1680
P/R Mutation    1621 TCCGCATTGAGAACCTCCCTGTGAAGGTGATGGTGTTGAACAACCAACATTTGGGTATGG 1680
P/W Mutation    1621 TCCGCATTGAGAACCTCCCTGTGAAGGTGATGGTGTTGAACAACCAACATTTGGGTATGG 1680
P/S Mutation    1621 TCCGCATTGAGAACCTCCCTGTGAAGGTGATGGTGTTGAACAACCAACATTTGGGTATGG 1680
P/W/S Mutation  1621 TCCGCATTGAGAACCTCCCTGTGAAGGTGATGGTGTTGAACAACCAACATTTGGGTATGG 1680
                     ************************************************************

Wild            1681 TGGTGCAATGGGAGGATAGGTTTTACAAGGCGAATAGGGCGCATACATACTTGGGCAACC 1740
P/R Mutation    1681 TGGTGCAATGGGAGGATAGGTTTTACAAGGCGAATAGGGCGCATACATACTTGGGCAACC 1740
P/W Mutation    1681 TGGTGCAATTGGAGGATAGGTTTTACAAGGCGAATAGGGCGCATACATACTTGGGCAACC 1740
P/S Mutation    1681 TGGTGCAATGGGAGGATAGGTTTTACAAGGCGAATAGGGCGCATACATACTTGGGCAACC 1740
P/W/S Mutation  1681 TGGTGCAATTGGAGGATAGGTTTTACAAGGCGAATAGGGCGCATACATACTTGGGCAACC 1740
                     *********  *************************************************

Wild            1741 CGGAATGTGAGAGCGAGATATATCCAGATTTTGTGACTATTGCTAAGGGGTTCAATATTC 1800
P/R Mutation    1741 CGGAATGTGAGAGCGAGATATATCCAGATTTTGTGACTATTGCTAAGGGGTTCAATATTC 1800
P/W Mutation    1741 CGGAATGTGAGAGCGAGATATATCCAGATTTTGTGACTATTGCTAAGGGGTTCAATATTC 1800
P/S Mutation    1741 CGGAATGTGAGAGCGAGATATATCCAGATTTTGTGACTATTGCTAAGGGGTTCAATATTC 1800
P/W/S Mutation  1741 CGGAATGTGAGAGCGAGATATATCCAGATTTTGTGACTATTGCTAAGGGGTTCAATATTC 1800
                     ************************************************************

Wild            1801 CTGCAGTCCGTGTAACAAAGAAGAGTGAAGTCCGTGCCGCCATCAAGAAGATGCTCGAGA 1860
P/R Mutation    1801 CTGCAGTCCGTGTAACAAAGAAGAGTGAAGTCCGTGCCGCCATCAAGAAGATGCTCGAGA 1860
P/W Mutation    1801 CTGCAGTCCGTGTAACAAAGAAGAGTGAAGTCCGTGCCGCCATCAAGAAGATGCTCGAGA 1860
P/S Mutation    1801 CTGCAGTCCGTGTAACAAAGAAGAGTGAAGTCCGTGCCGCCATCAAGAAGATGCTCGAGA 1860
P/W/S Mutation  1801 CTGCAGTCCGTGTAACAAAGAAGAGTGAAGTCCGTGCCGCCATCAAGAAGATGCTCGAGA 1860
                     ************************************************************

Wild            1861 CTCCAGGGCCATACTTGTTGGATATCATCGTCCCGCACCAGGAGCATGTGCTGCCTATGA 1920
P/R Mutation    1861 CTCCAGGGCCATACTTGTTGGATATCATCGTCCCGCACCAGGAGCATGTGCTGCCTATGA 1920
P/W Mutation    1861 CTCCAGGGCCATACTTGTTGGATATCATCGTCCCGCACCAGGAGCATGTGCTGCCTATGA 1920
P/S Mutation    1861 CTCCAGGGCCATACTTGTTGGATATCATCGTCCCGCACCAGGAGCATGTGCTGCCTATGA 1920
P/W/S Mutation  1861 CTCCAGGGCCATACTTGTTGGATATCATCGTCCCGCACCAGGAGCATGTGCTGCCTATGA 1920
                     ************************************************************

Wild            1921 TCCCAAGTGGGGGCGCATTCAAGGACATGATCCTGGATGGTGATGGCAGGACTGTGTATT 1980
```

Fig. 2D

```
P/R Mutation    1921 TCCCAAGTGGGGGCGCATTCAAGGACATGATCCTGGATGGTGATGGCAGGACTGTGTATT 1980
P/W Mutation    1921 TCCCAAGTGGGGGCGCATTCAAGGACATGATCCTGGATGGTGATGGCAGGACTGTGTATT 1980
P/S Mutation    1921 TCCCAATTGGGGGCGCATTCAAGGACATGATCCTGGATGGTGATGGCAGGACTGTGTATT 1980
P/W/S Mutation  1921 TCCCAATTGGGGGCGCATTCAAGGACATGATCCTGGATGGTGATGGCAGGACTGTGTATT 1980
                     *****.******************************************************

Wild            1981 AATCTATAATCTGTATGTTGGCAAAGCACCAGCCCGGCCTATGTTTGACCTGAATGACCC 2040
P/R Mutation    1981 AATCTATAATCTGTATGTTGGCAAAGCACCAGCCCGGCCTATGTTTGACCTGAATGACCC 2040
P/W Mutation    1981 AATCTATAATCTGTATGTTGGCAAAGCACCAGCCCGGCCTATGTTTGACCTGAATGACCC 2040
P/S Mutation    1981 AATCTATAATCTGTATGTTGGCAAAGCACCAGCCCGGCCTATGTTTGACCTGAATGACCC 2040
P/W/S Mutation  1981 AATCTATAATCTGTATGTTGGCAAAGCACCAGCCCGGGCTATGTTTGACCTGAATGACCC 2040
                     ************************************************************

Wild            2041 ATAAAGAGTGGTATGCCTATGATGTTTGTATGTGCTCTATCAATAACTAAGGTGTCAACT 2100
P/R Mutation    2041 ATAAAGAGTGGTATGCCTATGATGTTTGTATGTGCTCTATCAATAACTAAGGTGTCAACT 2100
P/W Mutation    2041 ATAAAGAGTGGTATGCCTATGATGTTTGTATGTGCTCTATCAATAACTAAGGTGTCAACT 2100
P/S Mutation    2041 ATAAAGAGTGGTATGCCTATGATGTTTGTATGTGCTCTATCAATAACTAAGGTGTCAACT 2100
P/W/S Mutation  2041 ATAAAGAGTGGTATGCCTATGATGTTTGTATGTGCTCTATCAATAACTAAGGTGTCAACT 2100
                     ************************************************************

Wild            2101 ATGAACCATATGCTCTTCTGTTTTACTTGTTTGATGTGCTTGGCATGGTAATCCTAATTA 2160
P/R Mutation    2101 ATGAACCATATGCTCTTCTGTTTTACTTGTTTGATGTGCTTGGCATGGTAATCCTAATTA 2160
P/W Mutation    2101 ATGAACCATATGCTCTTCTGTTTTACTTGTTTGATGTGCTTGGCATGGTAATCCTAATTA 2160
P/S Mutation    2101 ATGAACCATATGCTCTTCTGTTTTACTTGTTTGATGTGCTTGGCATGGTAATCCTAATTA 2160
P/W/S Mutation  2101 ATGAACCATATGCTCTTCTGTTTTACTTGTTTGATGTGCTTGGCATGGTAATCCTAATTA 2160
                     ************************************************************

Wild            2161 GCTTCCTGCTGTCTAGGTTTGTAGTGTGTTGTTTTCTGTAGGCATATGCATCACAAGATA 2220
P/R Mutation    2161 GCTTCCTGCTGTCTAGGTTTGTAGTGTGTTGTTTTCTGTAGGCATATGCATCACAAGATA 2220
P/W Mutation    2161 GCTTCCTGCTGTCTAGGTTTGTAGTGTGTTGTTTTCTGTAGGCATATGCATCACAAGATA 2220
P/S Mutation    2161 GCTTCCTGCTGTCTAGGTTTGTAGTGTGTTGTTTTCTGTAGGCATATGCATCACAAGATA 2220
P/W/S Mutation  2161 GCTTCCTGCTGTCTAGGTTTGTAGTGTGTTGTTTTCTGTAGGCATATGCATCACAAGATA 2220
                     ************************************************************

Wild            2221 TCATGTAAGTTTCTTGTCCTACATATCAATAATAAGAGAATAAAGTACTTCTATGCAAAA 2280
P/R Mutation    2221 TCATGTAAGTTTCTTGTCCTACATATCAATAATAAGAGAATAAAGTACTTCTATGCAAAA 2280
P/W Mutation    2221 TCATGTAAGTTTCTTGTCCTACATATCAATAATAAGAGAATAAAGTACTTCTATGCAAAA 2280
P/S Mutation    2221 TCATGTAAGTTTCTTGTCCTACATATCAATAATAAGAGAATAAAGTACTTCTATGTAAAA 2280
P/W/S Mutation  2221 TCATGTAAGTTTGTTGTCGTACATATCAATAATAAGAGAATAAAGTACTTCTATGTAAAA 2280
                     ************************************************...****

Wild            2281 AAAAAAAAAAAAAAAAAAAA                                          2301
P/R Mutation    2281 AAAAAAAAAAAAAAAAAAAA                                          2301
P/W Mutation    2281 AAAAAAAAAAAAAAAAAAA                                           2300
P/S Mutation    2281 AAAAAAAAAAAAAA                                                2294
P/W/S Mutation  2281 AAAAAAAAAAAAAA                                                2294
                     **************......
```

Fig. 18A

```
1st Nucleotide Sequence
    File Name       : Nipponbare ALS partial cDNA
    Sequence Size   : 1505

2nd Nucleotide Sequence
    File Name       : X63554 maize ALS 1
    Sequence Size   : 2544
```

```
    1'                                        ACCCACGCGTCGATGTGGAGGA
                                              **** *** *** ** **
 1141" CATCGTCGAGGTCAGCCGGTCCATCACCAAGCACAACTACCTGGTCCTCGACGTCGACGA

24' CATCCCCGCGTCATACAGGAAGCCTTCTTCCTCGCGTCCTCGGGCCGTCCTGGCCCGGT
        ************ * ***** ************* ****** *** *** ** *****
 1201" CATCCCCGCGTCGTGCAGGAGGCCTTCTTCCTCGCATCCTCTGGTCGCCCGGGGCCGGT

84' GCTGGTCGACATCCCCAAGGACATCCAGCAGCAGATGGCCGTGCCGGTCTGGGACACCTC
        ** ** ************************************ ***** ********* *
 1261" GCTTGTTGACATCCCCAAGGACATCCAGCAGCAGATGGCGGGTGCCGGCCTGGGACACGCC

144' GATGAATCTACCAGGGTACATCGCAGGCCTGCCCAAGCCAGCCGGCGACAGAATTGCTTGA
        **** *** ** *************** ***** ********** ***** ******
 1321" CATGAGTCTGCCTGGGTACATCGGCGCGCCTTCCCAAGCCTCCCGCGACTGAATTTCTTGA

204' GCAGGTCTTGCGTCTGGTTGGCGACTGACGGCGCCCGATTCTCTATGTCGGTGGTGGCTG
        ****** ******* ****** ** ************ **** ***** ** *********
 1381" GCAGGTGGTGCGTCTTGTTGGTGAATCACGGCGCCCTGTTCTTTATGTTGGCGGTGGCTG

264' CTCTGCATCTGGTGACGAATTGCGCTGGTTTGTTGAGCTGACTGGTATCCCAGTTACAAC
        * ***** ***** ** ** ** * ***** *** ******** ******** *****
 1441" TGCAGCATCAGGTGAGGAGTTGTGCCGCTTTGTGGAGTTGACTGGAATCCCAGTCACAAC

324' CACTCTGATGGGCCTCGGCAATTTCCCCAGTGACGACCCGTTGTCCCTGCGCATGCTTGG
        *** ******** **** **** ******** ********* **** **************
 1501" TACTGTTATGGGCCTTGGCAACTTCCCCAGCGACGACCCACTGTCACTGCGCATGCTTGG

384' GATGCATGGCACGGTGTACGCAAATTATGCCGTGGATAAGGCTGACCTGTTGCTTGCGTT
        *********** ***** ****** ******** ** *********** **
 1561" TATGCATGGCACAGTGTATGCAAATTATGCAGTGGATAAGGCGGATCTGTTGCTTGCATT

444' TGGTGTGCGGTTTGATGATCGTGTGACAGGGAAAATTGAGGCTTTTGCAAGCAGGGCCAA
        *************************************************** **** ** **
 1621" TGGTGTGCGGTTTGATGATCGTGTGACAGGGAAAATTGAGGCTTTTGCAGGCAGAGCTAA

504' GATTGTGCACATTGACATTGATCCAGCAGAGATTGGAAAGAACAAGCAACCACATGTGTC
        *************** ******** ** ******** *************** ***********
 1681" GATTGTGCACATTGATATTGATCCTGCTGAGATTGGCAAGAACAAGCAGCCACATGTGTC

564' AATTTGCGCAGATGTTAAGCTTGCTTTACAGGGCTTGAATGCTCTGGTACAACAGAGCAC
        * ** ****** ** ************* ****** ****** ****** ** *** *******
 1741" CATCTGTGCAGATGTTAAGCTTGCTTTGCAGGGCTGAAATACTCTTCTGGAAGGAAGCAC

624' AACAAAGACAAGTTCTGATTTTAGTGCATGGCACAATGAGTTGGACCAGCAGAAGAGGGA
        * ******* ** * **** ** * ******** **** ****** ***** *********
 1801" ATCAAAGAAGAGCTTTGACTTCGGCTCATGGCATGATGAATTGGATCAGCAAAAGAGGGA

684' GTTTCCTCTGGGGTACAAAACTTTTGGTGAAGAGATGCCCACGGCAATATGCCATTCAGGT
        ****** ** ** ** ***** ** *** ** **** ** ********* *********
 1861" GTTTCCCCTTGGATATAAAATCTTCAATGAGGAAATCCAGCCACAATATGCTATTCAGGT

744' GCTGGATGAGCTGACGAAAGGTGAGGCAATCATCGCTACTGGTGTTGGGCAGCACCAGAT
        ** ****** ******** ** ******* ******** ** ** *******************
 1921" TCTTGATGAGTTGACGAAGGGGGAGGCCATCATTGCCACAGGTGTTGGGCAGCACCAGAT

804' GTGGCGGCACAATATTACACCTACAAGCGGCCACGGCAGTGGCTGTCTTGGGCTGGTCT
        ************* ******** ****************** ************** **** *
 1981" GTGGGCGGCACAGTATTACACTTACAAGCGGCCAAGGCAGTGGCTGTCTTCAGCTGGTCT

864' GGGCGCAATGGGATTTGGGCTGCCTGCTGCAGCTGGTGCTTCTGTGGCTAACCCAGGTGT
        ** ** ************ ***** ***** ******** ********** **********
 2041" TGGGGCTATGGGATTTGGTTTGCCGGCTGCTGCTGGTGCTGCTGTGGCCCAACCCAGGTGT

924' CACAGTTGTTGATATTGATGGGGATGGTAGCTTCCTCATGAACATTCAGGAGCTGGCATT
        *** ******** ** ** ** ****************************** ** *
```

Fig. 18B

```
2101" CACTGTTGTTGACATCGACGGAGATGGTAGCTTCCTCATGAACATTCAGGAGCTAGCTAT

984' GATCCGCATTGAGAACCTCCCTGTGAAGGTGATGGTGTTGAACAACCAACATTTGGGTAT
      ******  ************* **  *****   * ***  * ********  ** * ** **
2161" GATCCGTATTGAGAACCTCCCAGTCAAGGTCTTTGTGCTAAACAACCAGCACCTCGGGAT

1044' GGTGGTGCAATGGGAGGATAGGTTTTACAAGGCGAATAGGGCGCATACATACTTGGGCAA
      ********  ******** *****  **  *****  *****  **  ** ****  ****** **
2221" GGTCGTGCAGTGGGAGGACAGGTTCTATAAGGCCAATAGAGCACACACATTCTTGGGAAA

1104' CCCGGAATGTGAGAGCGAGATATATCCAGATTTTGTGACCTATTGCTAAGGGGTTCAATA
      ***  **      ** **  ***************** ****    *  ********* ******** *
2281" CCCAGAGAACGAAAGTGAGATATATCCAGATTTTGTG-GCAATTGCTAAAGGGTTCAACA

1164' TTCCTGCAGTCCGTGTAACAAAGAAGAGTGAAGTCCGTGCCGCCATCAAGAAGATGCTCG
      ****  **********  *************  *******  *** **  ************** *
2340" TTCCAGCAGTCCGTGTGACAAAGAAGAGCGAAGTCCATGCAGCAATCAAGAAGATGCTTG

1224' AGACTCCAGGGCCATACTTGTTGGATATCATCGTCCCGCACCAGGAGCATGTGCTGCCTA
      **  *********  ***  *  ********  **********************  ******
2400" AGGCTCCAGGGCCGTACCTCTTGGATATAATCGTCCCGCACCAGGAGCATGTGTTGCCTA

1284' TGATCCCAAGTGGGGGCGCATTCAAGGACATGATCCTGGATGGTGATGGCAGGACTGTGT
      ******  *****  ** **  ********  *********************************
2460" TGATCCCTAGTGGTGGGGCTTTCAAGGATATGATCCTGGATGGTGATGGCAGGACTGTGT

1344' ATTAATCTATAATCTGTATGTTGGCAAAGCACCAGCCCGGCCTATGTTTGACCTGAATGA
      ***  ***   *   ***  *  **  *  **
2520" ATTGATCCGTTGACTGCAGGTCGAC
```

Fig. 19A

```
1st Nucleotide Sequence
  File Name      : 2-point mutant full-length ALS cDNA
2nd Nucleotide Sequence
  File Name      : wild type full-length ALS cDNA 1'                   CTCGCCGCCGCCGCCGCCGCCACCACCCACCATGGCTACGACCG
                         ********************************************
    1"  CCCAAACCGAGAAACCCTCGCCGCCGCCGCCGCCGCCACCACCCACCATGGCTACGACCG 45'  CCGCGGCCGCGGCCGGCCGCCCTGTCCGCCGCCGCGACGGCCAAGACCGGCCGTAAGAACC
        ************************************************************
   61"  CCGCGGCCGCGGCCGCCGCCCTGTCCGCCGCCGCGACGGCCAAGACCGGCCGTAAGAACC 105'  ACCAGCGACACCACGTCCTTCCCGCTCGAGGCCGGGTGGGGGCGGCGGCGGTCAGGTGCT
        ************************************************************
  121"  ACCAGCGACACCACGTCCTTCCCGCTCGAGGCCGGGTGGGGGCGGCGGCGGTCAGGTGCT 165'  CGGCGGTGTCCCCGGTCACCCCGCCGTCCCCGGCGCCGCCGGCCACGCCGCTCCGGCCGT
        ************************************************************
  181"  CGGCGGTGTCCCCGGTCACCCCGCCGTCCCCGGCGCCGCCGGCCACGCCGCTCCGGCCGT 225'  GGGGGCCGGCCGAGCCCCGCAAGGGCGCGGACATCCTCGTGGAGGCGCTGGAGCGGTGCG
        ************************************************************
  241"  GGGGGCCGGCCGAGCCCCGCAAGGGCGCGGACATCCTCGTGGAGGCGCTGGAGCGGTGCG 285'  GCGTCAGCGACGTGTTCGCCTACCCGGGCGGCGCGTCCATGGAGATCCACCAGGCGCTGA
        ************************************************************
  301"  GCGTCAGCGACGTGTTCGCCTACCCGGGCGGCGCGTCCATGGAGATCCACCAGGCGCTGA 345'  CGCGCTCCCCGGTCATCACCAACCACCTCTTCCGCCACGAGCAGGGCGAGGCCTTCGCGG
        ************************************************************
  361"  CGCGCTCCCCGGTCATCACCAACCACCTCTTCCGCCACGAGCAGGGCGAGGCCTTCGCGG 405'  CGTCCGGGTACGCGCGCGCGTCCGGCCGCGTCGGGGTCTGCGTCGCCACCTCCGGCCCCG
        ************************************************************
  421"  CGTCCGGGTACGCGCGCGCGTCCGGCCGCGTCGGGGTCTGCGTCGCCACCTCCGGCCCCG 465'  GGGCAACCAACCTCGTGTCCGCGCTCGCCGACGCGCTGCTCGACTCCGTCCCGATGGTCG
        ************************************************************
  481"  GGGCAACCAACCTCGTGTCCGCGCTCGCCGACGCGCTGCTCGACTCCGTCCCGATGGTCG 525'  CCATCACGGGCCAGGTCCCCCGCCGCATGATCGGCACCGACGCCTTCCAGGAGACGCCCA
        ************************************************************
  541"  CCATCACGGGCCAGGTCCCCCGCCGCATGATCGGCACCGACGCCTTCCAGGAGACGCCCA 585'  TAGTCGAGGTCACCCGCTCCATCACCAAGCACAATTACCTTGTCCTTGATGTGGAGGACA
        ************************************************************
  601"  TAGTCGAGGTCACCCGCTCCATCACCAAGCACAATTACCTTGTCCTTGATGTGGAGGACA 645'  TCCCCCGCGTCATACAGGAAGCCTTCTTCCTCGCGTCCTCGGGCCGTCCTCGGCCGGTGC
        ************************************************************
  661"  TCCCCCGCGTCATACAGGAAGCCTTCTTCCTCGCGTCCTCGGGCCGTCCTCGGCCGGTGC 705'  TGGTCGACATCCCCAAGGACATCCAGCAGCAGATGGCCGTGCCGGTCTGGGACACCTCGA
        ************************************************************
  721"  TGGTCGACATCCCCAAGGACATCCAGCAGCAGATGGCCGTGCCGGTCTGGGACACCTCGA 765'  TGAATCTACCAGGGTACATCGCACGCCTGCCCAAGCCACCCGCGACAGAATTGCTTGAGC
        ************************************************************
  781"  TGAATCTACCAGGGTACATCGCACGCCTGCCCAAGCCACCCGCGACAGAATTGCTTGAGC 825'  AGGTCTTGCGTCTGGTTGGCGAGTCACGGCGCCCGATTCTCTATGTCGGTGGTGGCTGCT
        ************************************************************
  841"  AGGTCTTGCGTCTGGTTGGCGAGTCACGGCGCCCGATTCTCTATGTCGGTGGTGGCTGCT 885'  CTGCATCTGGTGACGAATTGCGCTGGTTTGTTGAGCTGACTGGTATCCCAGTTACAACCA
        ************************************************************
  901"  CTGCATCTGGTGACGAATTGCGCTGGTTTGTTGAGCTGACTGGTATCCCAGTTACAACCA 945'  CTCTGATGGGCCTCGGCAATTTCCCCAGTGACGACCCGTTGTCCCTGCGCATGCTGGGA
        ***********************************************************
  961"  CTCTGATGGGCCTCGGCAATTTCCCCAGTGACGACCCGTTGTCCCTGCGCATGCTGGGA

1005'  TGCATGGCACGGTGTACGGCAAATTATGCCGTGGATAAGGCTGACCTGTTGCTTGCGTTTG
```

Fig. 19B

```
1021' TGCATGGCACGGTGTACGCAAATTATGCCGTGGATAAGGGCTGACCTGTTGCTTGCGTTTG

1065' GTGTGCGGTTTGATGATCGTGTGACAGGGAAAATTGAGGCTTTTGCAAGCAGGGCCAAGA
      ************************************************************
1081" GTGTGCGGTTTGATGATCGTGTGACAGGGAAAATTGAGGCTTTTGCAAGCAGGGCCAAGA

1125' TTGTGCACATTGACATTGATCCAGCAGAGATTGGAAAGAACAAGCAACCACATGTGTCAA
      ************************************************************
1141" TTGTGCACATTGACATTGATCCAGCAGACATTGGAAAGAACAAGCAACCACATGTGTCAA

1185' TTTGCGCAGATGTTAAGCTTGCTTTACAGGGCTTGAATGCTCTGCTACAACAGAGCACAA
      ************************************************************
1201" TTTGCGCAGATGTTAAGCTTGCTTTACAGGGCTTGAATGCTCTGCTACAACAGAGCACAA

1245' CAAAGACAAGTTCTGATTTTAGTGCATGGCACAATGAGTTGGACCAGCAGAAGAGGGAGT
      ************************************************************
1261" CAAAGACAAGTTCTGATTTTAGTGCATGGCACAATGAGTTGGACCAGCAGAAGAGGGAGT

1305' TTCCTCTGGGGTACAAAACTTTTGGTGAAGAGATCCGACCGCAATATGCCATTCAGGTGC
      ************************************************************
1321" TTGCTCTGGGGTACAAAACTTTTGGTGAAGAGATCCGACCGCAATATGCCATTCAGGTGC

1365' TGGATGAGCTGACGAAAGGTGAGGCAATCATCGCTACTGGTGTTGGGCAGCACCAGATGT
      ************************************************************
1381" TGGATGAGCTGACGAAAGGTGAGGCAATCATCGCTACTGGTGTTGGGCAGCACCAGATGT

1425' GGGCGGCACAATATTACACCTACAAGCGGCCACGGCAGTGGCTGTCTTCGGCTGGTCTGG
      ************************************************************
1441" GGGCGGCACAATATTACACCTACAAGCGGCCACGGCAGTGGCTGTCTTCGGCTGGTCTGG

1485' GCGCAATGGGATTTGGGCTGCCTGCTGCAGCTGGTGCTTCTGTGGCTAACCCAGGTGTCA
      ************************************************************
1501" GCGCAATGGGATTTGGGCTGCCTGCTGCAGCTGGTGCTTCTGTGGCTAACCCAGGTGTCA

1545' CAGTTGTTGATATTGATCGGGATGGTAGCTTCCTCATGAACATTCAGGAGCTGGCATTGA
      ************************************************************
1561" CAGTTGTTGATATTGATCGGGATGGTAGCTTCCTCATGAACATTCAGGAGCTGGCATTGA

1605' TCCGCATTGAGAACCTCCCTGTGAAGGTGATGGTGTTGAACAACCAACATTTGGGTATGG
      ************************************************************
1621" TCCGCATTGAGAACCTCCCTGTGAAGGTGATGGTGTTGAACAACCAACATTTGGGTATGG

1665' TGGTGCAATTGGAGGATAGGTTTTACAAGGCGAATAGGGCGCATACATACTTGGGCAACC
      ********  ***************************************************
1681" TGGTGCAATGGGAGGATAGGTTTTACAAGGCGAATAGGGCGCATACATACTTGGGCAACC

1725' CGGAATGTGAGAGCGAGATATATCCAGATTTTGTGACTATTGCTAAGGGGTTCAATATTC
      ************************************************************
1741" CGGAATGTGAGAGCGAGATATATCCAGATTTTGTGACTATTGCTAAGGGGTTCAATATTC

1785' CTGCAGTCCGTGTAACAAAGAAGAGTGAAGTCCGTGCCGCCATCAAGAAGATGCTCGAGA
      ************************************************************
1801" CTGCAGTCCGTGTAACAAAGAAGAGTGAAGTCCGTGCCGCCATCAAGAAGATGCTCGAGA

1845' CTCCAGGGCCATACTTGTTGGATATCATCGTCCCGCACCAGGAGCATGTGCTGCCTATGA
      ************************************************************
1861" CTCCAGGGCCATACTTGTTGGATATCATCGTCCCGCACCAGGAGCATGTGCTGCCTATGA

1905' TCCCAATTGGGGCGCATTCAAGGACATGATCCTGGATGGTGATGGCAGGACTGTGTATT
      ******  ****************************************************
1921" TCCCAAGTGGGGCGCATTCAAGGACATGATCCTGGATGGTGATGGCAGGACTGTGTATT

1965' AATCTATAATCTGTATGTTGGCAAAGCACCAGCCCGGCCTATGTTTGACCTGAATGACCC
      ************************************************************
1981" AATCTATAATCTGTATGTTGGCAAAGCACCAGCCCGGCCTATGTTTGACCTGAATGACCC

2025' ATAAAGAGTGGTATGCCTATGATGTTTGTATGTGCTCTATCAATAACTAAGGTGTCAACT
      ************************************************************
2041" ATAAAGAGTGGTATGCCTATGATGTTTGTATGTGCTCTATCAATAACTAAGGTGTCAACT

2085' ATGAACCATATGCTCTTCTGTTTTACTTGTTTGATGTGCTTGGCATGGTAATGGTAATTA
      ************************************************************
2101" ATGAACCATATGCTCTTCTGTTTTACTTGTTTGATGTGCTTGGCATGGTAATGGTAATTA

2145' GCTTCCTGCTGTCTAGGTTTGTAGTGTGTTGTTTTCTGTAGGCATATGCATCACAAGATA
```

Fig. 19C

```
          ************************************************************
    2161" GCTTCCTGCTGTCTAGGTTTGTAGTGTGTTGTTTTCTGTAGGCATATGCATCACAAGATA

2205' TCATGTAAGTTTCTTGTCCTACATATCAATAATAAGAGAATAAAGTACTTCTATGTAAAA
          ******************************************************* ****
    2221" TCATGTAAGTTTCTTGTCCTACATATCAATAATAAGAGAATAAAGTACTTCTATGCAAAA

2265' AAAAAAAAAAAAAAA
          ***************
    2281" AAAAAAAAAAAAAAAAAAAAAA
```

GENE CODING FOR ACETOLACTATE SYNTHASE

CROSS-REFERENCE

This application is a Divisional of U.S. application Ser. No. 10/509,121 (now abandoned), filed on Sep. 28, 2004, which is the national phase of PCT/JP03/01917 filed on Feb. 21, 2003 which designated the United States and which claims priority to Japanese Application 2002-095721 filed on Mar. 29, 2002. The entire contents of the above applications are hereby incorporated by reference.

FIELD OF THE INVENTION

The present invention relates to a gene coding for acetolactate synthase which is a rate-limiting enzyme in the branched-chain amino acid biosynthetic pathway.

BACKGROUND OF THE INVENTION

Acetolactate synthase (hereinafter referred to as "ALS") is a rate-limiting enzyme in the biosynthetic pathway of branched chain amino acids, such as leucine, valine and isoleucine, and is known as an essential enzyme for the growth of plants. ALS is also known to be present in a wide variety of higher plants. In addition, ALS is found in various microorganisms, such as yeast (*Saccharomyces cerevisiae*), *Escherichia coli*, and *Salmonella typhimurium*.

Three types of isoenzymes of ALS are known to be present in *Escherichia coli* and *Salmonella typhimurium*. Each of these isoenzymes is a hetero oligomer consisting of catalytic subunits with a large molecular weight that govern catalytic activity of the enzyme and regulatory subunits with a small molecular weight that function as feedback inhibitors by binding of branched-chain amino acids (Chipman et al., Biochim. Biophys. Acta. 1385, 401-419, 1998). Catalytic subunits are located at Ilv IH, Ilv GM and Ilv BN operons, respectively. On the other hand, ALS in yeast is a single enzyme, which comprises a catalytic subunit and a regulatory subunit, as is the case in bacteria (Pang et al., Biochemistry, 38, 5222-5231, 1999). The catalytic protein subunit is located at the locus ILV2.

In plants, ALS is known to consist catalytic subunit(s) and regulatory subunit(s) as is the case in the above microorganisms (Hershey et al., Plant Molecular Biology. 40, 795-806, 1999). For example, the catalytic subunit of ALS in tobacco (dicotyledon) is coded by two gene loci, SuRA and SuRB (Lee et al., EMBO J. 7, 1241-1248, 1988); and that in maize is coded by two gene loci, als 1 and als 2 (Burr et al., Trends in Genetics 7, 55-61, 1991; Lawrence et al., Plant Mol. Biol. 18, 1185-1187, 1992). The nucleotide sequences of genes coding for a catalytic subunit have been completely determined for dicotyledonous plants including tobacco, *Arabidopsis*, rapeseed, cotton, *Xanthium, Amaranthus* and *Kochia* (see Chipman et al., Biochim. Biophys. Acta. 1385, 401-419, 1998 and domestic re-publication of PCT international publication for patent applications WO97/08327). However, maize and rice (Kaku et al., the 26th Conference of Pesticide Science Society of Japan, Lecture Abstracts, p 101, 2001) are the only monocotyledonous plants whose nucleotide sequences have been completely determined.

Meanwhile, herbicides, for example, sulfonylurea herbicides, imidazolinon herbicides, triazolopyrimidine herbicides and pyrimidinyl carboxy herbicides (hereinafter referred to as "PC herbicides"), are known to suppress the growth of a plant by inhibiting ALS (Ray, Plant Physiol. 75, 827-831, 1984; Shaner et al., Plant Physiol. 76, 545-546, 1984; Subramanian et al., Plant Physiol. 96, 310-313, 1991; Shimizu et al., J. Pestic. Sci. 19, 59-67, 1994).

As shown in Tables 1 and 2, known plants having resistance to these herbicides contain a gene coding for ALS that includes substitution of one or two nucleotides which induces substitution of one or two amino acids in a region conserved among different species.

TABLE 1

Mutation in plant ALS which imparts resistance against ALS-inhibiting type herbicide (1)

| Plant species | Mutation | Herbicide tested | Corresponding rice ALS amino acid |
|---|---|---|---|
| Zea mays | Ala90Thr | IM | Ala96Thr |
| Arabidopsis thaliana | Ala122Val | | Ala96Val |
| Xantium strumarium | Ala100Thr | IM | Ala96Thr |
| Beta vulgaris | Ala113Thr | IM/SU | Ala96Thr |
| Arabidopsis thaliana | Met124Glu | | Met98Glu |
| Arabidopsis thaliana | Met124Ile | | Met98Ile |
| Arabidopsis thaliana | Met124His | | Met98His |
| Lactuca serriola | Pro→His | SU | Pro171His |
| Kochia scoparia | Pro189Thr | SU | Pro171Thr |
| Kochia scoparia | Pro189Ser | SU | Pro171Ser |
| Kochia scoparia | Pro189Arg | SU | Pro171Arg |
| Kochia scoparia | Pro189Leu | SU | Pro171Leu |
| Kochia scoparia | Pro189Gln | SU | Pro171Gln |
| Kochia scoparia | Pro189Ala | SU | Pro171Ala |
| Brassica napus | Pro173Ser | | Pro171Ser |
| Nicotina tabacum | Pro196Gln | SU | Pro171Gln |
| Nicotina tabacum | Pro196Ala | SU | Pro171Ala |
| Nicotina tabacum | Pro196Ser | SU | Pro171Ser |
| Arabidopsis thaliana | Pro197Ser | SU | Pro171Ser |
| Arabidopsis thaliana | Pro197deletion | | Pro171deletion |
| Beta vulgaris | Pro188Ser | IM/SU | Pro171Ser |
| Sisymbrium orientale | Pro→Ile | | Pro171Ile |
| Brassica tournefortii | Pro→Ala | | Pro171Ala |
| Scirpus juncoides | Pro→Leu | SU | Pro171Leu |
| Scirpus juncoides | Pro179Ala | SU | Pro171Ala |
| Scirpus juncoides | Pro179Gln | SU | Pro171Gln |
| Scirpus juncoides | Pro179Ser | SU | Pro171Ser |
| Scirpus juncoides | Pro179Lys | SU | Pro171Lys |
| Lindernia micrantha | Pro→Gln | SU | Pro171Gln |
| Lindernia procumbens | Pro→Ser | SU | Pro171Ser |
| Lindernia dubia subsp. | Pro→Ser | SU | Pro171Ser |
| Lindernia dubia | Pro→Ala | SU | Pro171Ala |
| Arabidopsis thaliana | Arg199Ala | | Arg173Ala |
| Arabidopsis thaliana | Arg199Glu | | Arg173Glu |
| Xantium strumarium | Ala183Val | | Ala179Val |
| Arabidopsis thaliana | Phe206Arg | | Phe180Arg |

TABLE 2

Mutation in plant ALS which imparts resistance to ALS-inhibiting type herbicide (2)

| Plant species | Mutation | Herbicide tested | Corresponding rice ALS amino acid |
|---|---|---|---|
| Kochia scoparia | Asp260Gly | SU | Asp242Gly |
| Kochia scoparia | Trp487Arg | SU | Try465Arg |
| Kochia scoparia | Asn561Ser | SU | Asn539Ser |
| Kochia scoparia | Trp570Leu | | Trp548Leu |
| Gossypium hirsutum L. | Trp563Cys | SU ? | Try548Cys |
| Gossypium hirsutum L. | Trp563Ser | SU ? | Try548Ser |
| Brassica napus | Trp557Leu | | Try548Leu |
| Zea mays L. | Trp552Leu | IM | Try548Leu |
| Nicotina tabacum L. | Trp537Leu | SU | Try548Leu |
| Arabidopsis thaliana | Trp574Leu | | Try548Leu |
| Arabidopsis thaliana | Trp574Ser | | Try548Ser |
| Arabidopsis thaliana | Trp574deletion | | Try548deletion |
| Xantium strumarium | Trp552Leu | IM | Try548Leu |
| Oryza sativa. | Trp548Leu | PC | Try548Leu |
| Amaranthus sp. | Trp569Leu | | Try548Leu |

TABLE 2-continued

Mutation in plant ALS which imparts resistance to
ALS-inhibiting type herbicide (2)

| Plant species | Mutation | Herbicide tested | Corresponding rice ALS amino acid |
|---|---|---|---|
| *Amaransus rudis* | Trp569Leu | IMI | Try548Leu |
| *Sisymbrium orientale* | Trp→Leu | | Try548Leu |
| *Zea mays* | Ser621Asp | IM | Ser627Asp |
| *Zea mays* | Ser621Asn | IM | Ser627Asn |
| *Arabidopsis thaliana* | Ser653Asn | IM | Ser627Asn |
| *Arabidopsis thaliana* | Ser653Thr | | Ser627Thr |
| *Arabidopsis thaliana* | Ser653Phe | | Ser627Phe |
| *Arabidopsis thaliana* | Ser653deletion | | Ser627deletion |
| *Oryza sativa* | Ser627Ile | PC | Ser627Ile |
| *Kochia scoparia* | Val276Glu | SU | |

Examples of such a gene include a gene coding for ALS having resistance specific to sulfonylurea herbicides (see Kathleen et al., EMBO J. 7, 1241-1248, 1988; Mourad et al., Planta, 188, 491-497, 1992; Guttieri et al., Weed Sci. 43, 175-178, 1995; Bernasconi et al., J. Biol. Chem. 270, 17381-17385, 1995; and JP Patent Publication (Unexamined Application) No. 63-71184); a gene coding for ALS having resistance specific to imidazolinon herbicides (see Mourad et al., Planta, 188, 491-497, 1992; Lee et al., FEBS Lett. 452, 341-345, 1999; and JP Patent Publication (Unexamined Application) No. 5-227964); a gene coding for ALS having resistance to both sulfonylurea and imidazolinon herbicides (see Kathleen et al., EMBO J. 7, 1241-1248, 1988; Bernasconi et al., J. Biol. Chem. 270, 17381-17385, 1995; Hattori et al., Mol. Gen. Genet. 246, 419-425, 1995; Alison et al., Plant Physiol. 111, 1353, 1996; Rajasekarau et al., Plant Sci. 119, 115-124, 1996; JP Patent Publication (Unexamined Application) No. 63-71184; JP Patent Publication (Unexamined Application) No. 4-311392; and Bernasconi et al., U.S. Pat. No. 5,633,437, 1997); and a gene coding for ALS having a high level of resistance to PC herbicides (Kaku et al., the 26$^{th}$ Conference of Pesticide Science Society of Japan, Lecture Abstracts, p. 101, 2001). The production of a plant body showing resistance to both sulfonylurea and imidazolinon herbicides has been attempted by crossing a plant having ALS showing resistance specific to sulfonylurea herbicides with a plant having ALS showing resistance specific to imidazolinon herbicides (Mourad et al., Mol. Gen. Genet, 243, 178-184, 1994). Furthermore, artificial alteration of a gene coding for ALS into a herbicide resistance gene has been attempted (see Ott et al., J. Mol. Biol. 263, 359-368, 1996, JP Patent Publication (Unexamined Application) No. 63-71184, JP Patent Publication (Unexamined Application) No. 5-227964, JP Patent Publication (PCT Translation) No. 11-504213), such that it has been found that a single amino acid deletion causes ALS to show resistance to both sulfonylurea and imidazolinon herbicides (see JP Patent Publication (Unexamined Application) No. 5-227964).

As described above, ALSs having resistance to herbicides, and genes coding for ALS have been aggressively studied. However, only a few cases have been reported concerning a mutant ALS gene having resistance specific to a PC herbicide using resistance to PC herbicides as an indicator. Moreover, there have been also only a few cases reported concerning the study of the resistance to PC herbicides and other herbicides.

SUMMARY OF THE INVENTION

The purpose of the present invention is to provide a gene coding for an ALS protein showing extremely high level of resistance to PC herbicides or to sulfonylurea herbicides, an ALS protein coded by the gene, a recombinant vector having the gene, a transformant having the recombinant vector, a plant having the gene, a method for rearing the plant, and a method for selecting a transformant cell using the gene as a selection marker.

As a result of thorough studies to achieve the above purpose, we have completed the present invention by finding that a mutant ALS which is derived from the wild type ALS by substituting a certain amino acid residue of the wild type ALS with a certain amino acid shows extremely high resistance to PC herbicides.

(1) Specifically, the present invention is a gene which codes for the following protein (a) or (b):

a protein consisting of an amino acid sequence of any one of SEQ ID NOS: 2, 4, 6 and 8;

a protein consisting of an amino acid sequence derived from the amino acid sequence of any one of SEQ ID NOS: 2, 4, 6 and 8 by substitution, deletion or addition of at least one or more amino acids, which has resistance to PC herbicides and has acetolactate synthase activity.

(2) Further, the present invention is an acetolactate synthase protein, which is coded by the gene of (1).

(3) Furthermore, the present invention is a recombinant vector, which has the gene of (1).

(4) Further, the present invention is a transformant, which has the recombinant vector of (3).

(5) Moreover, the present invention is a plant, which has the gene of (1) and has resistance to PC herbicides.

(6) Further, the present invention is a method for cultivating the plant of (5) which comprises cultivating the plant in the presence of a PC herbicide.

(7) Still further, the present invention is a method for selecting a transformant cell having the gene of (1), which uses this gene as a selection marker.

Hereunder, a more detailed explanation will be given of the present invention.

The gene coding for the acetolactate synthase of the present invention (hereinafter referred to as "mutant ALS gene") codes for an acetolactate synthase protein (hereinafter referred to as "mutant ALS protein") having an amino acid sequence that is different from that of a wild type acetolactate synthase protein (hereinafter, referred to as "wild type ALS protein"). The mutant ALS protein can be obtained by mutating a certain site in a wild type ALS protein expressed in a rice plant. The mutant ALS protein of the present invention consists of the amino acid sequence of any one of SEQ ID NOS: 2, 4, 6, and 8.

The amino acid sequence of SEQ ID NO: 2 is derived from the amino acid sequence of the wild type ALS protein by substitution of proline 171 with histidine and substitution of arginine 172 with serine. A mutant ALS protein containing the amino acid sequence of SEQ ID NO: 2 is referred to as "P171H/R172S mutant ALS protein," or "P171H/R172S mutant."

The amino acid sequence of SEQ ID NO: 4 is derived from the amino acid sequence of the wild type ALS protein by substitution of proline 171 with histidine and substitution of tryptophan 548 with leucine. A mutant ALS protein containing the amino acid sequence of SEQ ID NO: 4 is referred to as "P171H/W548L mutant ALS protein," or "P171H/W548L mutant."

The amino acid sequence of SEQ ID NO: 6 is derived from the amino acid sequence of the wild type ALS protein by substitution of proline 171 with histidine, and substitution of serine 627 with isoleucine. A mutant ALS protein containing the amino acid sequence of SEQ ID NO: 6 is referred to as "P171H/S627I mutant ALS protein," or "P171H/S627I mutant."

The amino acid sequence of SEQ ID NO: 8 is derived from the amino acid sequence of the wild type ALS protein by substitution of proline 171 with histidine, substitution of tryptophan 548 with leucine, and substitution of serine 627 with isoleucine. A mutant ALS protein containing the amino acid sequence of SEQ ID NO: 8 is referred to as "P171H/W548L/S627I mutant ALS protein," or "P171H/W548L/S627I mutant."

FIGS. 1A and B show the results of comparisons among the amino acid sequences of these 4 types of mutant ALS proteins and the amino acid sequence of the wild type ALS protein. Further, in FIGS. 1A and B, the amino acid sequence in the $1^{st}$ row represents the wild type ALS protein, the amino acid sequence in the $2^{nd}$ row represents P171H/R172S mutant ALS protein, the amino acid sequence in the $3^{rd}$ row represents P171H/W548L mutant ALS protein, the amino acid sequence in the $4^{th}$ row represents P171H/S627I mutant ALS protein, and the amino acid sequence in the $5^{th}$ row represents P171H/W548L/S627I mutant ALS protein.

Compared to the wild type ALS protein, these mutant ALS proteins possess good resistance not only to PC herbicides, but also to sulfonylurea and imidazolinon herbicides. This can be determined by subcloning a gene coding for the mutant ALS protein into pGEX 2T, transforming *E. coli* or the like with the pGEX 2T, and then examining the sensitivity of the expressed mutant ALS protein to herbicides.

Examples of a PC herbicide include bispyribac-sodium, pyrithiobac-sodium and pyriminobac, as represented by the following chemical formula 1.

An example of a sulfonylurea herbicide is chlorsulfuron, as represented by the following chemical formula 2.

An example of an imidazolinon herbicide is imazaquin, as represented by the following chemical formula 3.

In particular, P171H/R172S mutant ALS protein shows resistance to a certain herbicide at a level not only better than that of a mutant ALS protein independently having P171H or R172S, but also superior to the combined resistance predicted from the mutant ALS proteins independently having P171H or R172S. Further, the mutant ALS protein independently having R172S does not show resistance to any herbicides, therefore the R172S mutation is a silent mutation. In other words, in P171H/R172S mutant ALS protein, R172S mutation, which is a silent mutation by itself, improves the resistance of P171H mutant ALS protein.

Further, P171H/W548L mutant protein shows resistance to a certain herbicide at a level not only better than that of a mutant ALS protein independently having P171H or W548L, but also better than the combined resistance predicted from the mutant ALS proteins independently having P171H or W548L. In other words, P171H/W548L mutant protein shows resistance which is far greater than the synergistic effect predicted from the resistances of both P171H mutant protein and W548L mutant protein.

Further, in particular, P171H/S627I mutant protein shows resistance to a certain herbicide at a level not only better than that of a mutant ALS protein independently having P171H or S627I, but also better than the combined resistance predicted from the mutant ALS proteins independently having P171H or S627I. In other words, P171H/S627I mutant protein shows resistance which is far greater than the synergistic effect predicted from the resistances of both P171H mutant protein and S627I mutant protein.

Still further, in particular, P171H/W548L/S627I mutant protein shows resistance to a certain herbicide better than that of a mutant ALS protein independently having P171H, W548L or S627I.

Moreover, the mutant ALS protein of the present invention may consist of any amino acid sequence derived from the amino acid sequence of any one of SEQ ID NOS: 2, 4, 6 and 8 by substitution, deletion or addition of at least one or more amino acids, as long as the sequence has resistance to a PC herbicide and has acetolactate synthase activity. Here, "one or more amino acids" preferably refers to 1 to 30 amino acids, more preferably 1 to 20 amino acids, and more preferably 1 to 10 amino acids.

Particularly, in the amino acid sequence of SEQ ID NO: 2, "at least one or more amino acids" are preferably (an) amino acids other than the $171^{st}$ and $172^{nd}$ amino acids. In the amino acid sequence of SEQ ID NO: 4, "at least one or more amino acids" are preferably (an) amino acids other than the $171^{st}$ and $548^{th}$ amino acids. In the amino acid sequence of SEQ ID NO: 6, "at least one or more amino acids" are preferably (an) amino acids other than the $171^{st}$ and $627^{th}$ amino acids. In the amino acid sequence of SEQ ID NO: 8, "at least one or more amino acids" are preferably (an) amino acids other than the $171^{st}$, $627^{th}$, and $548^{th}$ amino acids.

The mutant ALS gene of the present invention is not specifically limited, as long as it has a nucleotide sequence coding for the above-described mutant ALS protein. Examples of the nucleotide sequence include the nucleotide sequence of any one of SEQ ID NOS: 1, 3, 5 and 7. The nucleotide sequence of SEQ ID NO: 1 codes for the amino acid sequence of SEQ ID NO: 2, the nucleotide sequence of SEQ ID NO: 3 codes for the amino acid sequence of SEQ ID NO: 4, the nucleotide sequence of SEQ ID NO: 5 codes for the amino acid sequence of SEQ ID NO: 6, and the nucleotide sequence of SEQ ID NO: 7 codes for the amino acid sequence of SEQ ID NO: 8. The mutant ALS gene may have a nucleotide sequence derived from the nucleotide sequence of any one of SEQ ID NOS: 1, 3, 5 and 7 by substitution of a codon coding for a certain amino acid with a degenerate codon.

FIGS. 2A, B, C and D show the results of comparisons among the nucleotide sequences coding for these 4 types of mutant ALS proteins and the nucleotide sequence coding for a wild type ALS protein. In FIGS. 2A, B, C and D, the nucleotide sequence in the $1^{st}$ row represents the wild type ALS protein, the nucleotide sequence in the $2^{nd}$ row represents P171H/R172S mutant ALS protein, the nucleotide sequence in the $3^{rd}$ row represents P171H/W548L mutant ALS protein, the nucleotide sequence in the $4^{th}$ row represents P171H/S627I mutant ALS protein, and the nucleotide sequence in the $5^{th}$ row represents P171H/W548L/S627I mutant ALS protein.

Moreover, the mutant ALS gene of the present invention may consist of a nucleotide sequence which can hybridize under stringent conditions to a nucleotide sequence complementary to the nucleotide sequence of any one of SEQ ID NOS: 1, 3, 5 and 7, and codes for an amino acid sequence having acetolactate synthase activity. "Stringent conditions" refers to conditions wherein a so-called specific hybrid is formed and a non-specific hybrid is not formed. Examples of such stringent conditions include conditions whereby DNAs having high homology to each other (for example, DNAs having 50% or more homology to each other) hybridize and DNAs having low homology to each other do not hybridize. Specific examples of the stringent conditions, under which hybridization is possible, include conditions for washing in the normal Southern hybridization of 60° C., and a salt concentration corresponding to 1×SSC, 0.1% SDS, or preferably, 0.1×SSC, 0.1% SDS.

Genes coding for these mutant ALS proteins can be obtained by introducing a mutation as described above into a gene coding for a wild type ALS protein which is present in the genomic DNA of japonica type rice variety, Kinmaze. To introduce mutations, any known techniques can be employed. For example, site-directed mutagenesis can be used. Site-directed mutagenesis can be performed using a commercial kit, e.g., Mutan-K (Takara Shuzo), Gene Editor (Promega) or ExSite (Stratagene).

In addition, a gene coding for the mutant ALS protein can be obtained by culturing wild type culture cells sensitive to a PC herbicide in the presence of the PC herbicide and then obtaining the gene from mutant culture cells that appear and show resistance to the PC herbicide. Then, a gene coding for ALS protein having a new combination of mutations can be synthesized based on the thus found mutations by the PCR method and SPR (self polymerase reaction) method using enzymes.

Specifically, first, mRNAs are prepared from mutant culture cells resistant to a PC herbicide, cDNAs are synthesized, and then a cDNA library of λgt 11 phage is constructed. Then, the library is screened using a nucleic acid probe containing part of a gene coding for the wild type ALS protein. Next, the insert DNA of the resulting positive clone is subcloned into pBluescript II SK+, to determine the nucleotide sequence. For cDNA inserts that have been shown to have mutations, fragments containing the mutation are synthesized by the PCR and SPR methods using as a template pBluescript II SK+ retaining the insert DNA, and primers designed based on the wild type rice ALS gene. Meanwhile, genomic DNAs are prepared from PC-herbicide-resistant rice culture cells, and various primers are designed based on rice ALS genes. Then, primer walking is performed, so that the sequences of ALS genes present in the prepared genomic DNAs are determined, and mutations sites are found. When mutations are found, fragments containing the mutations are synthesized by the PCR and SPR methods. Fragments containing mutations synthesized from mutant ALS cDNA cloned into pBluescript II SK+ (including the fragments containing these mutations) are subcloned into pGEX 2T, and then *E. coli* is transformed using the vector.

Clones having the insert DNAs coding for the amino acid sequences represented by SEQ ID NOS: 2, 4, 6 or 8 are then selected, so that genes coding for mutant ALS proteins can be obtained. In addition, the thus obtained plasmid in which a gene coding for a mutant ALS protein containing the amino acid sequence represented by SEQ ID NO: 2 had been incorporated in pGEX 2T was deposited as Rice Mutant ALS cDNA 1 (FERM BP-7944), the plasmid in which a gene coding for a mutant ALS protein containing the amino acid sequence represented by SEQ ID NO: 4 had been incorporated in pGEX 2T was deposited as Rice Mutant ALS cDNA 2 (FERM BP-7945), the plasmid in which a gene coding for a mutant ALS protein containing the amino acid sequence represented by SEQ ID NO: 6 had been incorporated in pGEX 2T was deposited as Rice Mutant ALS cDNA 3 (FERM BP-7946), and the plasmid in which a gene coding for a mutant ALS protein containing the amino acid sequence represented by SEQ ID NO: 8 had been incorporated in pGEX 2T was deposited as Rice Mutant ALS cDNA 4 (FERM BP-7947) with the Patent and Bio-Resource Center, National Institute of Advanced Industrial Science and Technology (Chuo-6, 1-1-1, Higashi, Tsukuba-shi, Ibaraki, JAPAN) on Mar. 8, 2002, under the Budapest Treaty.

On the other hand, transformation of a target plant using a gene coding for the mutant ALS protein can impart resistance to various herbicides, such as PC herbicides, to the plant. Any known technique can be used for transformation of a plant. For example, a foreign gene can be introduced into a target plant cell using *Agrobacterium tumefaciens*.

More specifically, a gene coding for the mutant ALS protein is inserted into a binary vector containing T-DNA sequence of a Ti plasmid of *Agrobacterium*. The Ti plasmid is transformed into *E. coli* and the like. Then, the binary vectors retaining the gene coding for the mutant ALS protein replicated by, e.g., *E. coli* are transformed into Agrobacteria which contain helper plasmids. Target plants are infected with the Agrobacteria, and then the transformed plants are identified. When the identified transformed plant is a culture cell, the plant cell can be regenerated into a complete plant by any known technique.

To transform a target plant with a gene coding for the mutant ALS protein, the gene can be directly introduced using known standard techniques. Examples of a method which transforms an expression vector containing a gene coding for the mutant ALS protein include the polyethylene glycol method, electroporation, and the particle gun method.

A gene coding for the mutant ALS protein may be transformed into any type of plant, such as monocotyledonous and dicotyledonous plants. Examples of a target crop into which a gene coding for the mutant ALS protein is transformed include rice, maize, wheat, barley, soybean, cotton, rapeseeds, sugar beet and tobacco. In addition, turf grass, trees and the like can be transformed by introducing a gene coding for the mutant ALS protein.

In any of the above cases, transformation of a plant using a gene coding for the mutant ALS protein can impart resistance to PC herbicides, sulfonylurea herbicides, and imidazolinon herbicides to the plant.

Moreover, a gene coding for the mutant ALS protein can also be used as a selection marker in an experiment for transformation of a plant. For example, to transform a plant cell using a target gene, a vector which has a gene coding for the mutant ALS protein and a target gene is introduced into the plant cell, followed by culturing of the plant cell under the presence of a PC herbicide or the like. If a plant cell survives in the presence of the herbicide, it indicates that the plant cell contains a gene coding for the mutant ALS protein and the gene of interest introduced therein. Further, whether a target gene and a gene coding for the mutant ALS protein are incorporated into the chromosome of a plant cell can be confirmed by observing the phenotype of the plant and then examining the presence of these genes on the genome, by genome southern hybridization or PCR.

BRIEF DESCRIPTION OF THE DRAWINGS

FIG. 14 is a characteristic figure showing the relation between the fraction number and absorbance at OD 525 nm in anion exchange column chromatography performed for the purpose of separating the wild type ALS protein.

FIG. 15 is a characteristic figure showing sensitivity of the wild type ALS protein and the mutant ALS protein to bispyribac-sodium.

FIG. 18A shows a nucleotide sequence comparison between Nippon-bare EST (SEQ ID NO: 35) and maize ALS gene (SEQ ID NO: 36).

FIG. 18B is a continuation from FIG. 18A and shows a nucleotide sequence comparison between Nippon-bare EST and maize ALS gene.

FIG. 19A is a nucleotide sequence comparison between the full-length cDNA derived from Sr line (SEQ ID NO: 37) and wild type ALS cDNA 1 (SEQ ID NO: 38).

FIG. 19B is a continuation from FIG. 19A, and shows a nucleotide sequence comparison between the full-length cDNA derived from Sr line and wild type cDNA 1.

FIG. 19C is a continuation from FIG. 19B, and shows a nucleotide sequence comparison between the full-length cDNA derived from Sr line and wild type cDNA 1.

FIG. 22 shows processes for synthesizing ALS cDNAs independently having C512A (P171H) mutation or C514A (R172S) mutation, and for constructing pGEX 2T retaining the ALS cDNA. Asterisks denote mutated points.

FIG. 25 shows processes for synthesizing P171H/W548L/S627I mutant ALS cDNA and for constructing pGEX 2T retaining the ALS cDNA. Asterisks denote mutated points.

BEST MODE FOR CARRYING OUT THE INVENTION

Figure 3:
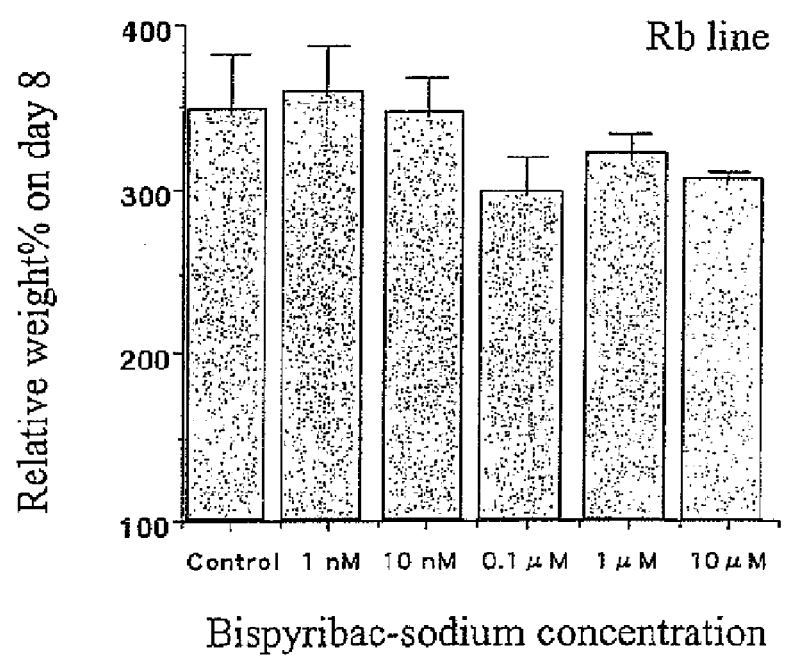
FIG. 3 is a characteristic figure showing sensitivity of Rb line to bispyribac-sodium.
Figure 4:
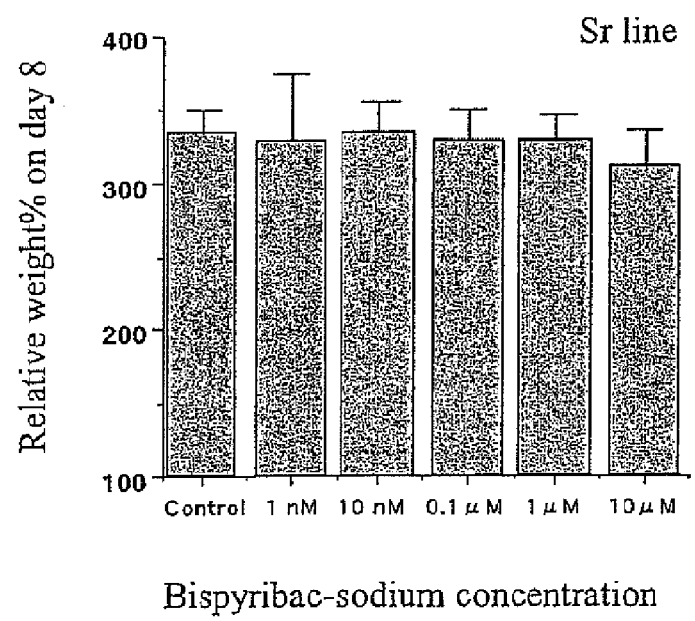
FIG. 4 is a characteristic figure showing sensitivity of Sr line to bispyribac-sodium.
Figure 5:
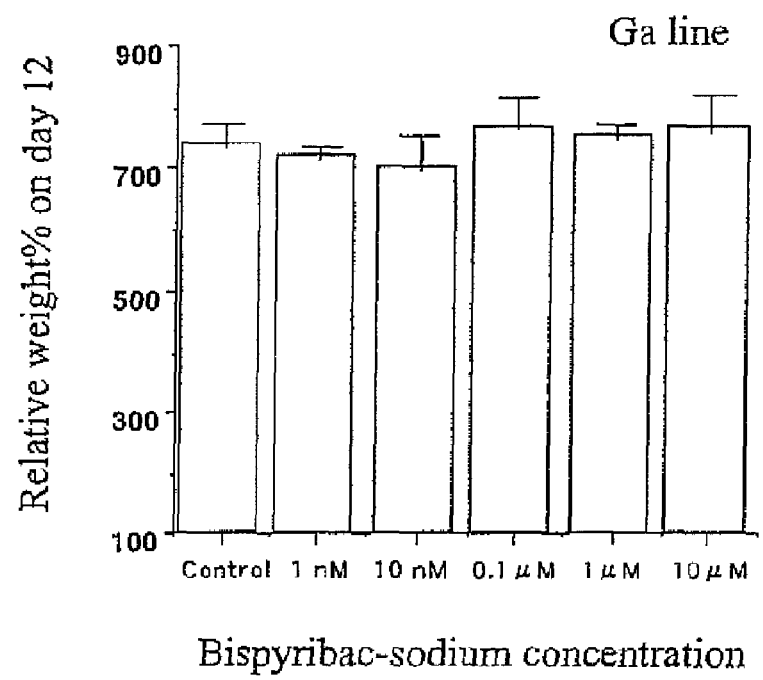
FIG. 5 is a characteristic figure showing sensitivity of Ga line to bispyribac-sodium.
Figure 6:
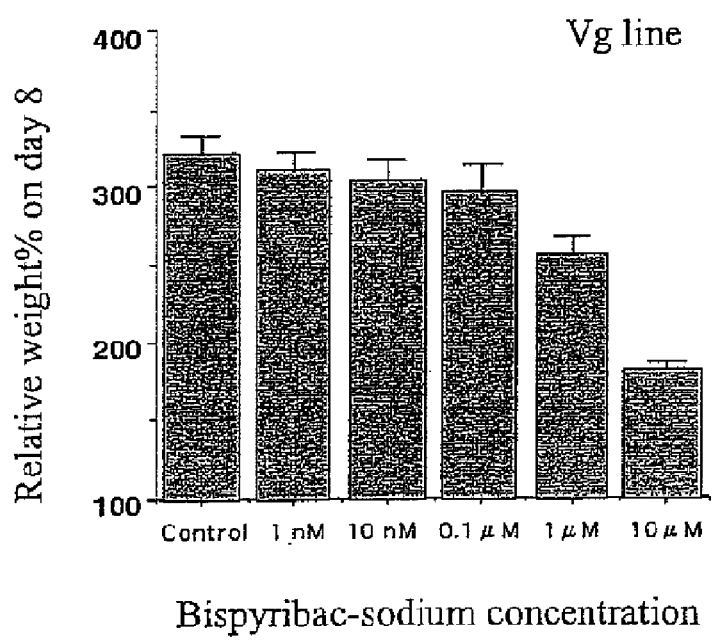
FIG. 6 is a characteristic figure showing sensitivity of Vg line to bispyribac-sodium.

Now, the present invention will be further described by the following examples, but the technical scope of the invention is not limited by these examples.

Example 1

Production of Rice (Kinmaze) Culture Cells Resistant to a PC Herbicide

Chaff was removed from rice seeds (variety: Kinmaze, scientific name: *Oryza sativa* var. Kinmaze). The seeds were immersed in 70% ethanol for 5 minutes, and then immersed in about 5% antiformin for 20 minutes, followed by washing several times with sterile distilled water. Then, the seeds were static-cultured on a medium with a composition as shown in Table 3.

TABLE 3

| | |
|---|---|
| Inorganic salt (mixed saline for Murashige-Skoog medium) | 1 pack |
| Thiamin•HCl (0.1 g/l) | 1 ml |
| Nicotinic acid (0.5 g/l) | 1 ml |
| Pyridoxine•HCl (0.5 g/l) | 1 ml |
| Glycine (2 g/l) | 1 ml |
| myo-inositol (50 g/l) | 2 ml |
| 2,4-D (200 ppm) | 10 ml |
| Sucrose | 30 g |
| Gelrite | 3 g |
| Prepare the medium to 1000 ml with distilled water, and adjust pH to 5.7. | |

In the above medium composition, 2,4-D is synthesized auxin. To prepare the medium, first, a medium with the above composition was placed in a 1 l beaker, and distilled water was added to the beaker to 1000 ml. Next, the solution was adjusted to pH 5.7, and supplemented with 3 g of Gelrite. The Gelrite was dissolved well by heating with a microwave oven, and then the mixture was added 30 ml at a time to culture flasks using a pipetter. Next, three sheets of aluminum foil were laid over the culture flask, followed by heating for sterilization in an autoclave at 121° C. for 15 to 20 minutes. Finally the solution was cooled to room temperature so that the media for static culture of the above seeds were prepared.

Next, endosperm portions were removed from the callus induced on the medium, and then subculture was performed.

Then, part of the obtained calli was sub-cultured, that is, cultured successively once per two weeks in a liquid medium (the composition is the same as in that shown in Table 3, but not supplemented with Gelrite) supplemented with 1 μM bispyribac-sodium (one type of PC herbicides). Two to 6 weeks later the culture cells started to wither. About 2 months later, a plurality of non-discolored cell masses that were thought to be conducting cell division were obtained from among culture cell populations most of which had died and became discolored brown. These cell masses were isolated and cultured, so that a plurality of cell lines that can proliferate in the presence of 2 μM bispyribac-sodium were obtained. The obtained cell lines were named Rb line, Sr line, Ga line and Vg line, respectively.

Subsequently, the resulting plurality of cell lines were cultured while elevating the concentration of bispyribac-sodium in an orderly manner. As a result, cell lines that can proliferate in the presence of 100 μM bispyribac-sodium were obtained. The bispyribac-sodium resistant culture cells (hereinafter referred to as "resistant mutant") were sub-cultured on MS-2, 4-D solid media supplemented with 1 to 10 μM bispyribac-sodium. Part of the sub-cultured resistant mutant was sampled, added into MS-2,4-D liquid media not supplemented with bispyribac-sodium, and then subjected to suspended cell culture at a cycle of 8 to 10 days.

Figure 7:
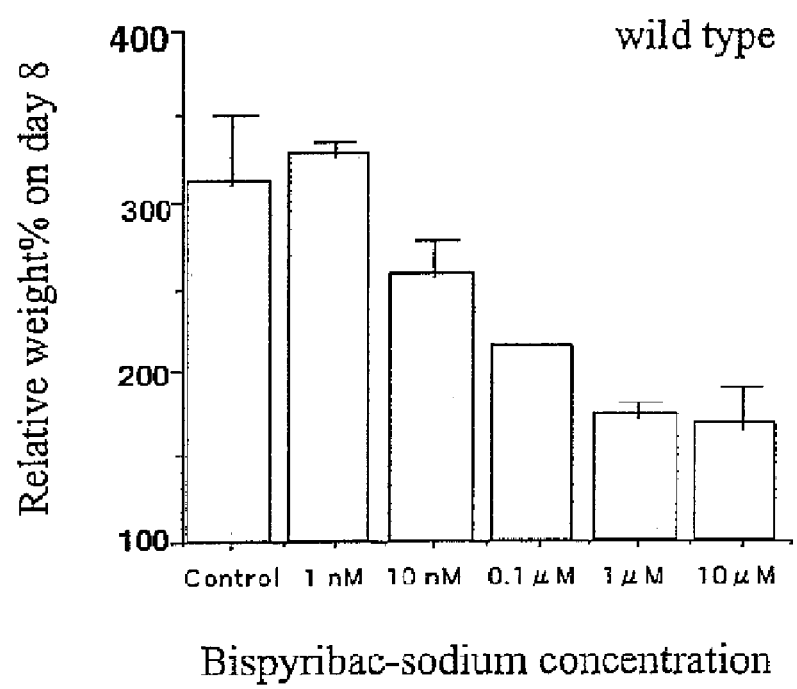
FIG. 7 is a characteristic figure showing sensitivity of the wild type to bispyribac-sodium.

Approximately 1.5 g (wet weight) of the resistant mutant was transplanted into a 200 ml Erlenmeyer flask supplemented with 50 ml of a MS-2,4-D liquid medium and bispyribac-sodium at a certain concentration, followed by culturing at approximately 27° C. for a certain period. The wet weight of the callus was measured periodically. The relative amount of increase was determined based on the wet weight of the transplanted resistant mutant. In addition, the experiment was performed three times with different bispyribac-sodium concentrations, and the standard error was calculated. FIGS. 3 to 6 show the relation between changes in bispyribac-sodium concentration and the relative weight on day 8 or 12 in the resistant mutant. As a control, a similar experiment was conducted using the wild type (Kinmaze). FIG. 7 shows the result of measuring the relation between bispyribac-sodium concentration and relative weight on day 8 in the wild type (Kinmaze).

As shown in FIG. 7, the growth of the wild type was not inhibited in a group supplemented with 1 nM bispyribac-sodium, but was inhibited in a group supplemented with 10 nM or more bispyribac-sodium. On the other hand, as shown in FIGS. 3 to 6, almost none of the growth of the resistant mutants (Rb line, Sr line, Ga line, and Vg line) other than Vg line was affected even in a group supplemented with 10 μM bispyribac-sodium. Even in Vg line, it was shown that the effect of bispyribac-sodium on the growth was smaller than that in the wild type.

Figure 8:
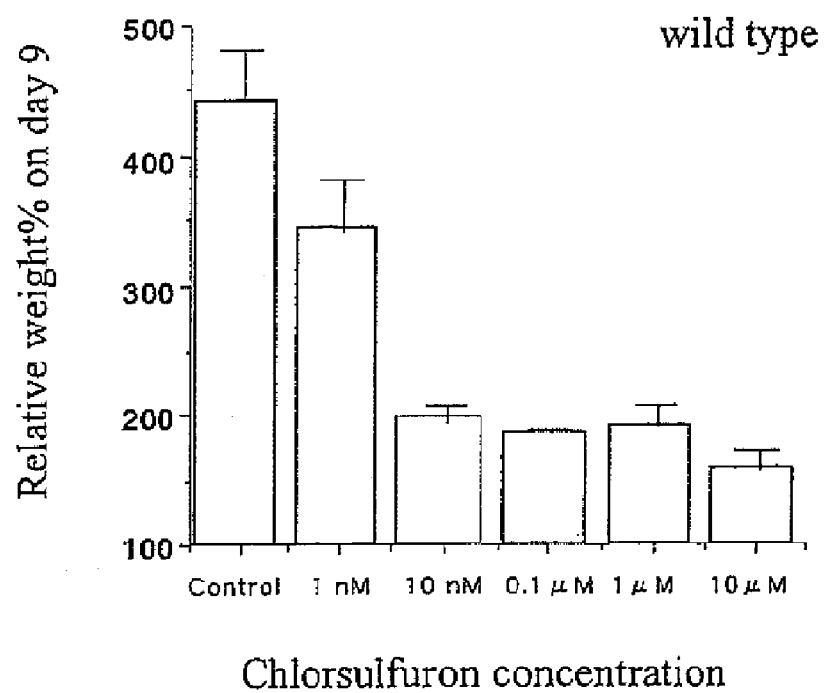
FIG. 8 is a characteristic figure showing sensitivity of the wild type to chlorsulfuron.
Figure 9:
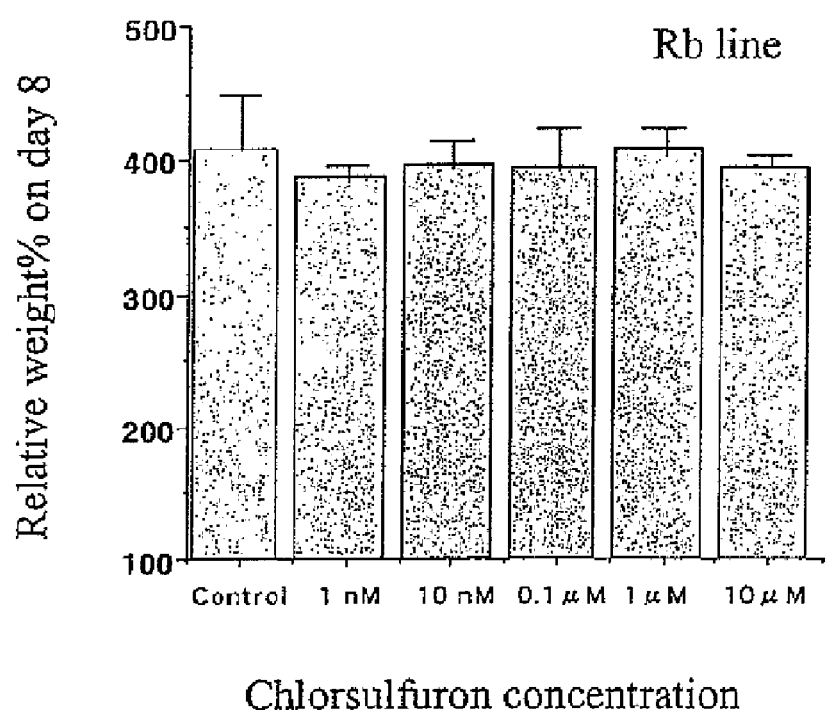
FIG. 9 is a characteristic figure showing sensitivity of Rb line to chlorsulfuron.
Figure 10:
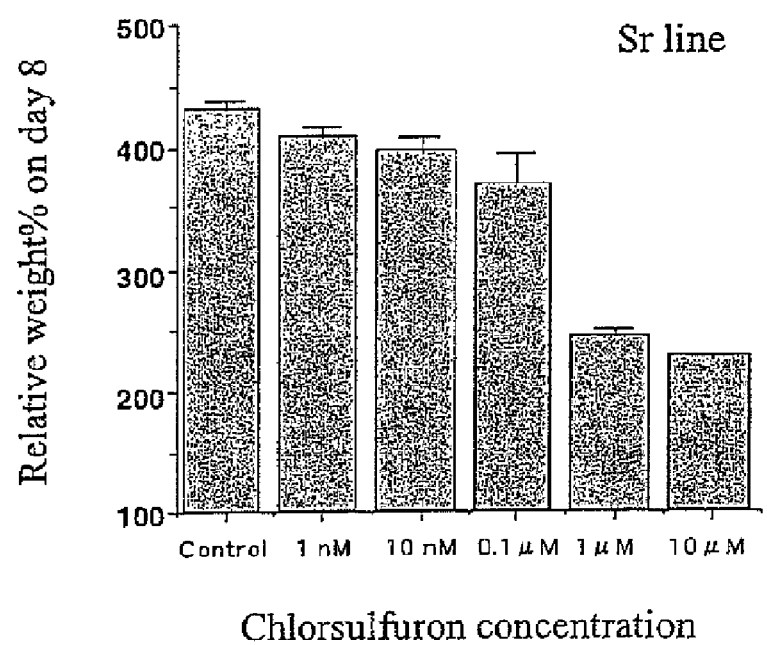
FIG. 10 is a characteristic figure showing sensitivity of Sr line to chlorsulfuron.
Figure 11:
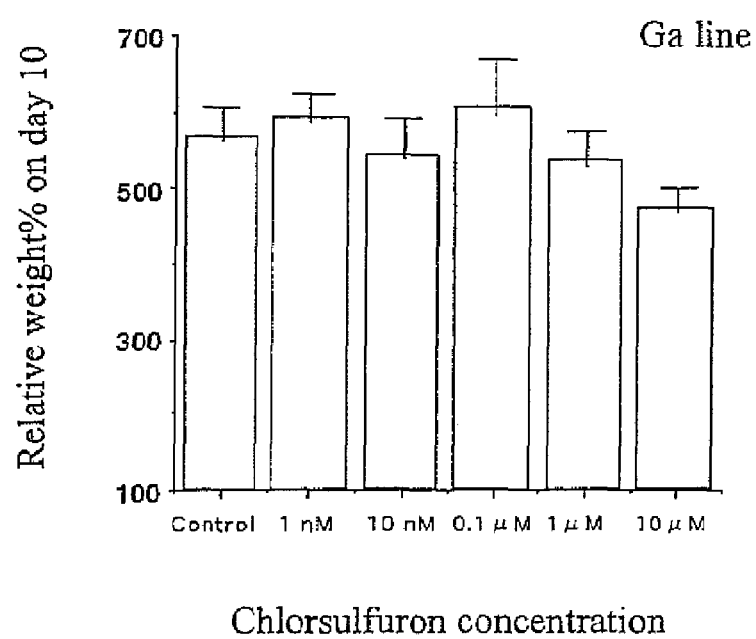
FIG. 11 is a characteristic figure showing sensitivity of Ga line to chlorsulfuron.
Figure 12:
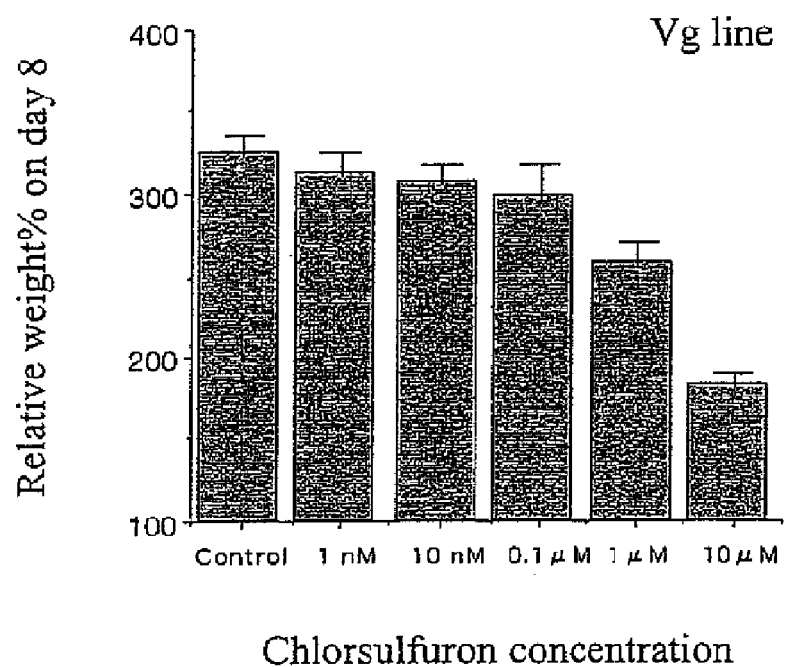
FIG. 12 is a characteristic figure showing sensitivity of Vg line to chlorsulfuron.

Also, in the case of using chlorsulfuron instead of bispyribac-sodium, the growth rates of the wild type and the resistant mutants were measured as described above. FIG. 8 shows the relation between changes in chlorsulfuron concentration and relative weight on day 9 in the wild type. Further, FIGS. 9 to 12 show the relation between changes in chlorsulfuron concentration and relative weight on day 8 or 10 in the resistant mutants, that is, Rb line, Sr line, Ga line and Vg line.

As shown in FIG. 8, the growth of the wild type was inhibited by addition of 1 nM chlorsulfuron, showing that the wild type has higher sensitivity to chlorsulfuron than to bispyribac-sodium. However, as shown in FIGS. 9 to 12, Rb line, Sr line, Ga line and Vg line differed in sensitivity, but the growth was not inhibited so much by addition of chlorsulfuron, showing their resistance to chlorsulfuron. Sensitivity to bispyribac-sodium and chlorsulfuron remained almost unchanged in both the wild type and the resistant mutants, even with longer culture duration. The growth rate was almost the same in the wild type and the resistant mutants.

These results revealed that the resistant mutants possess high resistance to bispyribac-sodium. Moreover, the resistant mutants were shown to have improved resistance to chlorsulfuron compared to the wild type.

Example 2

Herbicide Sensitivity of ALS Protein Partially Purified from the Resistant Mutant In this example, mutant ALS protein was partially purified from the resistant mutants obtained in Example 1 (Rb line, Sr line and Vg line, with Ga line excluded), and then herbicide sensitivity of the obtained mutant ALS protein was examined. The mutant ALS protein was partially purified as follows.

First, 200 g or more of resistant mutant was prepared by a liquid culture method (no supplementation with bispyribac-sodium), using a composition as shown in Table 3 excluding Gelrite. Then, about 150 g of the resistant mutant was homogenized using Hiscotron in a volume of buffer-1 [100 mM potassium phosphate buffer (pH 7.5) containing 20% (v/v) glycerol, 0-5 mM thiamin pyrophosphate (TPP), 10 μM flavin adenine dinucleotide (FAD), 0.5 mM $MgCl_2$, and a volume of polyvinyl polypyrrolidone one-tenth that of tissue volume] 3-fold greater than tissue volume. The homogenate was filtered through nylon gauze, and then centrifuged at 15000×g for 20 minutes. Ammonium sulfate was added to the centrifuged supernatant to 50% saturation, and then allowed to stand in ice for approximately 1 hour. The mixture was again centrifuged at 15000×g for 20 minutes, and then the precipitated fraction was dissolved in approximately 30 ml of buffer-2 [10 mM Tris hydrochloric acid buffer (pH 7.5) containing 20% (v/v) glycerol, 0.5 mM TPP and 0.5 mM $MgCl_2$]. The mixture was again centrifuged at 15000×g for 20 minutes, and then the supernatant fraction was applied to a Sephadex G-25 (Amersham Bioscience). About 40 ml of the fraction that had passed through the column was collected as a crude enzyme solution.

Next, the protein concentration of the crude enzyme solution was measured by the Bradford method according to the manual of Bio-Rad Protein Assay. The crude enzyme solution was then filtered through a Whatman filter (Whatman), and then the crude enzyme solution in an appropriate protein amount (10 to 15 ml) was applied to three vertically-connected HiTrap Q columns (Amersham Bioscience) using a FPLC device (Amersham Bioscience). After protein component was adsorbed using HiTrap Q, unadsorbed fractions were washed out using buffer-2 having a volume 3 to 5 fold greater than the bed volume. Then, the adsorbed protein component was eluted using an eluate having a volume 10 fold greater than the bed volume (150 ml). Here, the eluate was prepared by dissolving KCl with a linear concentration gradient (0 to 0.4 M) into buffer-2. The eluate containing the eluted protein component was apportioned, 5 ml each, into a plurality of test tubes for apportioning. Further, to stabilize ALS protein contained in the eluted protein component, 0.5 ml of buffer-2 containing 20 mM sodium pyruvate had been previously added to each test tube for apportioning.

ALS activity resulting from the mutant ALS protein contained in the eluted fractions apportioned into each test tube for apportioning was measured as follows. A reaction solution to be used in a measurement reaction was prepared by mixing an eluted fraction to be measured with a solution comprising 20 mM sodium pyruvate, 0.5 mM TPP, 0.5 mM MgCl$_2$, 10 µM FAD and 20 mM potassium phosphate buffer (pH 7.5). One ml of this reaction solution was used. After the eluted fraction to be measured was added, the measurement reaction was performed at 30° C. for 40 to 60 minutes. Then, the reaction was stopped by addition of 0.1 ml of 6N sulfuric acid (or 0.25 N sodium hydroxide).

After the reaction was stopped, the reaction solution was incubated at 60° C. for 10 minutes, thereby converting acetolactate contained in the reaction solution to acetoin.

Then, to quantify acetoin contained in the reaction solution, 1 ml of 0.5% (w/v) creatine and 1 ml of 5% (w/v) α-naphthol dissolved in 2.5 N sodium hydroxide was added to the reaction solution, followed by incubation at 37° C. for 10 minutes. Acetoin was then quantified by color comparison of the absorbance (at 525 nm) of the reaction solution, thereby evaluating ALS activity. In addition, since the reaction solution contained a small amount of sodium pyruvate, reaction time 0 was used as control.

Figure 13:
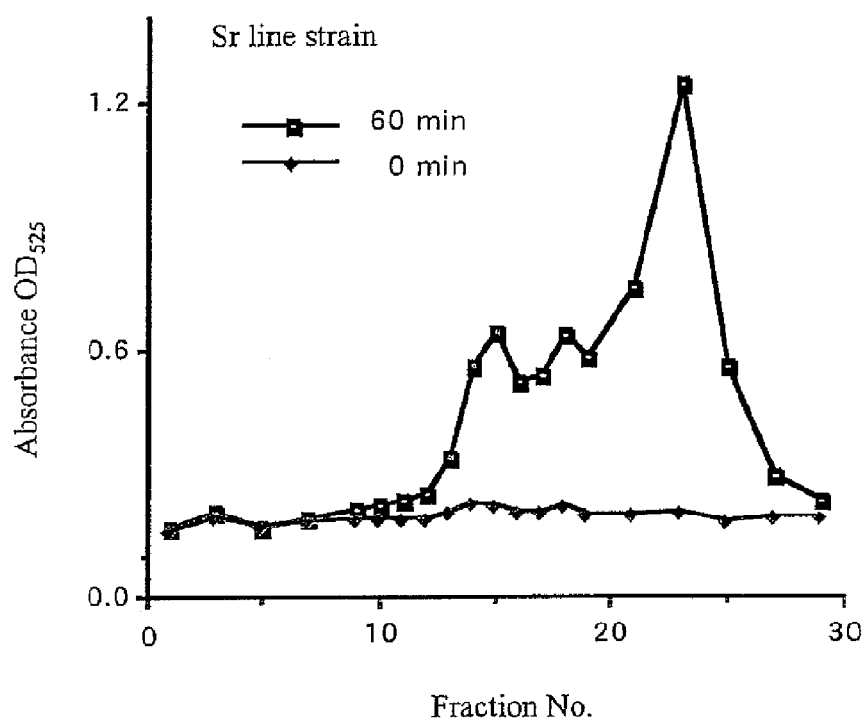
FIG. 13 is a characteristic figure showing the relation between the fraction number and absorbance at OD 525 nm in anion exchange column chromatography performed for the purpose of separating the ALS protein of the resistant mutant.
Figure 1:
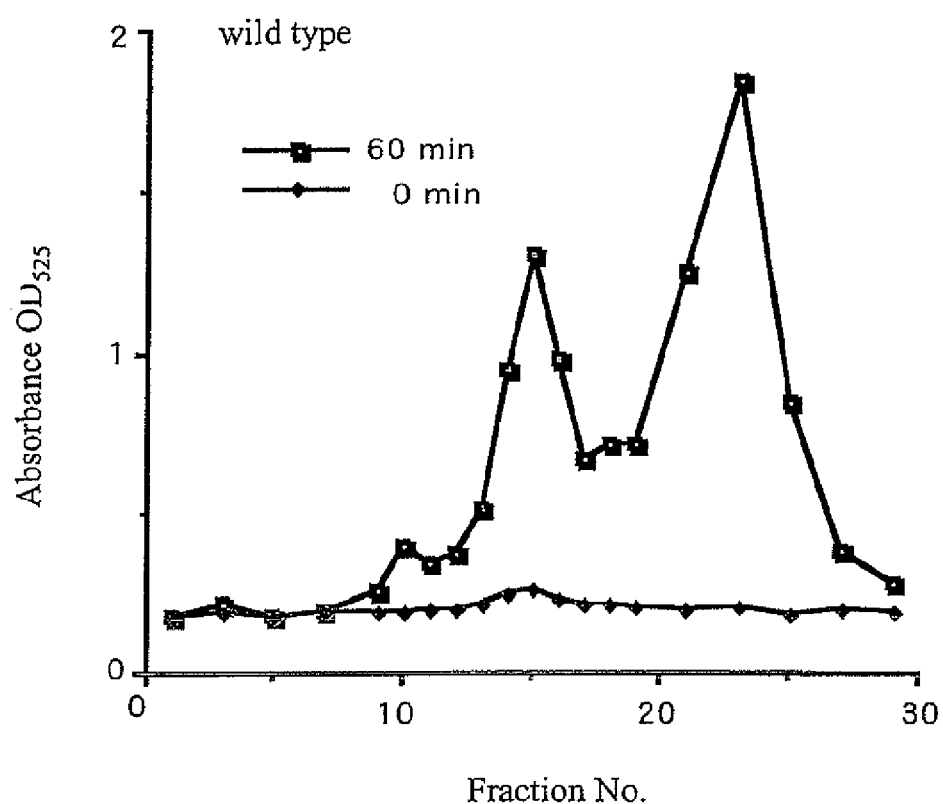
FIG. 1A shows an amino acid sequence comparison between the mutant ALS proteins and the wild type ALS protein.
FIG. 1B is a continuation from FIG. 1A, and shows an amino acid sequence comparison between the mutant ALS proteins (SEQ ID NOS: 2, 4, 6, 8) and the wild type ALS protein (SEQ ID NO: 39).
Figure 1:
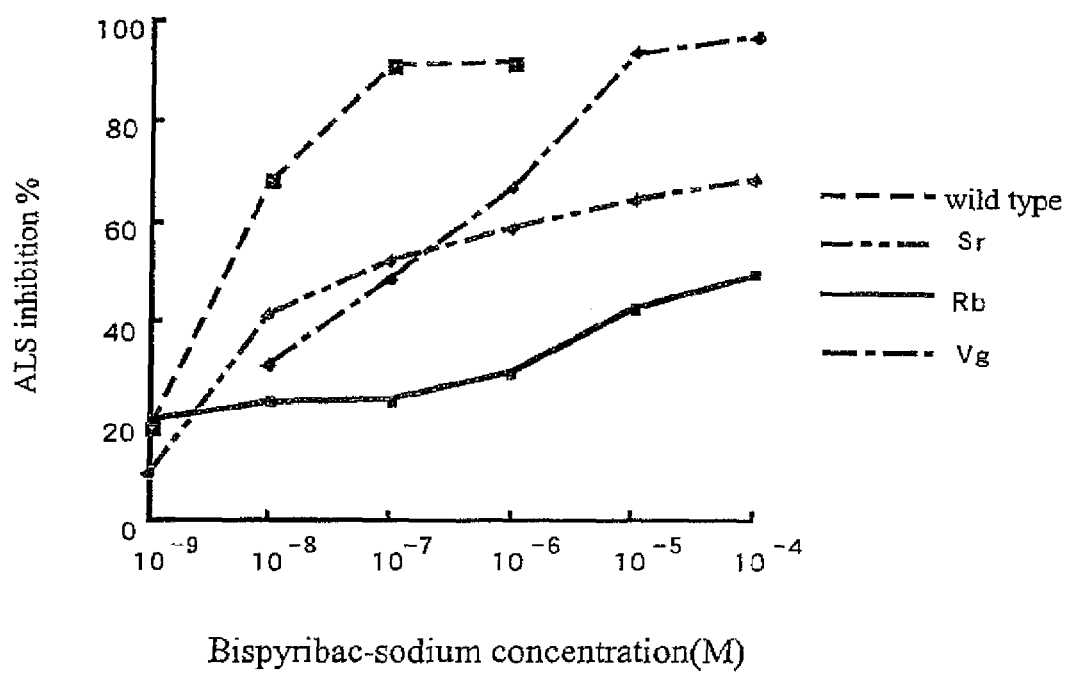

As a result, absorbance at OD525 nm was as high as approximately 7 per 0.2 ml of the reaction solution. However, when the above measurement reaction was ceased with sodium hydroxide, and acetoin generation activity due to activity other than ALS activity was examined, nearly 80% of the apparent ALS activity resulted from direct acetoin generation activity which was not due to activity of the mutant ALS protein. Accordingly, the mutant ALS protein and the other proteins were separated for acetoin generation activity by FPLC using anion exchange resin. FIG. 13 shows the result in the case of using Sr line as a resistant mutant. As a result, three activity peaks were detected as shown in FIG. 13.

To determine which one of the three activity peaks corresponded to the mutant ALS protein, acetoin generation activity was examined for each peak. Thus, it was found that a fraction shown by the peak of initial elution corresponded to the mutant ALS protein.

Using the enzyme solution containing the mutant ALS protein, sensitivity of the mutant ALS protein to bispyribac-sodium, chlorsulfuron and imazaquin was examined. Sensitivity to each of these herbicides was evaluated by measuring ALS activity in the same manner as in the above measurement reaction, except that a herbicide was added to a certain concentration before addition of the enzyme solution. For comparison, the wild type ALS protein was separated and purified (FIG. 14) in the same manner and used for the experiment. In addition, bispyribac-sodium was prepared as an aqueous solution, and chlorsulfuron and imazaquin were prepared as acetone solutions. The final concentration of acetone in the reaction mixture was 1%.

Figure 16:
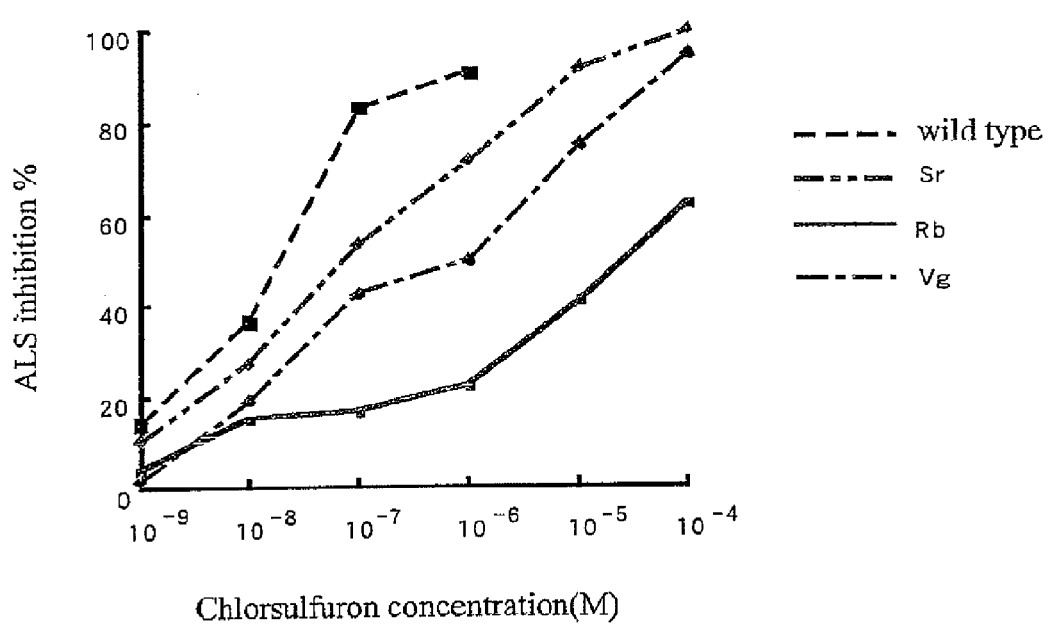
FIG. 16 is a characteristic figure showing sensitivity of the wild type ALS protein and the mutant ALS protein to chlorsulfuron.
Figure 17:
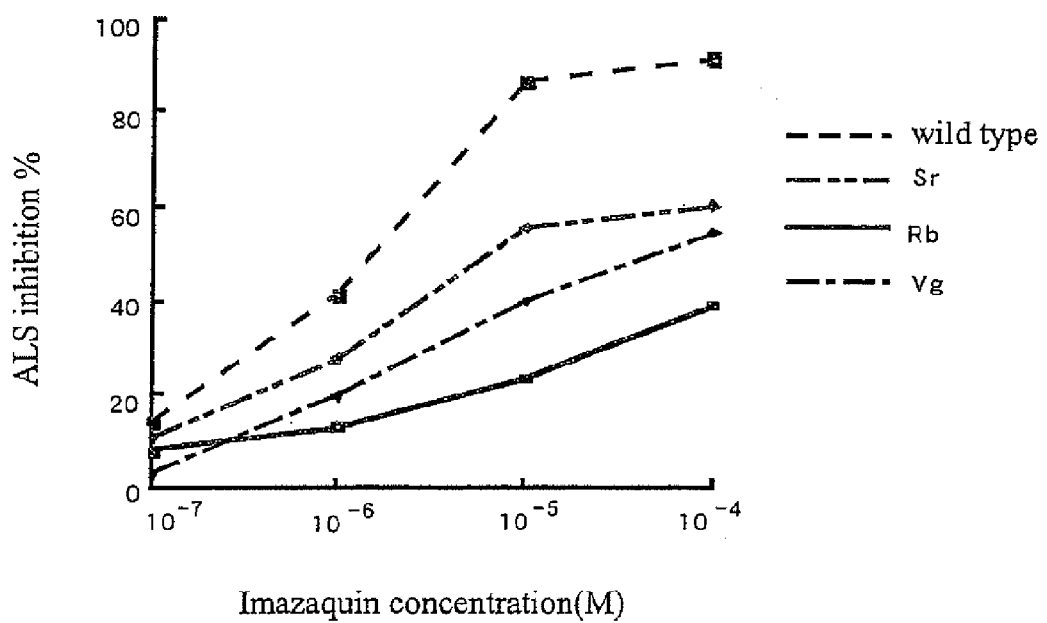
FIG. 17 is a characteristic figure showing sensitivity of the wild type ALS protein and the mutant ALS protein to imazaquin.

FIG. 15 shows the relation between ALS activity inhibition rate and bispyribac-sodium concentration. FIG. 16 shows the relation between ALS activity inhibition rate and chlorsulfuron concentration. FIG. 17 shows the relation between ALS activity inhibition rate and imazaquin concentration. In these FIGS. 15 to 17, a dotted line denotes the wild type ALS protein, a long dashed double-dotted line denotes Sr line of the mutant ALS protein, a solid line denotes Rb line of the mutant ALS protein, and a long dashed dotted line denotes Vg line of the mutant ALS protein.

A herbicide concentration which inhibits 50% of ALS activity (I50) was found from calculation according to probit analysis, thereby calculating the ratio of I50 for the mutant ALS protein vs. I50 for the wild type ALS protein. Table 4 shows the results.

TABLE 4

| Herbicide | I$_{50}$ (nM) | | | |
|---|---|---|---|---|
| | Wild type | Vg | Sr | Rb |
| Bispyribac-sodium | 5.63 | 97.2 | 421 | 247000 |
| Chlorsulfuron | 17.3 | 495 | 92.8 | 32000 |
| Imazaquin | 1480 | 44100 | 16700 | 609000 |

Further, based on the results in Table 4, I50 of the resistant mutant against each herbicide was divided by I50 of the wild type to work out RS. The results are shown in Table 5.

TABLE 5

| Herbicide | RS ratio | | |
|---|---|---|---|
| | Vg | Sr | Rb |
| Bispyribac-sodium | 17.3 | 74.8 | 43900 |
| Chlorsulfuron | 28.6 | 5.36 | 1850 |
| Imazaquin | 29.8 | 11.3 | 411 |

As shown in FIGS. 15 to 17 and Tables 4 and 5, the mutant ALS protein showed a relatively high ALS activity even in the presence of the herbicide, when compared to the wild type ALS protein. In particular, the mutant ALS proteins derived from Rb line and Sr line were shown to have sensitivity to bispyribac-sodium which was significantly superior to sensitivities to other herbicides. That is, Rb and Sr lines possess good resistance to bispyribac-sodium in particular.

Example 3

Cloning of Wild Type and Mutant ALS Genes

In this example, a gene (wild type ALS gene) coding for the wild type ALS protein was cloned from the wild type, while a gene (mutant ALS gene) coding for the mutant ALS protein was cloned from the resistant mutant.

Probes used for cloning the wild type ALS gene and the mutant ALS gene were prepared as follows. The partial cDNA derived from rice (Nippon-bare) showing high homology with the ALS gene of maize was used as a probe in this example.

(1) Determination of the Nucleotide Sequence of a Partial cDNA Derived From Rice (Nippon-bare) Showing High Homology With the ALS Gene of Maize As a part of the Rice Genome Project conducted by the Society for Techno-innovation of Agriculture, Forestry and Fisheries, and the National Institute of Agrobiological Sciences, partial nucleotide sequences of cDNAs of rice (Nippon-bare) had been determined and a partial nucleotide sequence database of cDNAs had already been established. A cDNA clone (Accession No. C72411) which is known as a nucleotide sequence of approximately 350 bp contained in this database showed high homology to the ALS gene of maize. The ALS gene of maize had been completely sequenced.

This cDNA clone (Accession No. C72411) was obtained from the National Institute of Agrobiological Sciences, and the nucleotide sequence was determined as follows. Here, the cDNA clone comprised an ALS homolog gene inserted within pBluescript II SK+, and it was capable of autonomous replication in *E. coli*.

First, an ALS homolog-retaining plasmid vector was transformed into *E. coli* (DH5α). White colonies obtained from a plate were cultured in liquid, and then plasmids were extracted from the cells by standard techniques. Since the insert DNA had been inserted between Sal I and Not I (restriction enzymes of multi-cloning sites in the plasmid vector), the vector was digested with the two enzymes. The insert was confirmed by agarose electrophoresis. Then, the obtained ALS homolog-retaining plasmid vector was purified by standard techniques using, e.g., RNaseA, PEG and LiCl, followed by sequencing reaction using primers and an ABI BigDyeTerminator Cycle Sequencing Kit. Conditions for PCR reaction followed the manufacturer's protocols. Primers used herein were M13 primers and synthesized primers designed from the determined nucleotide sequence. The resulting PCR product was purified by ethanol precipitation, and then the nucleotide sequence thereof was determined by an ABI PRISM 310 sequencer.

The ALS homolog-retaining plasmid vector is known to contain an insert DNA with a length of 1.6 kb. The obtained ALS homolog-retaining plasmid vector was digested with restriction enzymes Sal I and Not I, and then subjected to electrophoresis. As a result, a band of approximately 3 kbp corresponding to pBluescript II SK+ and a band of approximately 1.6 kbp corresponding to the insert DNA fragment were detected (data not shown). The entire nucleotide sequence of the insert DNA portion was determined, and its homology to the nucleotide sequence of maize was searched. As shown in FIGS. 18A and B, 84.7% homology was found. Since the ALS homolog was determined to be a partial cDNA of the ALS gene of the var. Nippon-bare, the insert DNA excised after digestion with Sal I and Not I was used as a probe. Further in FIGS. 18A and B, the first row is a nucleotide sequence of the cDNA of the ALS gene of the var. Nippon-bare; the second row is that of the ALS gene of maize.

(2) Preparation of mRNA From Resistant Mutant and Wild Type

First, the resistant mutant frozen with liquid nitrogen was crushed with a mortar and pestle, and then finely crushed with a mixer for 30 seconds. The crushed powder was suspended in an extraction buffer [(100 mM Tris-HCl pH 9.0, 100 mM NaCl, 1 weight % SDS, 5 mM EDTA):(β-mercaptoethanol):(Tris saturated phenol)=15:3:20], and then stirred thoroughly. This solution was centrifuged at 12000×g for 15 minutes, and then the supernatant was collected. Two hundred ml of PCI [(Tris saturated phenol):(chloroform):(isoamylalcohol)=25:24:1] was added to the supernatant, shaken at 4° C. for 10 minutes, centrifuged at 12000×g for 15 minutes, and then the supernatant was collected. The procedure was repeated twice. A 1/20 volume of 5 M NaCl and a 2.2-fold volume of ethanol were added to the obtained supernatant, and then the mixture was allowed to stand at −80° C. for 30 minutes. The precipitate was collected by centrifugation at 12000×g for 5 minutes. The precipitate was washed with 70% ethanol, dried, and then dissolved in 10 mM β-mercaptoethanol solution. Next, the solution was centrifuged at 27000×g for 10 minutes to remove insoluble fraction. A ¼ volume of 10 M LiCl was added to the solution, which was then allowed to stand on ice for 1 hour. Further, the solution was centrifuged at 27000×g for 10 minutes to collect precipitate, dissolved in 4 ml of H$_2$O, and then absorbance at 260 nm was measured to find the concentration of RNA. A 1/20 volume of 5 M NaCl and a 2.2-fold volume of ethanol were added to the solution, which was then allowed to stand at −80° C. for 30 minutes. Subsequently the solution was centrifuged at 27000×g for 10 minutes to collect the precipitate, followed by washing with 70% ethanol, and drying. The resulting product was dissolved in an appropriate amount of H$_2$O to obtain a total RNA solution. Here, centrifugation was performed at 4° C.

mRNA was separated and purified from total RNA by the following method. A 2× binding buffer (20 mM Tris-HCl (pH 7.5), 10 mM EDTA, 1 M NaCl) in a volume equivalent to that of the extracted total RNA solution was added to the extracted total RNA solution. A column filled with 0.1 g of oligo dT cellulose (Amersham Bioscience) was washed with a 1× binding buffer, and then the total RNA solution was applied to the column. After the column was washed with a 1× binding buffer, an elution buffer (10 mM Tris-HCl (pH 7.5), 5 mM EDTA) was applied, and the eluate collected 0.5 ml at a time. Fractions that had passed through the column were applied to another oligo dT cellulose (Amersham Bioscience) column, and treated in the same manner. After the concentration of eluted mRNA was calculated based on the absorbance of each fraction, a 1/10 volume of 10 M LiCl and a 2.5-fold volume of ethanol were added to the products, and then the mixtures were allowed to stand at −80° C. for 30 minutes. Next, the mixtures were centrifuged and the precipitated fractions were dried, and dissolved in 100 μl of H$_2$O. The thus obtained mRNA was subjected to size fractionation by sucrose density gradient centrifugation.

The separated and purified mRNA was applied to a centrifuge tube with density gradient given by a 25% sucrose solution and 5% sucrose solution, and then ultracentrifuged at 27000 rpm for 15 hours at 4° C. using a swing rotor. After centrifugation, 0.5 ml of each fraction was collected in order of density gradient. Absorbance of each fraction was measured, the concentration of the collected mRNA was calculated, and the presence of ALS mRNA was confirmed by hybridization using an ECL kit (ECL direct nucleic acid labeling and detection system, Amersham Bioscience). Hybridization was performed using a probe prepared in (1) above at 42° C. for 16 hours. After hybridization, washing at 42° C. for 5 minutes was performed twice using a primary washing buffer provided with the kit, and then washing at 42° C. for 5 minutes was performed once using 2×SSC solution. The washed film was wrapped with a transparent plastic film to keep it immersed in an attached luminous reagent provided with the kit, and then exposed to an X-ray film.

When Sr line was used as the resistant mutant, approximately 35 mg of total RNA and approximately 4 mg of mRNA could be extracted by the above procedures. Further, in sucrose density gradient centrifugation, a hybridization-positive spot was found for a fraction expected to be positive.

When the wild type was used, approximately 95 mg of total RNA was extracted in addition to approximately 7 mg of mRNA. When mRNA was extracted from the wild type, the above method was applied except that the wild type was used instead of the resistant mutant.

(3) Construction of cDNA Libraries Derived From Resistant Mutant and Wild Type

Using 2 μg of mRNA purified in (2) above and a cDNA synthesis kit (Amersham Bioscience), cDNA was synthesized, so that a cDNA library derived from the resistant mutant was constructed.

First, RTase provided with the kit was used for a reverse transcription reaction; and T4 DNA polymerase provided with the kit was used for a subsequent complementary chain elongation reaction. At the time of complementary chain elongation reaction, $^{32}$P-dCTP was added to calculate the yield of cDNA synthesis. After an adaptor was added, the synthesized cDNA was incorporated into λ phage by in vitro packaging method.

The adaptor added to cDNA was an Eco RI-Not I-Bam HI adaptor (Takara Shuzo). Adapters with a molar concentration 50-fold greater than that of cDNA were added to a solution containing cDNA. Then, T4 DNA Ligase (Pharmacia) was added to the mixture followed by ligation reaction at 4° C. overnight. The reaction solution was applied to HPLC using an AsahiPak GS 710 column (Asahi Chemical Industry Co., Ltd.), followed by monitoring of the eluate with ultraviolet rays at a wavelength of 260 nm. The eluate was fractionated into 25 fractions of 0.5 ml each. Each fraction was measured with a Cerenkov counter, and 3 to 4 fractions with a high count were collected. The 5' terminus of the adaptor contained in the fraction was phosphorylated using T4 polynucleotide kinase (Takara Shuzo), and then λgt 11 Eco RI arm was added to perform ligation. GigaPack Gold III (Stratagene) was added to the solution, and then ligation reaction was performed at room temperature for 2 hours. After reaction, 200 µl of an SM buffer and 8 µl of chloroform were added to the reaction solution, thereby preparing a phage solution. This phage solution was diluted 10-fold. One µl of the diluted solution was infected with $E.\ coli$ (Y-1088), to which 0.7% top agar was added, and then the solution was inoculated over an LB plate. The number of plaques that had appeared on the plate 4 to 8 hours later was counted, thereby measuring the titer.

Synthesis of approximately 74 ng of cDNA derived from Sr line was confirmed by the result of DE 81 paper and Cerenkov counting. The result of Cerenkov counting after ligation of a vector with an adaptor added thereto revealed that approximately 22 ng of λDNA contained the insert was obtained for Sr line. The λDNA was packaged into the phage, thereby preparing a cDNA library derived from the cells of the resistant mutant. The titer of the library solution was 16600 pfu/µl.

When a cDNA library was constructed using mRNA extracted from the wild type according to the above-described method, it was shown that approximately 38 ng of cDNA derived from the wild type had been synthesized. Further, approximately 5 ng of EDNA contained the insert was obtained for the wild type. Furthermore, the titer of the cDNA library solution derived from the wild type was 18160 pfu/µl.

(4) Screening of cDNA Containing the ALS Gene

To form about 20,000 plaques on plates, the library solution prepared in (3) above was diluted, and then phages derived from the wild type and those derived from Sr line were separately inoculated over 10 plates, respectively. Plaques were then transferred to a nitrocellulose membrane (Schleicher & Schnell, PROTORAN BA85, pore size 0.45 µm), and the nitrocellulose membrane was immersed in a denaturation solution (0.5 M NaOH, 1.5 M NaCl), and then in a neutralization solution (1.5 M NaCl, 0.5 M Tris-HCl (pH 7.5), 1 mM EDTA) for approximately 20 seconds. Excess water was removed from the nitrocellulose membrane using a filter paper, and then the nitrocellulose membrane was baked at 80° C. for 2 hours. Here, the baking step was omitted when Hybond-N+ (Amersham Biotech) was used instead of a nitrocellulose membrane, and immobilization was performed with 0.4 M NaOH for 20 minutes.

The insert DNA prepared in (1) above was labeled by two types of method, RI and non-RI, and then used as a probe DNA. Labeling with RI and hybridization were performed by the following method. First, approximately 200 to 500 ng of probe DNA was thermally denatured, and then labeled using a BcaBEST DNA labeling kit (Takara Shuzo). At the time of this labeling reaction, a buffer, random primers and $^{32}$P-dCTP provided with the kit were added. Next, BcaBEST was added, followed by incubation at 65° C. for 30 minutes. Subsequently, EDTA was added to stop the reaction. The reaction solution was applied to nitrocellulose membranes, so that 8 of the membranes contained approximately 100 ng of probes. Hybridization was performed at 42° C. overnight with weak shaking. After hybridization, the membranes were washed three times with 2×SSC, 0.1% SDS solution, followed by exposure for about I hour to an imaging plate of a BAS 2000 imaging analyzer (Fuji Photo Film). Following exposure, positive clones were detected using the imaging analyzer.

Labeling with non-RI was performed by the following method. Following thermal denaturation of approximately 200 to 500 ng of probe DNA, DNA labeling reagent (peroxidase) and glutaraldehyde which were provided with an ECL direct DNA/RNA labeling and detection system (Amersham Bioscience) were added, followed by incubation at 37° C. In this case, the labeled probe DNA was applied to nitrocellulose membranes, so that 8 of the membranes contained approximately 100 ng of the labeled probe DNA. Hybridization was performed at 42° C. overnight with weak shaking. After hybridization, the membrane was washed three times with a primary washing buffer at room temperature for 10 minutes, and then once with 2×SSC at room temperature for 10 minutes. The membrane was immersed in a luminous solution provided with the ECL kit, and then exposed to an X-ray film for 30 minutes to 3 hours.

Positive phages obtained by hybridization (primary screening) were scraped off together with top agar using a sterile toothpick, and then suspended in 200 µl of SM buffer, thereby obtaining a phage solution. Phage solutions of each clone were appropriately diluted, infected with $E.\ coli$ strain Y-1088, and then inoculated over LB plates. Using these newly prepared plates, hybridization (secondary screening) was performed similarly. Positive phages were suspended in 200 µl of a SM buffer, thereby obtaining single phages. If no single phage was isolated by secondary screening, another dilution was performed, followed by inoculation over LB plates. Subsequently, hybridization (the third screening) was performed, so that single phages were obtained.

Next, λDNA was prepared from the single phages by the following methods. λ phages collected with a bamboo brochette or a toothpick from plaques of positive clones were inoculated in 200 µl of a 2×YT medium (containing 10 mM $MgCl_2$ and 0.2% maltose) containing 5 µl of a suspension of fresh host $E.\ coli$ (Y1088). The product was allowed to stand and incubated at 42° C. overnight. Then, the medium was inoculated again in 1 ml of a 2×YT medium (containing 10 mM $MgCl_2$ and 0.2% maltose) containing 25 µl of a suspension of host $E.\ coli$ (Y1088), and then shake-cultured overnight (these steps compose a pre-culturing process). The pre-cultured solution (10 to 50 µl) was inoculated in 12 ml of 2×YT medium containing 10 mM $MgCl_2$ and 0.5 ml of $E.\ coli$ Y1088 suspension. Then, incubation was performed at 42° C. overnight with relatively strong shaking, until turbidity increased after lysis. After culturing, 50 µl of chloroform and 1.2 ml of 5 M NaCl were added, and then incubation was performed at 42° C. for 10 minutes while shaking. The product was centrifuged at 27000×g for 10 minutes, and then the supernatant was newly transferred to a centrifugation tube. Five ml of 50% PEG was added to the supernatant, and then incubated on ice for 1 hour or more. The product was centrifuged at 27000×g for 10 minutes, and then the supernatant was discarded. Next, another centrifugation was performed at 27000×g, and then the liquid portion was discarded. The precipitated fraction was suspended in 300 µl of a 30 mM Tris hydrochloric acid buffer (pH 7.5) containing 4 µg of DNase I, 20 µg of RNase A and 10 mM $MgCl_2$. The suspension was transferred to a 1.5 ml tube. After incubation of the suspension at 37° C. for 30 minutes, 7.5 µl of 20% SDS, 3 µl of proteinase K (10 mg/ml), and 12 µl of 0.5 M EDTA were added to the suspension, followed by further incubation at 55° C. for 15 minutes. Subsequently, 150 µl of phenol was added to the product, and then stirred vigorously. Then the mixture was centrifuged at 15000 rpm for 3 minutes using a TOMY Microcentrifuge MR-150 (TOMY DIGITAL BIOLOGY), and an aqueous layer was collected. 800 µl of ethyl ether (to which distilled water had been added to remove peroxide) was added to the collected aqueous layer. The mixture was stirred vigorously, and then centrifuged at 15000 rpm for 10 seconds and the ether layer was discarded. After the ether extraction step was repeated, ether remaining in the aqueous layer was removed with nitrogen gas. Thirty µl of 5 M NaCl and 875 µl of ethanol were added to the aqueous layer, so that precipitated λDNA was rapidly collected. The collected λDNA was rinsed with approximately 1 ml of 70% ethanol, and then dried under reduced pressure for approximately 1 minute, thereby removing ethanol. The product was dissolved in 20 µl to 50 µl of a TE buffer (pH 8.0), thereby preparing a λDNA solution.

Subcloning and sequencing of the insert DNA in the obtained λDNA were performed by the following method. The obtained λDNA solution (1 µl) was digested with Not I so as to excise the insert DNA. The composition of a reaction solution (for cleavage reaction) followed the procedure in the manual attached to the restriction enzyme. After reaction at 37° C. for approximately 2 hours, the insert size was confirmed by electrophoresis using 1% agarose gel. λDNA (10 µl to 20 µl) containing the insert DNA was digested with Not I, so as to excise the insert DNA. The insert DNA was separated using agarose gel for apportioning, the corresponding band was cleaved from the gel, and then the insert DNA was purified by standard techniques. The insert DNA was mixed with a vector following BAP treatment (dephosphorylation using alkaline phosphatase derived from a shrimp) at molar ratio of 1:1, followed by ligation reaction with T4 DNA ligase at 16° C. for 2 hours or more. Here, since the insert DNA cleaved with Not I was used as material, BAP treatment was performed for vectors cleaved with Not I. Following ligation, part of the solution was mixed with competent cells (DH5α), and then allowed to stand on ice for 30 minutes. Next, the mixture was subjected to heat shock at 42° C. for 30 seconds, and then allowed to stand on ice again for 2 minutes. Then, SOC was added to the mixture, incubated at 37° C. for 1 hour, inoculated over a LB medium plate on which a mixture of 100 µl of 2×YT (containing 50 µg/ml ampicillin), 30 µl of 3% X-Gal and 3 µl of 1 M IPTG had been previously added uniformly, and then cultured at 37° C. for 10 hours or more. The transformed white colonies were each inoculated on 2 ml of an LB medium containing ampicillin or a 2×YT medium, and then cultured at 37° C. overnight. From the culture solution, plasmids were prepared by standard techniques and dissolved in $H_2O$. The DNA concentration thereof was quantified, and then the plasmids were subjected to PCR reaction for sequencing. PCR reaction and sequencing were performed by methods described above.

As a result of the above experiment, the ALS cDNA with an incomplete length of approximately 2.2 kb was obtained from the culture cells of each wild type and Sr line. Since an Sma I site was present at a position approximately 250 bp from the 5' side of the DNA, a new probe was prepared by the following method. pBluescript II SK+ retaining the ALS cDNA with an incomplete length of approximately 2.2 kbp derived from the wild type was amplified with host $E. coli$ JM109, and then plasmids were extracted using an automated isolation system (KURABO PI-100). The plasmid was directly digested with Sma I. The generated fragment of approximately 250 bp was separated and purified by 1% agarose electrophoresis, and then the concentration was calculated, thereby preparing a probe. Using the probe, the library was screened again by the above method employing the above RI. λDNA was prepared from the thus obtained single phages, the λDNA solution (1 µl) was digested with Eco RI, and then size was confirmed by electrophoresis, followed by immobilization onto a nitrocellulose membrane. Following electrophoresis, the gel was immersed in 0.5 M NaOH solution containing 1.5 M NaCl, and then shaken lightly for 15 minutes. The gel was then washed with water, immersed in 0.5 M Tris-HCl (pH 7.5) containing 3 M NaCl, and then neutralized while shaking for approximately 15 minutes. Approximately 5 thick, industrial filter papers were piled up to make a base. The base was placed in 20×SSC spread over a stainless bat. Subsequently, the neutralized gel, a nitrocellulose membrane (which had been cut into a certain size, immersed in distilled water and then immersed in 20×SSC for another 10 minutes), and two-ply filter papers were placed in order on the base, on which a paper towel with a thickness of 3 cm to 4 cm was further placed. A glass plate and then a light weight were placed on the product, followed by blotting for approximately 5 minutes. After confirming that no bubbles were entrapped between the gel and the membrane, blotting was performed for approximately 10 minutes. Following blotting, the membrane was subjected to UV treatment with a trans-illuminator, and then baked at 80° C. for approximately 15 minutes to 30 minutes. After baking, hybridization (hybridization buffer composition: 5×SSPE, 0.5% SDS, 5×Denharlts, solum sperm DNA, 50% formamide) was performed with the above 250 bp probe DNA labeled with $^{32}P$. Radiation of the hybridized band was transferred to an imaging plate, and the result was analyzed with BAS-2000. Among inserts positive in hybridization, those showing a relatively large size were prepared in large quantity, and then sub-cloned into pBluescript II SK+ that had been digested with Eco RI and then treated with BAP by the above method. The product was transformed into $E. coli$ (JM 105). The obtained transformants were subjected to liquid culture, and then plasmids were prepared by standard techniques. Thus, the nucleotide sequence was determined by the above methods.

As a result, the full-length ALS cDNA gene could be obtained from the culture cells of each wild type and Sr line. The results of homology comparisons between the wild type and the mutant ALS genes are shown in FIGS. 19A, B and C. As shown in FIGS. 19A, B, and C, compared to the wild type, 2-point mutations were observed in Sr line at 2 points, the 1643rd and $1880^{th}$, from the first base A as the starting point of the transcription initiation codon ATG. In Sr line, the 1643rd G in the wild type was mutated to T (denoted as G1643T), and the 1880th G in the wild type was mutated to T (denoted as G1880T). When converted into amino acids, these mutations indicated that the mutant ALS protein of Sr line had an amino acid sequence wherein the 548th tryptophan in the wild type ALS protein was mutated to leucine (that is, "W548L mutation"), and the 627th serine in the wild type ALS protein was mutated to isoleucine (that is, "S627I mutation").

(5) Subcloning of the Wild Type ALS cDNA Cloned into pBluescript II SK+ into pGEX 2T After the pBluescript II SK+ plasmid having the full-length wild type ALS cDNA obtained in (4) above incorporated therein was digested with Eco RI, cDNA containing the wild type ALS gene was excised. Then, the cDNA was incorporated into Eco RI site of pGEX-2T (Amersham Bioscience), which is an $E. coli$ expression vector. Hereinafter, an expression vector having the full-length wild type ALS cDNA incorporated into the Eco RI site of pGEX-2T is referred to as "pGEX-2T(ALS-wild)." pGEX-2T(ALS-wild) was transformed into *E. coli* (JM 109). Colonies obtained by transformation were liquid-cultured, plasmids were extracted, and then the insertion direction of insert DNA was confirmed by sequencing. Thus, *E. coli* (JM 109) transformed with pGEX-2T(ALS-wild) was prepared.

Example 4

Elucidation of Mutation Sites in ALS Gene of PC Herbicide Resistant Rice Culture Cell (1) Extraction of Genomic DNA From Resistant Mutant (Strains of Sr, Rb, Vg, and Ga Lines)

Using a plant DNA extraction kit ISOPLANT II (Nippon Gene), genomic DNA was extracted from 0.1 g of cultured cells of each of Sr, Rb, Vg and Ga lines according to the protocols attached to the kit. After genomic DNA was extracted using the above kit, RNA was denatured and removed using RNase A. Then, agarose gel electrophoresis was performed, thereby confirming the genomic DNA.

(2) PCR of ALS Gene Using Genomic DNA as Template

PCR was performed using each genomic DNA as a template, and a primer "ALS-Rsp3" and a primer "4-83-3," as shown below. PCR was performed using Ready to Go PCR Beads (Amersham Bioscience) at a final volume of 25 µl. The reaction was performed for 40 cycles, each cycle condition consisting of an initial denaturation step at 94° C. for 5 minutes, followed by a denaturation step at 94° C. for 30 seconds, annealing step at 55° C. for 1 minute, and elongation step at 72° C. for 2 minutes. In addition, the elongation step in the final cycle was performed at 72° C. for 9 minutes.

Next, the PCR reaction solution was subjected to 2% agarose gel electrophoresis (100V, 1×TBE buffer). Gels containing PCR products were excised, and then excised gels were cut into small fragments. The obtained gel fragments were rinsed twice or three times with sterile ion exchanged water, 500 µl of sterile ion exchanged water was added, and then freezing and dissolving was repeated three times. Thus, the PCR product could be eluted in water.

Next, PCR was performed again using the eluate in which the PCR product had been dissolved. Specifically, this PCR was performed at a final volume of 100 µl using the PCR product contained in the solution as a template, and the same primer set or nested primers. After reaction, the reaction solution was subjected to agarose gel electrophoresis (1%) for apportioning. Gels containing target bands were excised, and then purified using a GFX PCR DNA & Gel Band Purification Kit (Amersham Bioscience). Finally, the PCR product was eluted using 75 µl of sterile deionized water.

(3) Sequencing

Sequence reaction was performed using the DNA fragment amplified by PCR as a template and ABI PRISM BigDye ver.2 (Applied Biosystem). For sequence reaction, 11 µl of the template DNA, 1 µl of the primer (3.2 pmol/µl) and 8 µl of pre-mix was mixed, therefore the total volume was 20 µl. The sequence reaction was performed for 40 cycles, each cycle condition consisting of an initial denaturation step at 96° C. for 5 minutes, followed by a denaturation step at 96° C. for 5 seconds, annealing step at 50° C. for 5 seconds, and elongation step at 60° C. for 4 minutes. In addition, the elongation step of the final cycle was performed at 60° C. for 9 minutes. After sequence reaction, fluorescent nucleotides in the reaction solution were removed by gel filtration using AutoSeq G-50 column (Amersham Biotech). Then the nucleotide sequences were read using ABI PRISM 310 DNA sequencer.

(4) Names of Primers and Nucleotide Sequences Used Herein

Names, nucleotide sequences and the like of primers used in (2) above and of primers used in the following examples are listed in Table 6.

TABLE 6

| SEQ ID NO | Name | Nucleotide sequence | Direction | Corresponding | Number of bases |
|---|---|---|---|---|---|
| 9 | ALS-Rsp1 | 5'-GCTCTGCTACAACAGAGCACA-3' | sense | 1192-1212 | 21 mer |
| 10 | ALS-Rsp2 | 5'-AGTCCTGCCATCACCATCCAG-3' | antisense | 1906-1926 | 21 mer |
| 11 | ALS-Rsp3 | 5'-CTGGGACACCTCGATGAAT-3' | sense | 720-738 | 19 mer |
| 12 | ALS-Rsp4 | 5'-CAACAAACCAGCGCAATTCGTCACC-3' | antisense | 862-886 | 25 mer |
| 13 | ALS-Rsp6 | 5'-CATCACCAACCACCTCTT-3' | sense | 327-344 | 18 mer |
| 14 | ALS-Rsp7 | 5'-AACTGGGATACCAGTCAGCTC-3' | antisense | 886-906 | 21 mer |
| 15 | ALS-RspA | 5'-TGTGCTTGGTGATGGA-3' | antisense | 571-586 | 16 mer |
| 16 | ALS-RspB | 5'-TCAAGGACATGATCCTGGATGG-3' | sense | 1913-1944 | 16 mer |
| 17 | ALS-RspC | 5'-CAGCGACGTGTTCGCCTA-3' | sense | 258-275 | 16 mer |
| 18 | ALS-RspD | 5'-CCACCGACATAGAGAATC-3' | antisense | 828-845 | 18 mer |
| 19 | ALS-RspF | 5'-ACACGGACTGCAGGAATA-3' | antisense | 1749-1766 | 18 mer |
| 20 | ALS-RspE | 5'-TTACAAGGCGAATAGGGC-3' | sense | 1656-1673 | 18 mer |
| 21 | 3-1-1 | 5'-GCATCTTCTTGATGGCG-3' | antisense | 1791-1807 | 17 mer |
| 22 | 3-1-2 | 5'-ATGCATGGCACGGTGTAC-3' | sense | 973-990 | 18 mer |
| 23 | 3-1-3 | 5'-GATTGCCTCACCTTTCG-3' | antisense | 1346-1362 | 17 mer |
| 24 | 3-1-4 | 5'-AGGTGTCACAGTTGTTG-3' | sense | 1506-1522 | 17 mer |

TABLE 6-continued

| SEQ ID NO | Name | Nucleotide sequence | Direction | Corresponding | Number of bases |
|---|---|---|---|---|---|
| 25 | 4-83-1 | 5'-AGAGGTGGTTGGTGATG-3' | antisense | 327-343 | 17 mer |
| 26 | 4-83-3 | 5'-GCTTTGCCAACATACAG-3' | antisense | 1944-1960 | 17 mer |
| 27 | 4-83-10 | 5'-CAGCCCAAATCCCATTG-3' | antisense | 1457-1473 | 17 mer |
| 28 | 4-83-15 | 5'-ATGTACCCTGGTAGATTC-3' | antisense | 735-752 | 18 mer |
| 29 | ALS-DG7 | 5'-GTITT(CT)GCITA(CT)CCIGG(ACGT)GG-3' | sense | 265-284 | 20 mer |

In Table 6, the corresponding ALS site is the number of a corresponding base when a transcription initiation codon (ATG) is the starting point. In addition, the nucleotide sequence of ALS-Rsp1 is shown in SEQ ID NO: 9, the nucleotide sequence of ALS-Rsp2 is shown in SEQ ID NO: 10, the nucleotide sequence of ALS-Rsp3 is shown in SEQ ID NO: 11, the nucleotide sequence of ALS-Rsp4 is shown in SEQ ID NO: 12, the nucleotide sequence of ALS-Rsp6 is shown in SEQ ID NO: 13, the nucleotide sequence of ALS-Rsp7 is shown in SEQ ID NO: 14, the nucleotide sequence of ALS-RspA is shown in SEQ ID NO: 15, the nucleotide sequence of ALS-RspB is shown in SEQ ID NO: 16, the nucleotide sequence of ALS-RspC is shown in SEQ ID NO: 17, the nucleotide sequence of ALS-RspD is shown in SEQ ID NO: 18, the nucleotide sequence of ALS-RspF is shown in SEQ ID NO: 19, the nucleotide sequence of ALS-RspE is shown in SEQ ID NO: 20, the nucleotide sequence of 3-1-1 is shown in SEQ ID NO: 21, the nucleotide sequence of 3-1-2 is shown in SEQ ID NO: 22, the nucleotide sequence of 3-1-3 is shown in SEQ ID NO: 23, the nucleotide sequence of 3-1-4 is shown in SEQ ID NO: 24, the nucleotide sequence of 4-83-1 is shown in SEQ ID NO: 25, the nucleotide sequence of 4-83-3 is shown in SEQ ID NO: 26, the nucleotide sequence of 4-83-10 is shown in SEQ ID NO: 27, the nucleotide sequence of 4-83-15 is shown in SEQ ID NO: 28, and the nucleotide sequence of ALS-DG7 is shown in SEQ ID NO: 29.

(5) Mutations in Each Line Revealed as a Result of Sequencing

As a result of analysis of nucleotide sequences determined in (3) above, mutations in Rb, Vg, Ga, and Sr lines were revealed. The mutated points of each line are listed in Table 7.

TABLE 7

| | Mutant base | | | |
|---|---|---|---|---|
| Mutant amino acid | C512A P171H | C514A R172S | G1643T W548L | G1880T S627I |
| Rb line | homo | | hetero | |
| Vg line | | | hetero | |
| Ga line | homo or hetero | homo or hetero | hetero | |
| Sr line | | | hetero | hetero |

As shown in Table 7, in the nucleotide sequence of Rb line strain, the $512^{nd}$ C was mutated to A (homo), and the $1643^{rd}$ G was mutated to T (hetero). This means that at the amino acid level, the $171^{st}$ proline and the $548^{th}$ tryptophan (W) were mutated to histidine (H) and leucine (L), respectively. In the nucleotide sequence of Vg line strain, the $1643^{rd}$ G was mutated to T (hetero), suggesting that at the amino acid level, the $548^{th}$ tryptophan (W) was mutated to leucine (L). In the nucleotide sequence of Ga line strain, the $512^{nd}$ and $514^{th}$ C were mutated to A (homo or hetero) (these types differed depending on the PCR product obtained), and the $1643^{rd}$ G was mutated to T (hetero). This means that at the amino acid level, the $171^{st}$ proline (P), $172^{nd}$ arginine (R) and $548^{th}$ tryptophan (W) were mutated to histidine (H), serine (S) and leucine (L), respectively. Further, in the nucleotide sequence of Sr line strain, the $1643^{rd}$ and $1880^{th}$ G were mutated to T (hetero).

When ALS genes were screened and isolated from the cDNA library of Sr line strain by the above method, not only a 2-point mutant gene, but also a gene of the wild type was isolated. Thus, it was assumed that at the genomic DNA level, heterologous mutation had occurred, and the results obtained by genome PCR also supported this assumption.

As described above, in all the resistant mutants, the $548^{th}$ tryptophan (W) was mutated to leucine (L) (hetero), and Vg line had this mutation only. As described above, Vg line strain showed sensitivity up to 10 µM bispyribac-sodium, and Sr, Rb and Ga line strains showed the same up to 100 µM bispyribac-sodium. Accordingly, it was suggested that the acquisition of resistance started from Vg line and branched into other lines and mutated, as the intensity of the selection pressure increased.

Example 5

Figure 20:
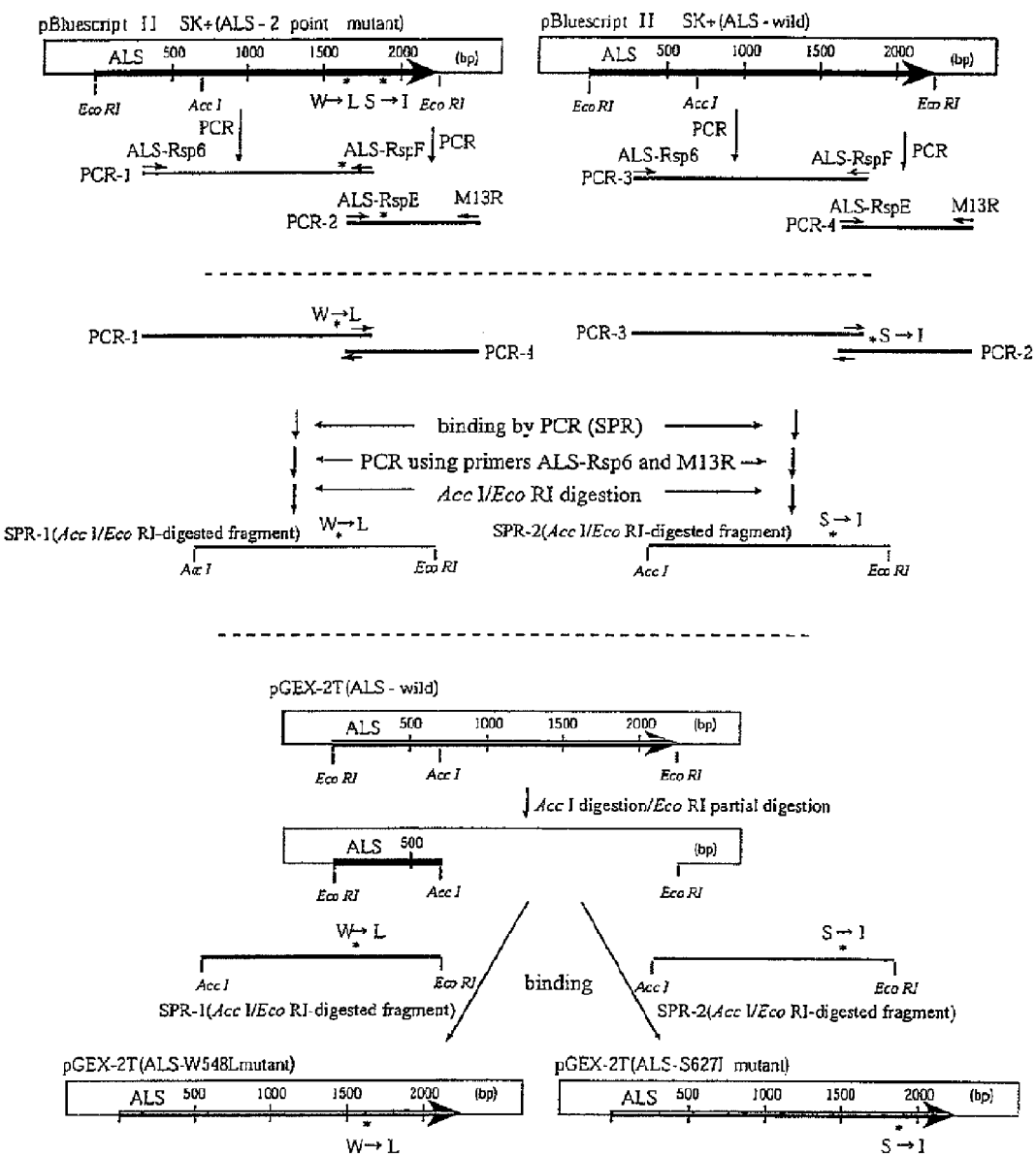
FIG. 20 shows processes for synthesizing ALS cDNAs independently having G1643T (W548L) mutation or G1880T (S627I) mutation, and for constructing pGEX 2T retaining the ALS cDNA. Arrows denote primers, and asterisks denote mutated points.

Synthesis of ALS cDNAs Independently Having G1643T(W548L) Mutation or G1880T(S627I) Mutation, Construction of pGEX 2T Retaining the ALS cDNAs, and Transformation of E. coli Using the Vector First, synthesis of ALS cDNAs independently having G1643T(W548L) mutation or G1880T(S627I) mutation, and construction of pGEX 2T retaining the ALS cDNAs are described using FIG. 20.

PCR was performed at a final reaction volume of 100 µl using 1 µl (585 ng/µl and 554 ng/µl, respectively) of pBluescript II SK+(ALS-2 point mutant) or pBluescript II SK+(ALS-wild) as a template, and 1 µl of LA Taq DNA polymerase (Takara). The reaction was performed for 25 cycles, each cycle condition consisting of 95° C. for 30 seconds, 55° C. for 30 seconds and 72° C. for 2 minutes. Further, pBluescript II SK+(ALS-2 point mutant) contained 2-point mutant ALS gene, G1643T(W548L) and G1880T(S627I). pBluescript II SK+(ALS-wild) contained the wild type ALS gene having no mutation. For the PCR, a combination of ALS-Rsp6 and ALS-RspF primers and a combination of ALS-RspE and M13R primers were used. Names of fragments amplified using ALS genes as a template and the given combination of primers are listed in Table 8. In addition, primer M13R is an antisense primer in the vicinity of T3 promoter of pBluescript II SK+. Further, the nucleotide sequence of M13R is 5'-GGAAACAGCTATGACCATG-3' (SEQ ID NO: 30).

TABLE 8

|  | pBluescript II SK+(ALS-2 point mutant) | pBluescript II SK+(ALS-wild) |
|---|---|---|
| ALS-Rsp6 ALS-RspF | PCR-1 | PCR-3 |
| ALS-RspE M13R | PCR-2 | PCR-4 |

PCR-1, PCR-2, PCR-3 and PCR-4 obtained by PCR were respectively subjected to agarose gel electrophoresis for separation, and then the products were collected in a manner similar to the above method from the agarose gel, and then the products were eluted with 50 μl of sterilized water.

Next, a set of PCR-1 and PCR-4, and a set of PCR-2 and PCR-3 were subjected to SPR (self polymerase reaction). SPR was performed by adding 23.5 μl of the set of PCR-1 and PCR-4, or the set of PCR-2 and PCR-3 and 1 μl of LA Taq DNA polymerase to a final volume of 75 μl, and by performing 25 times a cycle consisting of a denaturation step at 95° C. for 1 minute, annealing step at 55° C. for 30 seconds, and elongation step at 72° C. for 2 minutes. DNA fragments obtained by SPR using the set of PCR-1 and PCR-4 was regarded as SPR-1, and DNA fragments obtained by SPR using the set of PCR-2 and PCR-3 as SPR-2.

Further, in this example, to secure a sufficient amount of SPR-1 and of SPR-2, PCR was respectively performed at a final reaction volume of 100 μL using purified SPR-1 or SPR-2 as a template, ALS-Rsp6 and M13R, and LA Taq DNA polymerase again. PCR in this case was performed by repeating 25 times a cycle consisting of a denaturation step at 95° C. for 30 seconds, annealing step at 55° C. for 30 seconds and elongation step at 72° C. for 2 minutes. After PCR, the reaction solution was subjected to agarose gel electrophoresis. An approximately 2 kbp single band (PCR product) was collected from agarose gel, and then eluted with 100 μl of sterilized water.

Next, SPR-1 and SPR-2 amplified by PCR were respectively digested with Acc I and Eco RI, thereby obtaining SPR-1 (Acc I/Eco RI-digested fragment) and SPR-2 (Acc I/Eco RI-digested fragment). Specifically, 50 μl of the sterilized water (100 μl in total) containing PCR product dissolved therein was mixed with 1 μl of Acc I (12 u/μl) and 1 μl of Eco RI (12 u/μl) in the presence of 10×M buffer (Takara), followed by incubation at a final volume of 60 μl at 37° C. for 1 hour. Afterwards, the total volume of the reaction solution was subjected to agarose gel electrophoresis, and then a target 1.5 kbp fragment was collected using a GFX PCR and Gel Purification Kit. The collected 1.5 kbp fragment was eluted with 50 μl of sterilized water, so that a solution containing SPR-1 (Acc I/Eco RI-digested fragment) and a solution containing SPR-2 (Acc I/Eco RI-digested fragment) were prepared.

Meanwhile, 150 μl of a protein expression vector having the wild type ALS gene incorporated therein, pGEX-2T (ALS-wild) plasmid (concentration of approximately 50 ng/μl), was mixed with 1 μl of Acc 1 (12 u/μl, Takara) in the presence of 10×M buffer, followed by incubation at 37° C. for 2 hours. After reaction, a linear 7.2 kbp band was confirmed by 1% agarose gel electrophoresis. According to the protocols of GFX PCR and Gel Purification Kit, DNA corresponding to the 7.2 kbp band was collected from the agarose gel, and then the product was eluted with 180 μl of sterilized water. 89 μl of the eluted product was mixed with 10 μl of 10×H buffer (Takara) and 1 μl of Eco RI (12 u/μl), and then allowed to react at 37° C. for 1 minute, thereby partially digesting the thus collected DNA with Eco RI. After reaction, 10× loading buffer was added, and then 1.5% agarose gel electrophoresis was performed. 4.9 kbp, 5.7 kbp, and 6.5 kbp bands, and a 7.2 kbp band that was not cleaved at all appeared separately, and then the target 5.7 kbp band was excised from the gel. An approximately 5.7 kbp DNA fragment contained in the excised gel was collected using GFX PCR and Gel Purification Kit, and then the product was eluted with 50 μl of sterilized water.

Subsequently, 3 μl of fragments digested with Acc I and partially digested with Eco RI of the thus obtained pGEX-2T (ALS-wild) and 3 μl of SPR-1 (Acc I/Eco RI-digested fragment) or SPR-2 (Acc I/Eco RI-digested fragment) were respectively allowed to react in 6 μl of Takara ligation buffer (ver. 2, solution 1) at 16° C. overnight.

Then, the reaction solution was transformed into E. coli competent cells (strain JM109, Takara) according to the protocols attached thereto. The cells were inoculated on LB medium containing 50 ppm of ampicillin, and then incubated at 37° C. overnight. As a result, several of the colonies that appeared were selected. PCR was directly performed using the colonies as a template, and the set of ALS-RspE described in Table 6 and PGEX-3 (5'-CCGGGAGCTGCATGTGTCA-GAGG-3': SEQ ID NO: 31), the set of PGEX-5 (5'-GGGCTGGCAAGCCACGTTTGGTG-3': SEQ ID NO: 32) and PGEX-3, and the set of PGEX-5 and ALS-RspA described in Table 6. In addition, PGEX-3 had a sequence the same as a part of an antisense strand located on the 3' side of pGEX-2T used as a vector. PGEX-5 had a sequence the same as a part of a sense strand located on the 5' side of pGEX-2T used as a vector. As the reaction condition for the ALS-RspE/PGEX-3 set, each 1 μM primer and 1 PCR bead were dissolved in a total volume of 25 μl, and reaction was performed by repeating 40 times a cycle consisting of a denaturation step at 95° C. for 30 seconds, annealing step at 55° C. for 1 minute, and elongation step at 72° C. for 2 minutes. In the case of the PGEX-5/PGEX-3 set and PGEX-5/ALS-RspA set, DMSO with a final concentration of 5% was further added to the above solution, because of the presence, at an upstream portion, of a region having approximately 75% of GC content. As a result of this PCR, insertion of a desired insert was confirmed.

A colony for which the insertion of a desired insert had been confirmed was picked up, and then shake-cultured in LB liquid medium (3 ml each, 10 medias) containing 50 ppm of ampicillin at 37° C. for 12 hours. After culturing, plasmids were extracted (400 to 500 μl) from the media using a plasmid extraction system (TOMY, DP-480), and then concentrated to approximately 200 μl by centrifugation. Then, the concentrate was purified and desalted using GFX PCR and Gel Purification Kit, and then finally eluted with approximately 130 μl of sterilized water.

Sequence reaction was performed using ABI PRISM Big-Dye ver. 2 for these plasmids, so that the nucleotide sequence of the insert in the plasmid was analyzed. For sequence reaction, the reaction solution was prepared to have a total volume of 20 μl by mixing 11 μl of template DNA, 1 μl of primer (3.2 pmol/μl) and 8 μl of pre-mix. The sequence reaction was performed for 40 cycles, each cycle condition consisting of an initial denaturation step at 96° C. for 5 minutes, denaturation step at 96° C. for 5 seconds, annealing step at 50° C. for 5 seconds, and elongation step at 60° C. for 4 minutes, and the elongation step of the final cycle was performed at 60° for 9 minutes. After sequence reaction, fluorescent nucleotides in the reaction solution were removed by gel filtration using AutoSeq G-50 column, and then the nucleotide sequence was determined using ABI PRISM 310 DNA sequencer.

In addition, for sequence reaction, of the primers described in Table 6, PGEX-5, ALS-RspC, ALS-Rsp3, ALS-Rsp1, 3-1-4 and ALS-RspB were used as sense primers, and 4-83-3, PGEX-3, ALSRsp2, 4-83-10 and ALS-Rsp7 were used as antisense primers.

As a result of analysis, it was confirmed that pGEX 2T vector comprising the mutant ALS gene with W548L mutation (described as "pGEX 2T(ALS-W548L mutant)" in FIG. 20) and pGEX 2T vector comprising the mutant ALS gene with S627I mutation (described as "pGEX 2T(ALS-S627I mutant)" in FIG. 20) were obtained. Subsequently, E. coli was transformed with these pGEX 2T(ALS-W548L mutant) and pGEX 2T(ALS-S627I mutant).

Example 6

Figure 21:
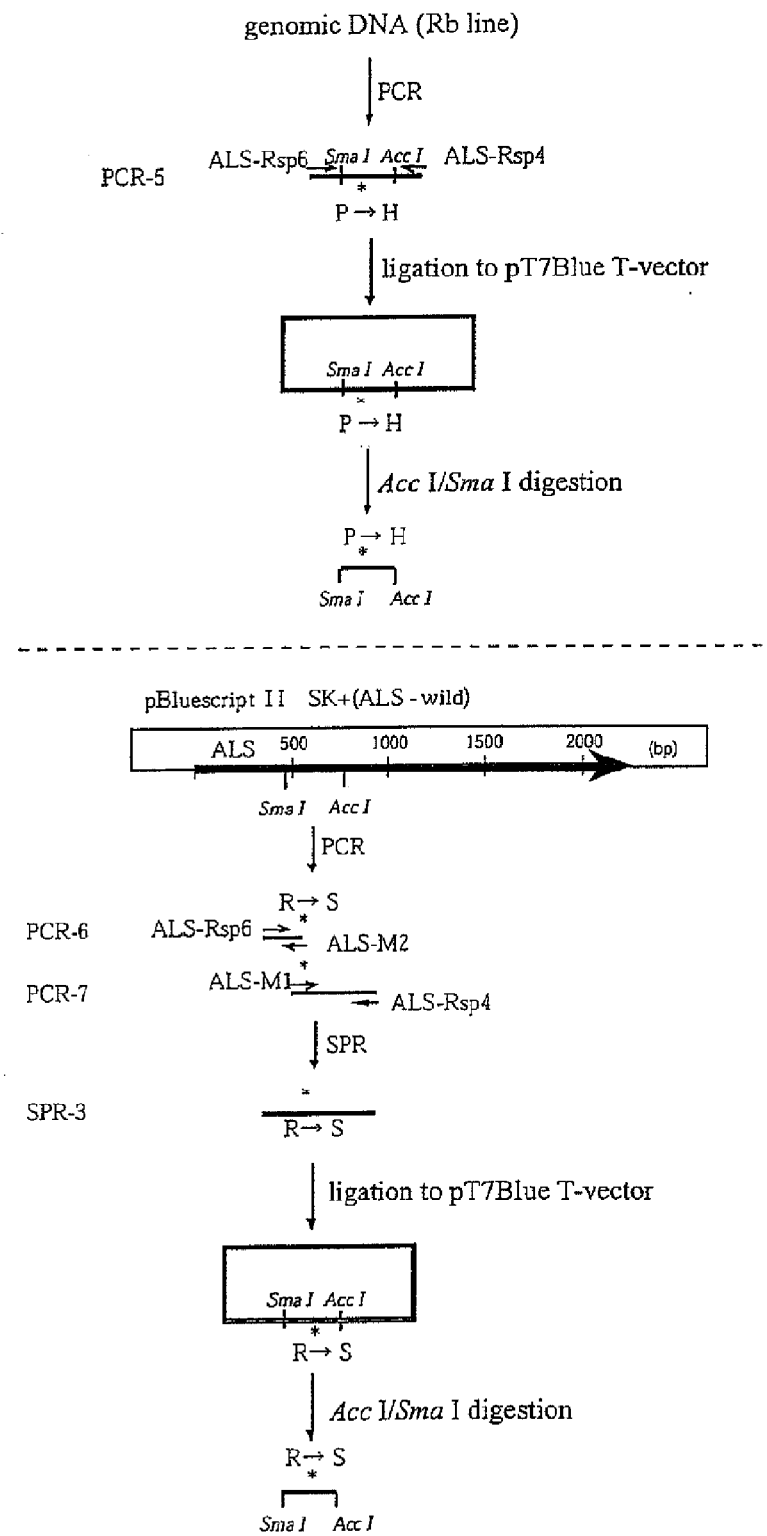
FIG. 21 shows a process for preparing C512A (P171H) mutant DNA fragment and C514A (R172S) mutant DNA fragment. Arrows denote primers, and asterisks denote mutated points.
Figure 2:
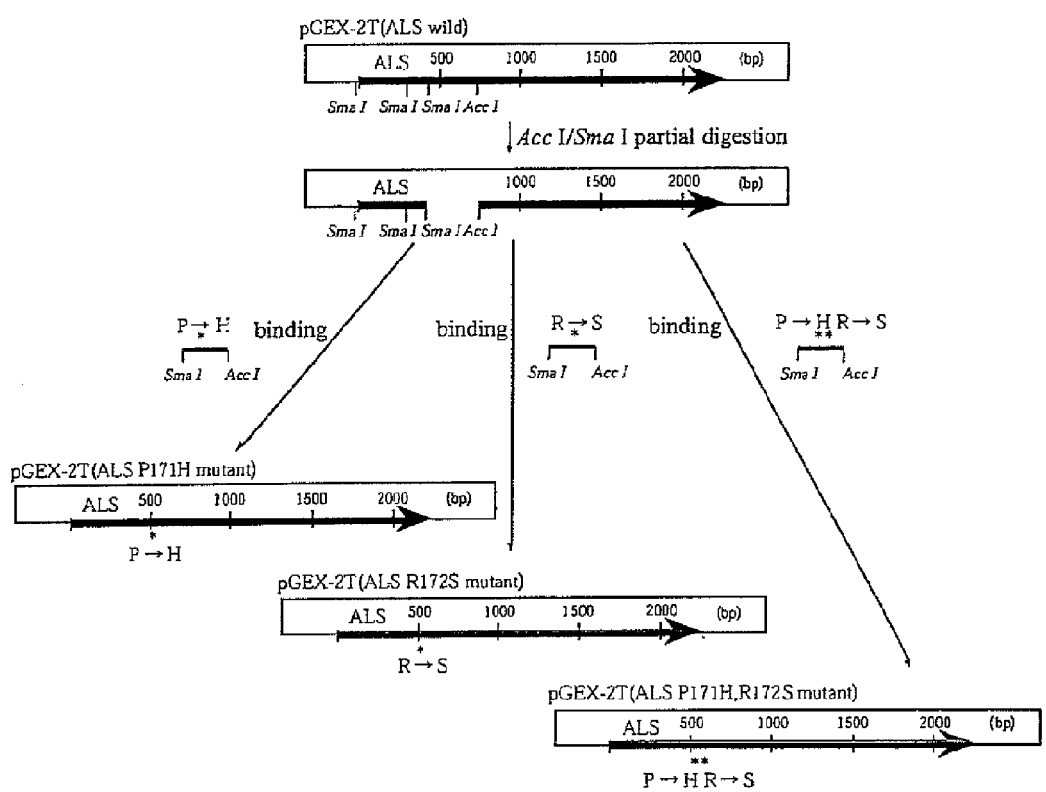
FIG. 2A shows a nucleotide sequence comparison between the mutant ALS genes (SEQ ID NOS: 1, 3, 5, 7) and the wild type ALS cDNA (SEQ ID NO: 38).
FIG. 2B is a continuation from FIG. 2A, and shows a nucleotide sequence comparison between the mutant ALS genes and the wild type ALS gene.
FIG. 2C is a continuation from FIG. 2B, and shows a nucleotide sequence comparison between the mutant ALS genes and the wild type ALS gene.
FIG. 2D is a continuation from FIG. 2C, and shows a nucleotide sequence comparison between the mutant ALS genes and the wild type ALS gene.

Synthesis of ALS cDNAs Independently Having C512A (P171H) Mutation Found by Genome PCR for Rb Line or C514A (R172S) Mutation Found by Genome PCR for Ga Line, Construction of pGEX 2T Retaining the ALS cDNAs, and Transformation of E. coli with this Vector First, the synthesis of ALS cDNAs independently having C512A (P171H) mutation and C514A (R172S) mutation, and construction of pGEX 2T retaining the ALS cDNAs are described using FIGS. 21 and 22.

To obtain C512A (P171H) mutant DNA fragment, PCR was performed using the genomic DNA of Rb line as a template and a primer set of ALS-Rsp6 and ALS-Rsp4 described in Table 6. Specifically, PCR was performed using Ready to Go PCR Beads by adding 5 µl of the template genomic DNA and 1 µl of each primer (25 pmol/µl) to a final volume of 25 µl. The reaction condition consisted of an initial denaturation step at 95° C. for 5 minutes, followed by a cycle (repeated 40 times) of a denaturation step at 95° C. for 30 seconds, annealing step at 55° C. for 1 minute, and elongation step at 72° C. for 2 minutes. In addition, the elongation step of the final cycle was performed at 72° C. for 9 minutes.

After PCR reaction, the reaction solution was subjected to 2% agarose gel electrophoresis, a band of the PCR product (described as "PCR-5" in FIG. 21) was excised from agarose gel, and then purified using GFX PCR DNA & Gel Band Purification Kit. Next, the purified PCR-5 was incorporated into pT7Blue T-vector (Novagen), the vector (TA cloning vector) for cloning PCR product. Specifically, 1 µl of the purified PCR product was mixed with 1 µl of pT7 Blue T-vector (50 ng/µl), 3 µl of sterile deionized water and 5 µl of ligation buffer (ver 2, solution T, Takara Shuzo), and then allowed to react overnight at 16° C.

After reaction, the total volume of the reaction solution was transformed into E. coli (strain JM109) according to standard methods. After culturing of E. coli on LB solid medium containing 50 ppm of ampicillin, the colonies having a target sequence was selected from the single colonies that appeared on the medium in a manner similar to Example 5. The selected single colonies were shake-cultured in LB liquid culture solution (3 ml, 10 media) containing 50 ppm of ampicillin at 37° C. for 12 hours. After culturing, plasmids were extracted (400 to 500 µl) using a plasmid extraction system (TOMY, DP-480). The plasmids were concentrated to approximately 200 µl by centrifugation, purified and desalted using GFX PCR and Gel Purification Kit, and then eluted with approximately 80 µl of sterilized water.

Fifty µl of the eluate was mixed with 1 µl of Acc I (12 u/µl) and 1 µl of Sma I (10 u/µl) in the presence of 10 µl of 10×T buffer and 10 µl of 0.1% BSA to bring to a total volume of 100 µl, and then the mixture was incubated at 37° C. for 2 hours. After reaction, the reaction solution was subjected to agarose gel electrophoresis, a target band was excised and collected, and then a DNA fragment was collected according to the protocols of GFX PCR and Gel Purification Kit. Thus, C512A (P171H) mutant DNA fragment having Sma I site and Acc I site on its termini was obtained.

On the other hand, since C514A and C512A mutations are close to each other, a DNA fragment having C514A (R172S) mutation only cannot be obtained by PCR using the genomic DNA extracted from Gb line as a template. Thus, as shown in FIG. 21, a DNA fragment having C514A (R172S) mutation only was prepared using a pair of primers to which mutated points had been previously introduced. That is, PCR was respectively performed using as primers having mutated points introduced therein ALS-M1 (5'-CCCCAGCCGCAT-GATCGGCACCGACGCCTT-3': SEQ ID NO: 33, underlined A is a mutated point) and ALS-M2 (5'-CGGTGCCGAT-CATGCGGCTGGGGACCT-3': SEQ ID NO: 34, underlined T is a mutated point) and as a template pBluescript II SK+having the wild type ALS cDNA incorporated therein; and using a primer set of ALS-Rsp6 and ALS-M2; and using a primer set of ALS-M1 and ALS-Rsp4. In addition, complementary portions are the nucleotide sequence ($1^{st}$ to $23^{rd}$ nucleotides) of ALS-M1 and that ($1^{st}$ to $23^{rd}$ nucleotides) of ALS-M2. When the primer set of ALS-Rsp6 and ALS-M2 were used, a DNA fragment described as "PCR-6" in FIG. 21 was amplified, and when the primer set of ALS-M1 and ALS-Rsp4 was used, a DNA fragment described as "PCR-7" in FIG. 21 was amplified.

The reaction solution was prepared at the time of PCR by dissolving 1 µl of LA Taq DNA polymerase (5 units/µl, TAKARA), 10 µl of 10×LA buffer, 10 µl of 25 mM $MgCl_2$, 16 µl of dNTPs (consisting of 25 mM of dATP, dGTP, dCTP and dTTP, respectively), 1 µl of template DNA, and 4 µl each of sense and antisense primers (25 pmol/µl, respectively) to a total volume of 100 µl. The reaction was performed by repeating 25 times a cycle consisting of an initial denaturation step at 95° C. for 5 minutes, a denaturation step at 95° C. for 30 seconds, annealing step at 55° C. for 1 minute, and elongation step at 72° C. for 2 minutes, and the elongation step in the final cycle was performed at 72° C. for 9 minutes.

After reaction, the reaction solution was subjected to 1.5% agarose gel electrophoresis for apportioning, target 213 bp (PCR-6) and 377 bp (PCR-7) bands were excised and purified using GFX PCR DNA & Gel Band Purification Kit, and then the thus generated DNA fragments were respectively eluted with 100 µl of sterile deionized water.

Next, SPR was performed using the thus obtained PCR-6 and PCR-7. At the time of SPR, a reaction solution was prepared to a total volume of 100 µl by mixing 30 µl of the thus obtained eluate with 1 µl of LA Taq DNA polymerase (5 units/µl), 10 µl of 10×LA buffer, 10 µl of 25 mM $MgCl_2$, and 16 µl of dNTPs (consisting of 25 mM of dATP, dGTP, dCTP and dTTP, respectively). SPR was performed by repeating 40 times a cycle consisting of an initial denaturation step at 95° C. for 5 minutes, a denaturation step at 95° C. for 30 seconds, annealing step at 55° C. for 1 minute, and elongation step at 72° C. for 2 minutes, and the elongation step in the final cycle was performed at 72° C. for 9 minutes.

After reaction, the reaction solution was subjected to agarose gel (1.5%) electrophoresis for apportioning, a target 560 bp band (described as "SPR-3" in FIG. 21) was excised and purified using GFX PCR DNA & Gel Band Purification Kit, and then the generated DNA fragment (SPR-3) was eluted with 100 µl of sterile deionized water. In a manner similar to the above method, the eluted fragment was incorporated into pT7Blue T-vector and then transformed into *E. coli* (JM109). The *E. coli* was cultured, and then the thus extracted plasmid was digested with Acc I and Sma I, thereby obtaining C514A (R172S) mutant DNA fragment having Sma I site and Acc I site at its termini.

Meanwhile, *E. coli* (strain JM109) transformed with pGEX-2T(ALS-wild), the plasmid having the wild type ALS gene incorporated therein, was shake-cultured in LB liquid medium containing 50 ppm of ampicillin (2 ml×15 media) overnight at 37° C. After the plasmid was extracted using a plasmid extraction system (DP-480), the extract (approximately 750 µl) was concentrated to approximately 200 µl using a vacuum centrifugation concentrator. Then, the concentrate was desalted using GFX PCR DNA & Gel Band Purification Kit, and then the plasmid was finally eluted with 200 µl of sterile deionized water.

Next, the thus obtained plasmid, pGEX-2T(ALS-wild), was digested with Acc I. Specifically, 75 µl of the eluate was mixed with 9 µl of 10×M buffer, 3 µl of Acc I (12 u/µl), and 3 µl of sterile deionized water, and then the mixture was allowed to react at 37° C. for 3 hours. After reaction, the reaction solution was subjected to 1.5% agarose gel electrophoresis for apportioning, the target band was excised and collected, and then purified using GFX PCR DNA & Gel Band Purification Kit, and then a DNA fragment was finally eluted with 100 µl of sterile deionized water.

Subsequently, pGEX-2T(ALS-wild) digested with Acc I was partially digested with Sma I. Specifically, 79 µl of the eluate was mixed with 10 µl of 10×T buffer, 10 µl of 0.1% BSA, and 1 µl of Sma I (10 u/µl) to a total volume of 100 µl, and then the mixture was incubated at 30° C. for 1 minute. In addition, since pGEX-2T(ALS-wild) contained Sma I recognition sequences (on the multicloning site adjacent to Thrombin cleavage site of pGEX-2T, $276^{th}$ and $430^{th}$ sequences of ALS gene) located at three positions separately, partial digestion was performed in a short time. After reaction, the reaction solution was subjected to agarose gel electrophoresis, a band corresponding to the plasmid wherein only the $430^{th}$ Sma I recognition sequence of ALS gene had been digested was excised and collected, and then purified using GFX PCR DNA & Gel Band Purification Kit to remove enzyme and protein. Finally, the purified product was eluted with 50 µl of sterile deionized water. This Acc I-digested/Sma I partially-digested pGEX-2T-wild type ALS cDNA fragment, C512A (P171H) mutant DNA fragment having Sma I site and Acc I site on its termini obtained by the above method, and C514A (R172S) mutant DNA fragment were ligated by a standard method. In FIG. 22, a plasmid containing a mutant ALS gene independently having only C512A(P171H) mutation obtained by the method is described as "pGEX-2T(ALS P171H mutant)," and a plasmid containing a mutant ALS gene independently having only C514A(R172S) mutation is described as "pGEX-2T(ALS R172S mutant)."

After that, *E. coli* (strain JM 109) was transformed using a total volume of the reaction solution. Single colonies that appeared on LB media containing ampicillin were screened by PCR in a manner similar to the above method, so that *E. coli* transformed with pGEX-2T(ALS P171H mutant) and *E. coli* transformed with pGEX-2T(ALS R172S mutant) were selected.

Example 7

Figure 23:
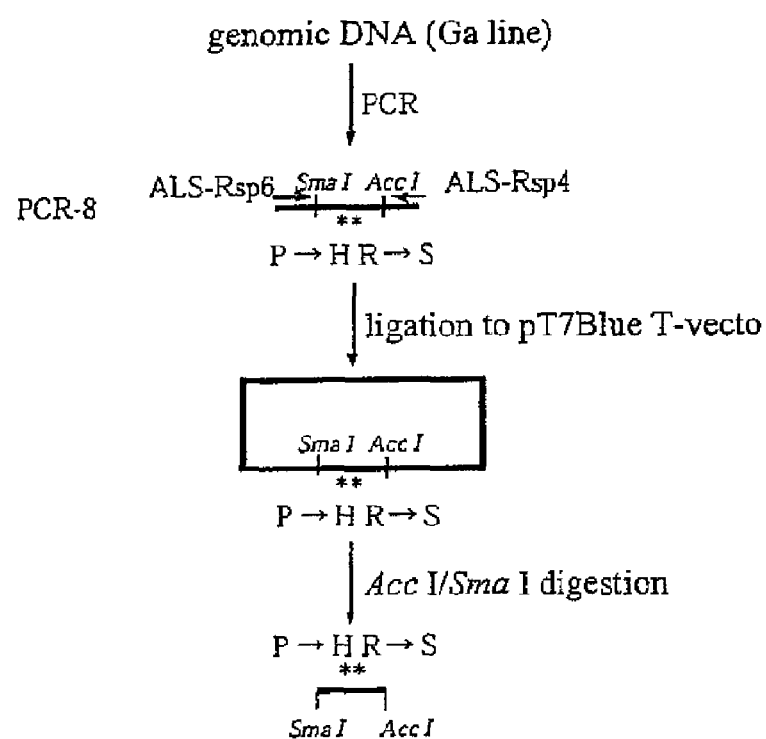
FIG. 23 shows a process for preparing a DNA fragment having C512A(P171H)/C514A(R172S). Arrows denote primers, and asterisks denote mutated points.

Synthesis of 2-point Mutant (C512A(P171H)/C514A(R172S))ALS cDNA, Construction of pGFX-2T Retaining the ALS cDNA, and Transformation of *E. coli* Using This Vector Synthesis of 2-point mutant (C512A(P171H)/C514A (R172S))ALS cDNA, and construction of pGEX-2T retaining the ALS cDNA are described using FIG. 23.

2-point mutant (C512A(P171H)/C514A(R172S))ALS cDNA was synthesized by PCR using as a template the genomic DNA extracted from Ga line, according to the method described in Example 6 above. Specifically, PCR was performed using as a template the genomic DNA extracted from Ga line, and a primer set of ALS-Rsp6 and ALS-Rsp4, thereby amplifying a DNA fragment described as "PCR-8" in FIG. 23. Then, the amplified DNA fragment was ligated into pT7Blue T-vector, followed by digestion with Acc I and Sma I, thereby obtaining C512A(P171H)/C514A(A172S) mutant DNA fragment. Next, as shown in FIG. 22, Acc I-digested/Sma I partially-digested pGEX-2T-wild type ALS cDNA fragment and C512A(P171H)/C514A(R172S) mutant DNA were ligated by a standard method. Thus, pGEX-2T(ALS P171H, R172S mutant) was constructed. Further, similar to Example 6, *E. coli* transformed with pGEX-2T(ALS P171H, R172S mutant) was prepared.

Example 8

Figure 24:
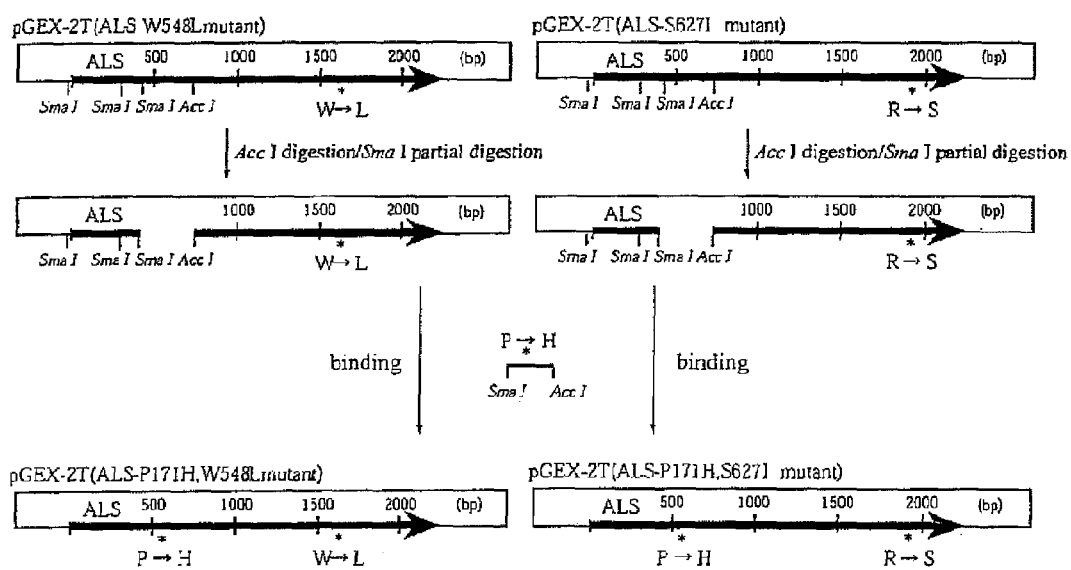
FIG. 24 shows processes for synthesizing P171H/W548L mutant ALS cDNA and P171H/S627I mutant ALS cDNA and for constructing pGEX 2T retaining the ALS cDNA. Asterisks denote mutated points.
Figure 2:
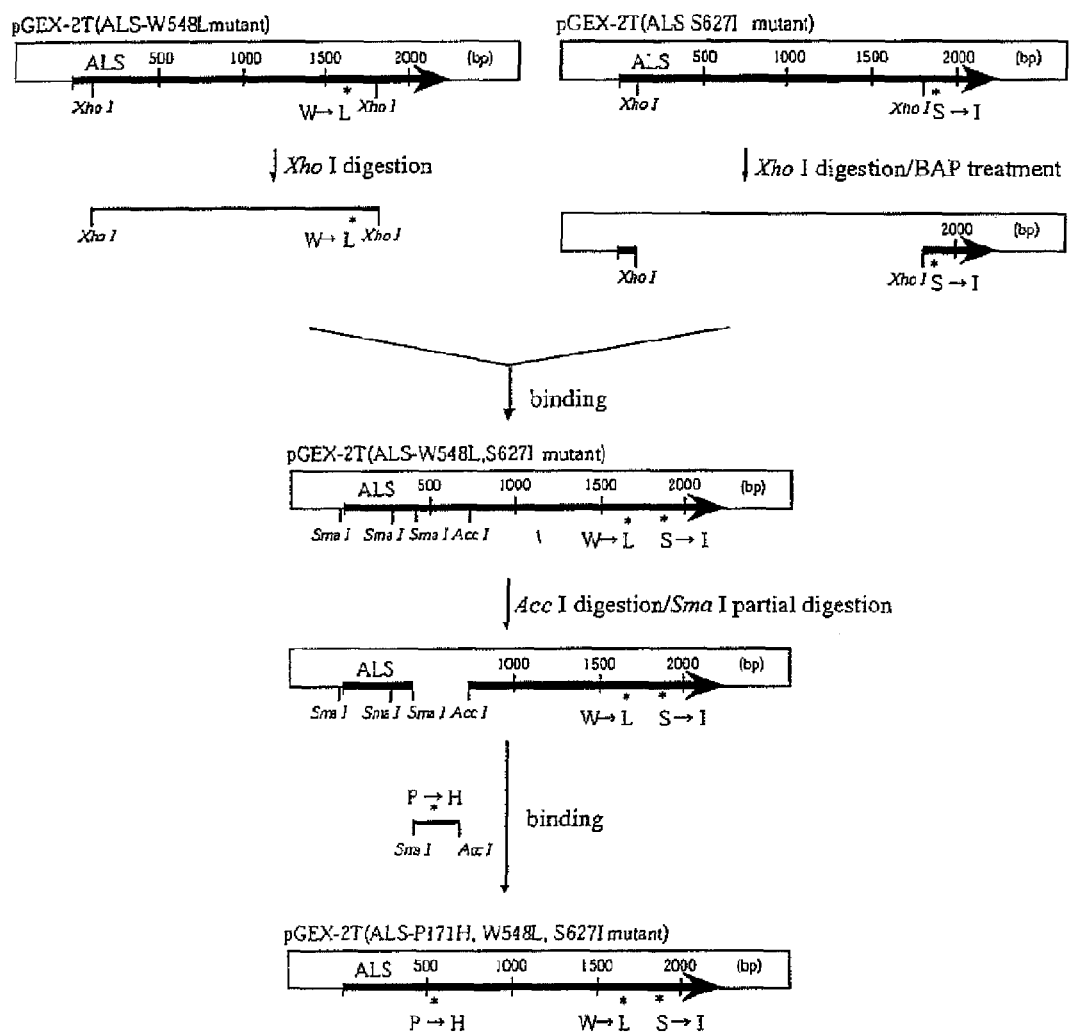

Synthesis of 2-point Mutant (C512A(P171H)/ G1643T(W548L) and C512A(P171H)/G1880T (S627I))ALS cDNA, Construction of pGEX-2T Retaining the ALS cDNA, and Transformation of *E. coli* With This Vector Synthesis of 2-point mutant (C512A(P171H)/G1643T (W548L) and C512A(P171H)/GI880T(S627I))ALS cDNA, and construction of pGEX-2T retaining the ALS cDNA are described using FIG. 24.

First, pGEX 2T(ALS-W548L mutant) obtained in Example 5 was digested with Acc I and then partially digested with Sma I according to the method of Example 6, so as to cause deletion of a portion from the $430^{th}$ Sma I recognition sequence to Acc I recognition sequence of ALS gene. Next, this product and C512A(P 171H) mutant fragment prepared in Example 6 were ligated, so that a plasmid (described as pGEX-2T(ALS-P171II, W548L mutant) in FIG. 24), containing 2-point mutant (C512A(P171H)/G1643T(W548L)) ALS cDNA was constructed.

Meanwhile, using pGEX 2T(ALS-S627I mutant) obtained in Example 5, instead of pGEX 2T(ALS-W548L mutant), a plasmid (described as "pGEX-2T(ALS-P171H, S627I mutant)" in FIG. 24) containing 2-point mutant (C512A (P171H)/G1880T(S627I)) ALS cDNA was constructed similarly.

Further, in a manner similar to the method of Example 6, *E. coli* was transformed using these pGEX-2T(ALS-P171H, W548L mutant) and pGEX-2T(ALS-P171H, S627I mutant).

Example 9

Synthesis of 3-point Mutant (C512A(P171H)/G1643T(W548L)/G1880T(S627I)) ALS cDNA, Construction of pGEX-2T Retaining the ALS cDNA, and Transformation of *E. coli* with this Vector Synthesis of 3-point mutant (C512A(P171H)/G1643T (W548L)/G1880T(S627I)) ALS cDNA, and construction of pGEX-2T retaining this cDNA are described using FIG. 25.

First, after pGEX 2T(ALS-S627I mutant) obtained in Example 5 was digested with Xho I, BAP treatment was performed according to a standard method. Next, according to the above method, a target gene fragment (on the vector side) was separated and purified from agarose gel Further, pGEX 2T(ALS-W548L mutant) obtained in Example 5 was digested with Xho I, and then a fragment containing the mutation was separated and purified from agarose gel according to the above method.

Next, to construct "pGEX-2T(ALS-W548L, S627I mutant)" having 2-point mutation, G1880T(S627I) and G1643T(W548L), the obtained DNA fragments were respectively subjected to ligation reaction. After reaction, the total volume of the reaction solution was transformed into E. coli (strain JM109). Single colonies that appeared on LB media containing ampicillin were screened by PCR according to the above method, and then E. coli having a target plasmid (pGEX-2T(ALS-W548L, S627I mutant)) was selected.

After culturing the selected E. coli, pGEX-2T(ALS-W548L, S627I mutant) was constructed according to the above method. pGEX-2T(ALS-W548L, S627I mutant) was digested with Acc I, and then partially digested with Sma I, thereby constructing pGEX-2T(ALS-W548L, S627I mutant) wherein a portion from the $430^{th}$ Sma I recognition sequence to Acc I recognition sequence in ALS gene had been deleted. Subsequently, ligation of this pGEX-2T and C512A(P171H) mutant fragment prepared in Example 6 was performed, thereby constructing a plasmid containing 3-point mutant (C512A(P171H)/G1643T(W548L)/G1880T(S627I)) ALS cDNA (described as "pGEX-2T(ALS-P171H, W548L, S627I mutant" in FIG. 25).

Further, E. coli was transformed using pGEX-2T(ALS-P171H, W548L, S627I mutant) in a manner similar to the method of Example 6.

Example 10

Expression of Mutant ALS Protein

E. coli transformed with pGEX-2T(ALS-wild) constructed in Example 3(5), E. coli transformed with pGEX-2T(ALS-W548L mutant) constructed in Example 5, E. coli transformed with pGEX-2T(ALS-S627I mutant) constructed in Example 5, E. coli transformed with pGEX-2T(ALS P171H mutant) constructed in Example 6, E. coli transformed with pGEX-2T(ALS R172S mutant) constructed in Example 6, E. coli transformed with pGEX-2T(ALS P171H, R172S mutant) constructed in Example 7, E. coli transformed with pGEX-2T(ALS-P171H, W548L mutant) constructed in Example 8, E. coli transformed with pGEX-2T(ALS-P171H, S627I mutant) constructed in Example 8, and E. coli transformed with pGEX-2T(ALS-P171H, W548L, S627I mutant) constructed in Example 9 were respectively shake-cultured (pre-culture) at 27° C. in 2 ml of LB liquid medium containing ampicillin. These types of E. coli were respectively cultured in 250 ml of LB liquid medium containing ampicillin using 1 ml of the pre-culture solution. After culturing overnight, 1 mM IPTG was added to the media, and then culturing was performed for a further 3 to 4 hours, so that the expression of GST fusion protein was induced. In addition, the cells were stored at –80° C. after washing.

Preparation and purification of ALS from E. coli were performed by the following method. First, the pellet of the transformant E. coli stored at –80° C. was suspended in ALS extraction buffer (potassium phosphate buffer (pH 7.5) containing 30% glycerol and 0.5 mM $MgCl_2$). Specifically, 2.5 ml of the buffer was added to the pellet obtained from 50 ml of the culture solution. The suspension was subjected to ultrasonication (Heat Systems-Ultrasonics, Sonicator W-225R, micro chip, output control 8, interval of approximately 1 second, twice (40 seconds each)), and subjected to centrifugation at 15000×g, 4° C. for 20 minutes, thereby obtaining the supernatant as a crude enzyme solution.

Thus, 9 types of crude enzyme solutions containing any one of GST fusion wild type ALS protein, GST fusion W548L mutant ALS protein, GST fusion S627I mutant ALS protein, GST fusion P171H mutant ALS protein, GST fusion R172S mutant ALS protein, GST fusion P171H/R172S mutant ALS protein, GST fusion P171H/W548L mutant ALS protein, GST fusion P171H/S 627I mutant ALS protein and GST fusion P171H/W548L/S627I mutant ALS protein were prepared.

Example 11

Herbicide Sensitivity of Mutant ALS Protein

Herbicide sensitivity of the wild type ALS protein and that of mutant ALS protein were examined using the 9 types of crude enzyme solutions obtained in Example 10. Herbicide sensitivity test was performed according to procedures almost the same as those in Example 2. However, in this example, reaction temperature was 37° C., reaction time was 30 minutes, and 10 mM valine was added to the reaction solution to inhibit ALS activity derived from E. coli. Further, three types of herbicides, bispyribac-sodium, pyrithiobac-sodium, and pyriminobac, were used as PC herbicides; chlorsulfuron was used as a sulfonylurea herbicide; and imazaquin was used as an imidazolinon herbicide. Before the addition of mutant ALS protein, the solutions of these herbicides (aqueous solutions for bispyribac-sodium and pyrithiobac-sodium, and acetone solutions for other herbicides) at a certain concentration were added into the reaction solutions. The final concentration of acetone was 1%.

Figure 26:
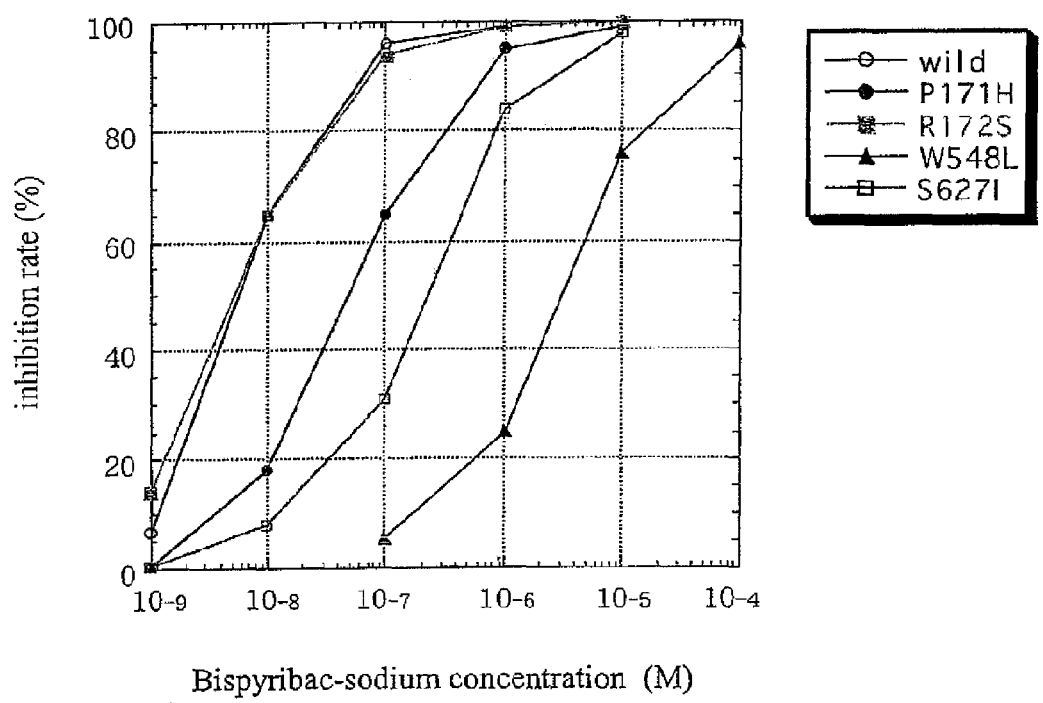
FIG. 26 shows a comparison of sensitivity to bispyribac-sodium between the mutant ALS protein coded by 1-point mutant ALS gene and the wild type ALS protein.
Figure 27:
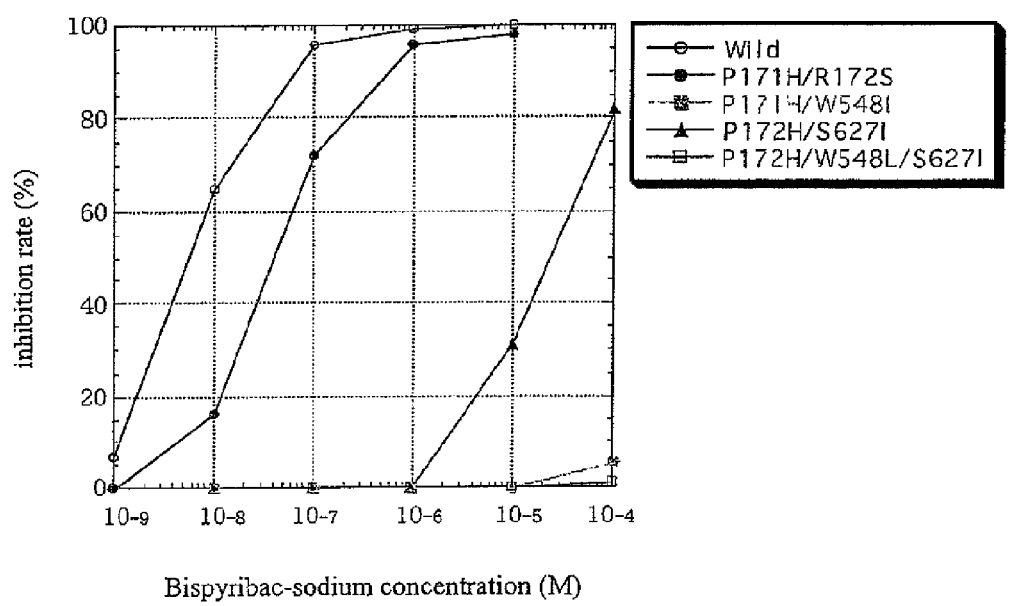
FIG. 27 shows a comparison of sensitivity to bispyribac-sodium among the mutant ALS proteins coded by 2-point and 3-point mutant ALS genes and the wild type.

For the 9 types of crude enzyme solutions, inhibition activity by bispyribac-sodium is shown in FIGS. 26 and 27, and Table 9, inhibition activity by pyrithiobac-sodium is shown in Table 10, inhibition activity by pyriminobac is shown in Table 11, inhibition activity by chlorsulfuron is shown in Table 12, and inhibition activity by imazaquin is shown in Table 13.

In Tables 9 to 13, inhibition activity by each herbicide is represented by a herbicide concentration (I50) which causes 50% inhibition, when 50% inhibition is obtained at a concentration tested, and is represented by inhibition % at the highest concentration among the concentrations tested, when 50% inhibition could not be obtained. Further, in Tables 9 to 13, predicted RS ratio refers to the RS ratio of a mutant ALS protein having multiple mutations, which is a combined RS ratio normally predicted from each RS ratio of mutant ALS proteins independently having a mutation. That is, the predicted RS ratio refers to a synergistic effect normally predicted from a combined RS ratio of mutant ALS proteins independently having a mutation. Specifically, the predicted RS ratio of a mutant ALS protein having multiple mutations was calculated by selecting RS ratios (for all the mutations corresponding to the multiple mutations of this protein) of mutant ALS proteins respectively having only one of the mutations, and then multiplying the selected RS ratios. When an actual RS ratio exceeds the predicted RS ratio of a mutant ALS protein having multiple mutations, this protein has resistance exceeding the synergistic effect (resistance) predicted from a combined resistance of mutant ALS proteins independently having a mutation.

TABLE 9

| ALS protein type | I50 (μM) | RS ratio | Predicted RS ratio | RS ratio/ predicted RS ratio |
|---|---|---|---|---|
| Wild type | 0.0063 | | | |
| P171H mutant | 0.055 | 8.7 | | |
| R172S mutant | 0.0062 | 0.98 | | |
| W548L mutant | 3.3 | 520 | | |
| S627I mutant | 0.26 | 41 | | |
| P171H/R172S mutant | 0.048 | 7.6 | 8.5 | 0.89 |
| P171H/W548L mutant | 5.5% in 100 μM | >15000 | 4500 | >3.3 |
| P171H/S627I mutant | 23 | 3700 | 360 | 10 |
| P171H/W548L/S627I mutant | 1.1% in 100 μM | >16000 | 190000 | >0.084 |

TABLE 10

| ALS protein type | I50 (μM) | RS ratio | Predicted RS ratio | RS ratio/ predicted RS ratio |
|---|---|---|---|---|
| Wild type | 0.011 | | | |
| P171H mutant | 0.037 | 3.4 | | |
| R172S mutant | 0.011 | 1 | | |
| W548L mutant | 41% in 100 μM | >9100 | | |
| S627I mutant | 2.2 | 200 | | |
| P171H/R172S mutant | 0.14 | 13 | 3.4 | 3.8 |
| P171H/W548L mutant | 20% in 100 μM | >9100 | >31000 | |
| P171H/S627I mutant | 9.4 | 850 | 680 | 1.3 |

TABLE 11

| ALS protein type | I50 (μM) | RS ratio | Predicted RS ratio | RS ratio/ predicted RS ratio |
|---|---|---|---|---|
| Wild type | 0.008 | | | |
| P171H mutant | 0.04 | 5 | | |
| R172S mutant | 0.0092 | 1.2 | | |
| W548L mutant | 36 | 4500 | | |
| S627I mutant | 22 | 2800 | | |
| P171H/R172S mutant | 0.041 | 5.1 | 6 | 0.85 |
| P171H/W548L mutant | 11% in 100 μM | >13000 | 23000 | >0.57 |
| P171H/S627I mutant | 21% in 100 μM | >13000 | 14000 | >0.93 |

TABLE 12

| ALS protein type | I50 (μM) | RS ratio | Predicted RS ratio | RS ratio/ predicted RS ratio |
|---|---|---|---|---|
| Wild type | 0.013 | | | |
| P171H mutant | 1.1 | 85 | | |
| R172S mutant | 0.011 | 0.85 | | |
| W548L mutant | 9.9 | 760 | | |
| S627I mutant | 0.031 | 2.4 | | |
| P171H/R172S mutant | 5.5 | 420 | 72 | 5.8 |
| P171H/W548L mutant | 16% in 100 μM | >7700 | 65000 | >0.18 |
| P171H/S627I mutant | 9.9 | 760 | 200 | 3.8 |
| P171H/W548L/S627I mutant | 30% in 500 μM | >38000 | 160000 | >0.24 |

TABLE 13

| ALS protein type | I50 (μM) | RS ratio | Predicted RS ratio | RS ratio/ predicted RS ratio |
|---|---|---|---|---|
| Wild type | 2.2 | | | |
| P171H mutant | 3.4 | 1.5 | | |
| R172S mutant | 2.3 | 1 | | |
| W548L mutant | 16% in 100 μM | >45 | | |
| S627I mutant | 15 | 6.8 | | |
| P171H/R172S mutant | 3.9 | 1.8 | 1.5 | 1.2 |
| P171H/W548L mutant | 13% in 100 μM | >45 | >68 | |
| P171H/S627I mutant | 71 | 32 | 10 | 3.2 |
| P171H/W548L/S627I mutant | 15% in 100 μM | >45 | >460 | |

Data of the above Tables 9 to 13 are described below in order.

First, data of inhibition activity by bispyribac-sodium (Table 9) revealed the following:

Among mutant ALS protein coded by the 1-point mutant genes (P171H, R172S, W548L and S627I), W548L mutant ALS protein showed the highest resistance to bispyribac-sodium (RS ratio: 520). S627I mutant ALS protein or P171H mutant ALS protein also showed high resistance (RS ratio: 41 and 8-7, respectively), but R172S mutant ALS protein showed resistance only equivalent to that of wild type ALS protein (RS ratio: 0.98). These results revealed that P171H mutation, W548L mutation and S627I mutation in ALS protein are mutations effective in enhancing resistance to bispyribac-sodium. Further, R172S mutation in ALS protein was shown to be a silent mutation.

On the other hand, among mutant ALS proteins coded by the 2-point mutant genes, P171H/W548L mutant ALS protein showed the strongest resistance to bispyribac-sodium (5-5% inhibition in 100 μM, and RS ratio: >15000). P171H/S627I mutant ALS protein also showed strong resistance to bispyribac-sodium (RS ratio: 3700). The degree of resistance of P171H/R172S mutant ALS protein was approximately the same as P17111 mutant ALS protein. Further, P171H/W548L/S627I mutant ALS protein coded by the 3-point mutant gene also imparted strong resistance to bispyribac-sodium (1.1% inhibition when 100 μM, and RS ratio: >15000). In addition, actual results of herbicide dose-response on which these results were based are shown in FIGS. 26 and 27.

For the 2-point and 3-point mutations, the predicted RS ratios and actual RS ratios were compared. RS ratios of P171H/W548L mutant ALS protein and P171H/S627I mutant ALS protein were significantly higher than the predicted RS ratios (the ratio of the RS ratio to the predicted RS ratio was remarkably larger than 1). These results revealed that these two 2-point mutant genes (the gene coding for P171H/W548L mutant ALS protein, and the gene coding for P171H/S627I mutant ALS protein) impart resistance against bispyribac-sodium to ALS protein which is stronger than an additive effect predicted from the degree of each resistance of the 1-point mutant gene.

Next, inhibition activity by pyrithiobac-sodium (Table 10) revealed the following:

Among mutant ALS proteins (P171H, R172S, W548L and S627I) coded by 1-point mutant genes, W548L mutant ALS protein showed the strongest resistance to pyrithiobac-sodium (41% in 100 μM, and RS ratio: >9100). S627I mutant ALS protein also showed resistance (RS ratio: 200), but the degree of the resistance of P171H mutant ALS protein was low (RS ratio: 3.4). R172S mutant ALS protein showed resistance only equivalent to that of the wild type ALS protein (RS ratio: 0.85). These results revealed that P171H mutation, W548L mutation and S627I mutation in ALS proteins are effective mutations in enhancing resistance to pyrithiobac-sodium. Further, R172S mutation in ALS protein was shown to be a silent mutation.

On the other hand, among the mutant ALS proteins coded by 2-point mutant genes, P171H/W548L mutant ALS protein imparted the strongest resistance (20% inhibition in 100 μM, and RS ratio: >9100), followed by P171H/S627I mutant ALS protein (RS ratio: 850). Unlike the data of inhibition activity by bispyribac-sodium shown in Table 9, in the case of pyrithiobac-sodium, P171H/R172S mutant ALS protein showed a degree of resistance higher than that of P171H mutant ALS protein (RS ratio: 13). Thus, it was clarified that R172S mutation, which is a silent mutation by itself, enhances the degree of resistance of P171H mutant ALS protein.

Further, for 2-point mutant ALS proteins, when a combined RS ratio predicted from each RS ratio of 1-point mutant ALS proteins and the actual RS ratio were compared, it was found that the RS ratio of P171H/R172S mutant ALS protein was significantly higher than that of the predicted RS ratio (the ratio of the actual RS ratio to the predicted RS ratio was remarkably larger than 1). These results revealed that P171H/R172S mutant ALS protein showed resistance to pyrithiobac-sodium stronger than that predicted from the degrees of resistances of the 1-point mutant genes.

Next, inhibition activity by pyriminobac (Table 11) revealed the following:

Among mutant ALS proteins coded by 1-point mutant genes (P171H, R172S, W548L and S627I), W548L mutant ALS protein showed the strongest resistance to pyriminobac (RS ratio: 4500). S627I mutant ALS protein also imparted strong resistance (RS ratio: 2800), but the degree of resistance of P171H mutant ALS protein was low (RS ratio: 5). R172S mutant ALS protein showed resistance only equivalent to that of the wild type ALS protein (RS ratio: 1.2). These results revealed that P171H mutation, W543L mutation and S627I mutation in ALS proteins are mutations effective in enhancing resistance to pyriminobac. Further, R172S mutation in ALS protein was shown to be a silent mutation.

Among the mutant ALS proteins coded by the 2-point mutant genes, P171H/W548L mutant ALS protein imparted the strongest resistance (11% inhibition in 100 μM, and RS ratio: >13000), followed by P171H/S627I mutant ALS protein (21% inhibition when 100 μM, and RS ratio: >13000).

For these P171H/W548L mutant ALS and P171H/S627I mutant ALS proteins, predicted RS ratios and actual RS ratios were compared. However, it could not be clarified whether resistance stronger than the resistance predicted from the degrees of resistances of each 1-point mutant gene is shown.

Next, inhibition activity by chlorsulfuron (Table 12) revealed the following:

Among the mutant ALS proteins coded by 1-point mutant genes (P171H, R172S, W548L and S627I), W548L mutant ALS protein showed the strongest resistance to chlorsulfuron (RS ratio: 520). P171H mutant ALS protein showed relatively strong resistance (RS ratio: 85), but the degree of resistance of S627I mutant ALS protein was low (RS ratio: 2.4). R172S mutant ALS protein showed resistance only equivalent to that of the wild type ALS protein (RS ratio: 0.85). These results revealed that P171H mutation and W548L mutation in ALS protein are mutations effective in enhancing resistance to chlorsulfuron. Further, R172S mutation in ALS protein was shown to be a silent mutation.

Among the mutant ALS proteins coded by 2-point mutant genes, P171H/W548L mutant ALS protein imparted the strongest resistance (16% inhibition in 100 μM, and RS ratio: >7700), followed by P171H/S627I mutant ALS protein (RS ratio: 760). Unlike the data of inhibition activity by bispyribac-sodium shown in Table 9, in the case of chlorsulfuron, P171H/R172S mutant ALS protein showed a degree of resistance (RS ratio: 420) higher than that of P171H mutant ALS protein. Thus, it was clarified that R172S mutation, which is a silent mutation by itself, enhances the degree of resistance of P171H mutant ALS protein. Further, P171H/W548L/S627I mutant ALS protein also imparted strong resistance (30% inhibition in 500 μM, and RS ratio: >3800).

For P171H/R172S mutant ALS and P171H/S627I mutant ALS proteins, predicted RS ratios and actual RS ratios were compared. For both proteins, the actual RS ratios were significantly higher than the predicted RS ratios. These results revealed that P171H/R172S mutant ALS protein and P171H/S627I mutant ALS protein showed resistance to chlorsulfuron stronger than that predicted from the degrees of resistances of each 1-point mutant gene.

Next, data of inhibition activity by Imazaquin (Table 13) revealed the following:

Among the mutant ALS proteins coded by 1-point mutant genes (P171H, R172S, W548L and S627I), W548L mutant ALS protein showed the strongest resistance to imazaquin (14% in 100 μM, and RS ratio: >45). S627I mutant ALS protein also showed resistance (RS ratio: 41), but P171H mutant ALS protein showed almost no resistance (RS ratio: 1.5). R172S mutant ALS protein showed resistance only equivalent to that of the wild type ALS protein (RS ratio: 0.98). These results revealed that W548L mutation and S627I mutation in ALS protein are mutations effective in enhancing resistance to imazaquin. Further, P171H mutation and R172S mutation in ALS protein were shown to be silent mutations against imazaquin.

Among the 2-point mutant genes, P171H/W548L mutant ALS protein imparted the strongest resistance (13% inhibition in 100 μM, and RS ratio: >45), followed by P171H/S627I mutant ALS protein (RS ratio: 32). The degree of resistance of P171H/R172S mutant ALS protein was almost the same as that of p171H 1-point mutant gene. Further, P171H/W548L/S627I mutant ALS protein also imparted strong resistance (15% inhibition in 100 μM, and RS ratio: >45).

For these 2-point ALS mutant proteins and 3-point ALS mutant protein, predicted RS ratios and actual RS ratios were compared. The RS ratio of P171H/S627I mutant ALS protein was significantly higher than the predicted RS ratio (the ratio of the actual RS ratio to the predicted RS ratio was clearly larger than 1). These results revealed that P171H/S627I mutant ALS protein showed resistance to imazaquin stronger than that predicted from the degrees of resistances of each 1-point mutant gene.

INDUSTRIAL APPLICABILITY

As described in detail above, the present invention can provide a gene coding for acetolactate synthase showing good resistance to various herbicides, an acetolactate synthase protein coded by the gene, a recombinant vector having the gene, a transformant having the recombinant vector, a plant having the gene, a method for rearing the plant, and a method for selecting a transformant cell using the gene as a selection marker.

Sequence Listing Free Text

SEQ ID NOS: 9 to 34 represent primers.

The $15^{th}$ n in SEQ ID NO: 29 represents a, c, g or t.

What is claimed is:

1. An isolated nucleic acid comprising a nucleic acid sequence encoding a protein consisting of an amino acid sequence of any one of SEQ ID NOS: 2, 4, and 6, wherein said protein has resistance to a pyrimidinyl carboxy herbicide.

2. A recombinant vector, which comprises a nucleic acid comprising a nucleic acid sequence encoding a protein consisting of an amino acid sequence of any one of SEQ ID NOS: 2, 4, and 6, wherein said protein has resistance to a pyrimidinyl carboxy herbicide.

3. A transformant, which has the recombinant vector of claim 2.

4. A plant, comprising the nucleic acid of claim 1, which expresses said protein, and which confers resistance to a bispyribac sodium herbicide, a pyrithiobac sodium herbicide, and a pyriminobac herbicide.

5. A method for cultivating the plant of claim 4, which comprises cultivating the plant in the presence of a bispyribac sodium herbicide, a pyrithiobac sodium herbicide, and/or a pyriminobac herbicide.

6. A method for selecting a transformant cell having the nucleic acid of claim 1, which uses the nucleic acid as a selection marker.

* * * * *

SEQUENCE LISTING

<160> NUMBER OF SEQ ID NOS: 39

<210> SEQ ID NO 1
<211> LENGTH: 2301
<212> TYPE: DNA
<213> ORGANISM: Oryza sativa var. kinmaze
<220> FEATURE:
<221> NAME/KEY: CDS
<222> LOCATION: (48)..(1979)

<400> SEQUENCE: 1

| | | | | | | | | | | | | | | | | |
|---|---|---|---|---|---|---|---|---|---|---|---|---|---|---|---|---|
| cccaaaccca | gaaaccctcg | ccgccgccgc | cgccgccacc | acccacc | atg | gct | acg | | | | | | | | | 56 |
| | | | | | Met | Ala | Thr | | | | | | | | | |
| | | | | | 1 | | | | | | | | | | | |
| acc | gcc | gcg | gcc | gcg | gcc | gcc | gcc | ctg | tcc | gcc | gcc | gcg | acg | gcc | aag | 104 |
| Thr | Ala | Ala | Ala | Ala | Ala | Ala | Ala | Leu | Ser | Ala | Ala | Thr | Ala | Lys | | |
| 5 | | | | | 10 | | | | | 15 | | | | | | |
| acc | ggc | cgt | aag | aac | cac | cag | cga | cac | cac | gtc | ctt | ccc | gct | cga | ggc | 152 |
| Thr | Gly | Arg | Lys | Asn | His | Gln | Arg | His | His | Val | Leu | Pro | Ala | Arg | Gly | |
| 20 | | | | | 25 | | | | | 30 | | | | | 35 | |
| cgg | gtg | ggg | gcg | gcg | gcg | gtc | agg | tgc | tcg | gcg | gtg | tcc | ccg | gtc | acc | 200 |
| Arg | Val | Gly | Ala | Ala | Val | Arg | Cys | Ser | Ala | Val | Ser | Pro | Val | Thr | | |
| | | | | 40 | | | | | 45 | | | | | 50 | | |
| ccg | ccg | tcc | ccg | gcg | ccg | ccg | gcc | acg | ccg | ctc | cgg | ccg | tgg | ggg | ccg | 248 |
| Pro | Pro | Ser | Pro | Ala | Pro | Pro | Ala | Thr | Pro | Leu | Arg | Pro | Trp | Gly | Pro | |
| | | | 55 | | | | | 60 | | | | | 65 | | | |
| gcc | gag | ccc | cgc | aag | ggc | gcg | gac | atc | ctc | gtg | gag | gcg | ctg | gag | cgg | 296 |
| Ala | Glu | Pro | Arg | Lys | Gly | Ala | Asp | Ile | Leu | Val | Glu | Ala | Leu | Glu | Arg | |
| | | 70 | | | | | 75 | | | | | 80 | | | | |
| tgc | ggc | gtc | agc | gac | gtg | ttc | gcc | tac | ccg | ggc | ggc | gcg | tcc | atg | gag | 344 |
| Cys | Gly | Val | Ser | Asp | Val | Phe | Ala | Tyr | Pro | Gly | Gly | Ala | Ser | Met | Glu | |
| | 85 | | | | | 90 | | | | | 95 | | | | | |
| atc | cac | cag | gcg | ctg | acg | cgc | tcc | ccg | gtc | atc | acc | aac | cac | ctc | ttc | 392 |
| Ile | His | Gln | Ala | Leu | Thr | Arg | Ser | Pro | Val | Ile | Thr | Asn | His | Leu | Phe | |
| 100 | | | | | 105 | | | | | 110 | | | | | 115 | |
| cgc | cac | gag | cag | ggc | gag | gcg | ttc | gcg | gcg | tcc | ggg | tac | gcg | cgc | gcg | 440 |
| Arg | His | Glu | Gln | Gly | Glu | Ala | Phe | Ala | Ala | Ser | Gly | Tyr | Ala | Arg | Ala | |
| | | | | 120 | | | | | 125 | | | | | 130 | | |
| tcc | ggc | cgc | gtc | ggg | gtc | tgc | gtc | gcc | acc | tcc | ggc | ccc | ggg | gca | acc | 488 |
| Ser | Gly | Arg | Val | Gly | Val | Cys | Val | Ala | Thr | Ser | Gly | Pro | Gly | Ala | Thr | |
| | | | 135 | | | | | 140 | | | | | 145 | | | |
| aac | ctc | gtg | tcc | gcg | ctc | gcc | gac | gcg | ctg | ctc | gac | tcc | gtc | ccg | atg | 536 |
| Asn | Leu | Val | Ser | Ala | Leu | Ala | Asp | Ala | Leu | Leu | Asp | Ser | Val | Pro | Met | |
| | | 150 | | | | | 155 | | | | | 160 | | | | |
| gtc | gcc | atc | acg | ggc | cag | gtc | cac | agc | cgc | atg | atc | ggc | acc | gac | gcc | 584 |
| Val | Ala | Ile | Thr | Gly | Gln | Val | His | Ser | Arg | Met | Ile | Gly | Thr | Asp | Ala | |
| | 165 | | | | | 170 | | | | | 175 | | | | | |
| ttc | cag | gag | acg | ccc | ata | gtc | gag | gtc | acc | cgc | tcc | atc | acc | aag | cac | 632 |
| Phe | Gln | Glu | Thr | Pro | Ile | Val | Glu | Val | Thr | Arg | Ser | Ile | Thr | Lys | His | |
| 180 | | | | | 185 | | | | | 190 | | | | | 195 | |
| aat | tac | ctt | gtc | ctt | gat | gtg | gag | gac | atc | ccc | cgc | gtc | ata | cag | gaa | 680 |
| Asn | Tyr | Leu | Val | Leu | Asp | Val | Glu | Asp | Ile | Pro | Arg | Val | Ile | Gln | Glu | |
| | | | | 200 | | | | | 205 | | | | | 210 | | |
| gcc | ttc | ttc | ctc | gcg | tcc | tcg | ggc | cgt | cct | ggc | ccg | gtg | ctg | gtc | gac | 728 |
| Ala | Phe | Phe | Leu | Ala | Ser | Ser | Gly | Arg | Pro | Gly | Pro | Val | Leu | Val | Asp | |
| | | | 215 | | | | | 220 | | | | | 225 | | | |
| atc | ccc | aag | gac | atc | cag | cag | cag | atg | gcc | gtg | ccg | gtc | tgg | gac | acc | 776 |
| Ile | Pro | Lys | Asp | Ile | Gln | Gln | Gln | Met | Ala | Val | Pro | Val | Trp | Asp | Thr | |
| | | 230 | | | | | 235 | | | | | 240 | | | | |
| tcg | atg | aat | cta | cca | ggg | tac | atc | gca | cgc | ctg | ccc | aag | cca | ccc | gcg | 824 |

```
Ser Met Asn Leu Pro Gly Tyr Ile Ala Arg Leu Pro Lys Pro Pro Ala
    245                 250                 255 aca gaa ttg ctt gag cag gtc ttg cgt ctg gtt ggc gag tca cgg cgc    872
Thr Glu Leu Leu Glu Gln Val Leu Arg Leu Val Gly Glu Ser Arg Arg
260                 265                 270                 275 ccg att ctc tat gtc ggt ggt ggc tgc tct gca tct ggt gac gaa ttg    920
Pro Ile Leu Tyr Val Gly Gly Gly Cys Ser Ala Ser Gly Asp Glu Leu
                280                 285                 290 cgc tgg ttt gtt gag ctg act ggt atc cca gtt aca acc act ctg atg    968
Arg Trp Phe Val Glu Leu Thr Gly Ile Pro Val Thr Thr Thr Leu Met
            295                 300                 305 ggc ctc ggc aat ttc ccc agt gac gac ccg ttg tcc ctg cgc atg ctt   1016
Gly Leu Gly Asn Phe Pro Ser Asp Asp Pro Leu Ser Leu Arg Met Leu
        310                 315                 320 ggg atg cat ggc acg gtg tac gca aat tat gcc gtg gat aag gct gac   1064
Gly Met His Gly Thr Val Tyr Ala Asn Tyr Ala Val Asp Lys Ala Asp
    325                 330                 335 ctg ttg ctt gcg ttt ggt gtg cgg ttt gat gat cgt gtg aca ggg aaa   1112
Leu Leu Leu Ala Phe Gly Val Arg Phe Asp Asp Arg Val Thr Gly Lys
340                 345                 350                 355 att gag gct ttt gca agc agg gcc aag att gtg cac att gac att gat   1160
Ile Glu Ala Phe Ala Ser Arg Ala Lys Ile Val His Ile Asp Ile Asp
                360                 365                 370 cca gca gag att gga aag aac aag caa cca cat gtg tca att tgc gca   1208
Pro Ala Glu Ile Gly Lys Asn Lys Gln Pro His Val Ser Ile Cys Ala
            375                 380                 385 gat gtt aag ctt gct tta cag ggc ttg aat gct ctg cta caa cag agc   1256
Asp Val Lys Leu Ala Leu Gln Gly Leu Asn Ala Leu Leu Gln Gln Ser
        390                 395                 400 aca aca aag aca agt tct gat ttt agt gca tgg cac aat gag ttg gac   1304
Thr Thr Lys Thr Ser Ser Asp Phe Ser Ala Trp His Asn Glu Leu Asp
    405                 410                 415 cag cag aag agg gag ttt cct ctg ggg tac aaa act ttt ggt gaa gag   1352
Gln Gln Lys Arg Glu Phe Pro Leu Gly Tyr Lys Thr Phe Gly Glu Glu
420                 425                 430                 435 atc cca ccg caa tat gcc att cag gtg ctg gat gag ctg acg aaa ggt   1400
Ile Pro Pro Gln Tyr Ala Ile Gln Val Leu Asp Glu Leu Thr Lys Gly
                440                 445                 450 gag gca atc atc gct act ggt gtt ggg cag cac cag atg tgg gcg gca   1448
Glu Ala Ile Ile Ala Thr Gly Val Gly Gln His Gln Met Trp Ala Ala
            455                 460                 465 caa tat tac acc tac aag cgg cca cgg cag tgg ctg tct tcg gct ggt   1496
Gln Tyr Tyr Thr Tyr Lys Arg Pro Arg Gln Trp Leu Ser Ser Ala Gly
        470                 475                 480 ctg ggc gca atg gga ttt ggg ctg cct gct gca gct ggt gct tct gtg   1544
Leu Gly Ala Met Gly Phe Gly Leu Pro Ala Ala Ala Gly Ala Ser Val
    485                 490                 495 gct aac cca ggt gtc aca gtt gtt gat att gat ggg gat ggt agc ttc   1592
Ala Asn Pro Gly Val Thr Val Val Asp Ile Asp Gly Asp Gly Ser Phe
500                 505                 510                 515 ctc atg aac att cag gag ctg gca ttg atc cgc att gag aac ctc cct   1640
Leu Met Asn Ile Gln Glu Leu Ala Leu Ile Arg Ile Glu Asn Leu Pro
                520                 525                 530 gtg aag gtg atg gtg ttg aac aac caa cat ttg ggt atg gtg gtg caa   1688
Val Lys Val Met Val Leu Asn Asn Gln His Leu Gly Met Val Val Gln
            535                 540                 545 tgg gag gat agg ttt tac aag gcg aat agg gcg cat aca tac ttg ggc   1736
Trp Glu Asp Arg Phe Tyr Lys Ala Asn Arg Ala His Thr Tyr Leu Gly
        550                 555                 560 aac ccg gaa tgt gag agc gag ata tat cca gat ttt gtg act att gct   1784
Asn Pro Glu Cys Glu Ser Glu Ile Tyr Pro Asp Phe Val Thr Ile Ala
```

```
Asn Pro Glu Cys Glu Ser Glu Ile Tyr Pro Asp Phe Val Thr Ile Ala
            565                 570                 575 aag ggg ttc aat att cct gca gtc cgt gta aca aag aag agt gaa gtc        1832
Lys Gly Phe Asn Ile Pro Ala Val Arg Val Thr Lys Lys Ser Glu Val
580                 585                 590                 595 cgt gcc gcc atc aag aag atg ctc gag act cca ggg cca tac ttg ttg        1880
Arg Ala Ala Ile Lys Lys Met Leu Glu Thr Pro Gly Pro Tyr Leu Leu
                600                 605                 610 gat atc atc gtc ccg cac cag gag cat gtg ctg cct atg atc cca agt        1928
Asp Ile Ile Val Pro His Gln Glu His Val Leu Pro Met Ile Pro Ser
            615                 620                 625 ggg ggc gca ttc aag gac atg atc ctg gat ggt gat ggc agg act gtg        1976
Gly Gly Ala Phe Lys Asp Met Ile Leu Asp Gly Asp Gly Arg Thr Val
        630                 635                 640 tat taatctataa tctgtatgtt ggcaaagcac cagcccggcc tatgtttgac             2029
Tyr ctgaatgacc cataaagagt ggtatgccta tgatgtttgt atgtgctcta tcaataacta     2089
aggtgtcaac tatgaaccat atgctcttct gttttacttg tttgatgtgc ttggcatggt     2149
aatcctaatt agcttcctgc tgtctaggtt tgtagtgtgt tgttttctgt aggcatatgc     2209
atcacaagat atcatgtaag tttcttgtcc tacatatcaa taataagaga ataaagtact     2269
tctatgcaaa aaaaaaaaaa aaaaaaaaaa aa                                    2301

<210> SEQ ID NO 2
<211> LENGTH: 644
<212> TYPE: PRT
<213> ORGANISM: Oryza sativa var. kinmaze

<400> SEQUENCE: 2

Met Ala Thr Thr Ala Ala Ala Ala Ala Ala Leu Ser Ala Ala Ala
1               5                   10                  15

Thr Ala Lys Thr Gly Arg Lys Asn His Gln Arg His His Val Leu Pro
                20                  25                  30

Ala Arg Gly Arg Val Gly Ala Ala Val Arg Cys Ser Ala Val Ser
            35                  40                  45

Pro Val Thr Pro Pro Ser Pro Ala Pro Ala Thr Pro Leu Arg Pro
        50                  55                  60

Trp Gly Pro Ala Glu Pro Arg Lys Gly Ala Asp Ile Leu Val Glu Ala
65                  70                  75                  80

Leu Glu Arg Cys Gly Val Ser Asp Val Phe Ala Tyr Pro Gly Gly Ala
                85                  90                  95

Ser Met Glu Ile His Gln Ala Leu Thr Arg Ser Pro Val Ile Thr Asn
            100                 105                 110

His Leu Phe Arg His Glu Gln Gly Glu Ala Phe Ala Ala Ser Gly Tyr
        115                 120                 125

Ala Arg Ala Ser Gly Arg Val Gly Val Cys Val Ala Thr Ser Gly Pro
    130                 135                 140

Gly Ala Thr Asn Leu Val Ser Ala Leu Ala Asp Ala Leu Leu Asp Ser
145                 150                 155                 160

Val Pro Met Val Ala Ile Thr Gly Gln Val His Ser Arg Met Ile Gly
                165                 170                 175

Thr Asp Ala Phe Gln Glu Thr Pro Ile Val Glu Val Thr Arg Ser Ile
            180                 185                 190

Thr Lys His Asn Tyr Leu Val Leu Asp Val Glu Asp Ile Pro Arg Val
        195                 200                 205

Ile Gln Glu Ala Phe Phe Leu Ala Ser Ser Gly Arg Pro Gly Pro Val
```

```
                   210                 215                 220
Leu Val Asp Ile Pro Lys Asp Ile Gln Gln Gln Met Ala Val Pro Val
225                 230                 235                 240

Trp Asp Thr Ser Met Asn Leu Pro Gly Tyr Ile Ala Arg Leu Pro Lys
                    245                 250                 255

Pro Pro Ala Thr Glu Leu Leu Glu Gln Val Leu Arg Leu Val Gly Glu
                260                 265                 270

Ser Arg Arg Pro Ile Leu Tyr Val Gly Gly Cys Ser Ala Ser Gly
            275                 280                 285

Asp Glu Leu Arg Trp Phe Val Glu Leu Thr Gly Ile Pro Val Thr Thr
290                 295                 300

Thr Leu Met Gly Leu Gly Asn Phe Pro Ser Asp Pro Leu Ser Leu
305                 310                 315                 320

Arg Met Leu Gly Met His Gly Thr Val Tyr Ala Asn Tyr Ala Val Asp
                325                 330                 335

Lys Ala Asp Leu Leu Leu Ala Phe Gly Val Arg Phe Asp Arg Val
                340                 345                 350

Thr Gly Lys Ile Glu Ala Phe Ala Ser Arg Ala Lys Ile Val His Ile
            355                 360                 365

Asp Ile Asp Pro Ala Glu Ile Gly Lys Asn Lys Gln Pro His Val Ser
370                 375                 380

Ile Cys Ala Asp Val Lys Leu Ala Leu Gln Gly Leu Asn Ala Leu Leu
385                 390                 395                 400

Gln Gln Ser Thr Thr Lys Thr Ser Ser Asp Phe Ser Ala Trp His Asn
                405                 410                 415

Glu Leu Asp Gln Gln Lys Arg Glu Phe Pro Leu Gly Tyr Lys Thr Phe
            420                 425                 430

Gly Glu Glu Ile Pro Pro Gln Tyr Ala Ile Gln Val Leu Asp Glu Leu
            435                 440                 445

Thr Lys Gly Glu Ala Ile Ile Ala Thr Gly Val Gly Gln His Gln Met
            450                 455                 460

Trp Ala Ala Gln Tyr Tyr Thr Tyr Lys Arg Pro Arg Gln Trp Leu Ser
465                 470                 475                 480

Ser Ala Gly Leu Gly Ala Met Gly Phe Gly Leu Pro Ala Ala Ala Gly
                485                 490                 495

Ala Ser Val Ala Asn Pro Gly Val Thr Val Val Asp Ile Asp Gly Asp
                500                 505                 510

Gly Ser Phe Leu Met Asn Ile Gln Glu Leu Ala Leu Ile Arg Ile Glu
            515                 520                 525

Asn Leu Pro Val Lys Val Met Val Leu Asn Asn Gln His Leu Gly Met
530                 535                 540

Val Val Gln Trp Glu Asp Arg Phe Tyr Lys Ala Asn Arg Ala His Thr
545                 550                 555                 560

Tyr Leu Gly Asn Pro Glu Cys Glu Ser Glu Ile Tyr Pro Asp Phe Val
                565                 570                 575

Thr Ile Ala Lys Gly Phe Asn Ile Pro Ala Val Arg Val Thr Lys Lys
            580                 585                 590

Ser Glu Val Arg Ala Ala Ile Lys Lys Met Leu Glu Thr Pro Gly Pro
            595                 600                 605

Tyr Leu Leu Asp Ile Ile Val Pro His Gln Glu His Val Leu Pro Met
            610                 615                 620

Ile Pro Ser Gly Gly Ala Phe Lys Asp Met Ile Leu Asp Gly Asp Gly
625                 630                 635                 640
```

Arg Thr Val Tyr

<210> SEQ ID NO 3
<211> LENGTH: 2300
<212> TYPE: DNA
<213> ORGANISM: Oryza sativa var. kinmaze
<220> FEATURE:
<221> NAME/KEY: CDS
<222> LOCATION: (48)..(1979)

<400> SEQUENCE: 3

```
cccaaaccca gaaaccctcg ccgccgccgc cgccgccacc acccacc atg gct acg       56
                                                    Met Ala Thr
                                                     1 acc gcc gcg gcc gcg gcc gcc gcc ctg tcc gcc gcc gcg acg gcc aag      104
Thr Ala Ala Ala Ala Ala Ala Ala Leu Ser Ala Ala Ala Thr Ala Lys
    5                   10                  15 acc ggc cgt aag aac cac cag cga cac cac gtc ctt ccc gct cga ggc      152
Thr Gly Arg Lys Asn His Gln Arg His His Val Leu Pro Ala Arg Gly
 20                  25                  30                  35 cgg gtg ggg gcg gcg gcg gtc agg tgc tcg gcg gtg tcc ccg gtc acc      200
Arg Val Gly Ala Ala Ala Val Arg Cys Ser Ala Val Ser Pro Val Thr
                 40                  45                  50 ccg ccg tcc ccg gcg ccg ccg gcc acg ccg ctc cgg ccg tgg ggg ccg      248
Pro Pro Ser Pro Ala Pro Pro Ala Thr Pro Leu Arg Pro Trp Gly Pro
             55                  60                  65 gcc gag ccc cgc aag ggc gcg gac atc ctc gtg gag gcg ctg gag cgg      296
Ala Glu Pro Arg Lys Gly Ala Asp Ile Leu Val Glu Ala Leu Glu Arg
         70                  75                  80 tgc ggc gtc agc gac gtg ttc gcc tac ccg ggc ggc gcg tcc atg gag      344
Cys Gly Val Ser Asp Val Phe Ala Tyr Pro Gly Gly Ala Ser Met Glu
     85                  90                  95 atc cac cag gcg ctg acg cgc tcc ccg gtc atc acc aac cac ctc ttc      392
Ile His Gln Ala Leu Thr Arg Ser Pro Val Ile Thr Asn His Leu Phe
100                 105                 110                 115 cgc cac gag cag ggc gag gcg ttc gcg gcg tcc ggg tac gcg cgc gcg      440
Arg His Glu Gln Gly Glu Ala Phe Ala Ala Ser Gly Tyr Ala Arg Ala
                120                 125                 130 tcc ggc cgc gtc ggg gtc tgc gtc gcc acc tcc ggc ccc ggg gca acc      488
Ser Gly Arg Val Gly Val Cys Val Ala Thr Ser Gly Pro Gly Ala Thr
            135                 140                 145 aac ctc gtg tcc gcg ctc gcc gac gcg ctg ctc gac tcc gtc ccg atg      536
Asn Leu Val Ser Ala Leu Ala Asp Ala Leu Leu Asp Ser Val Pro Met
        150                 155                 160 gtc gcc atc acg ggc cag gtc cac cgc cgc atg atc ggc acc gac gcc      584
Val Ala Ile Thr Gly Gln Val His Arg Arg Met Ile Gly Thr Asp Ala
    165                 170                 175 ttc cag gag acg ccc ata gtc gag gtc acc cgc tcc atc acc aag cac      632
Phe Gln Glu Thr Pro Ile Val Glu Val Thr Arg Ser Ile Thr Lys His
180                 185                 190                 195 aat tac ctt gtc ctt gat gtg gag gac atc ccc cgc gtc ata cag gaa      680
Asn Tyr Leu Val Leu Asp Val Glu Asp Ile Pro Arg Val Ile Gln Glu
                200                 205                 210 gcc ttc ttc ctc gcg tcc tcg ggc cgt cct ggc ccg gtg ctg gtc gac      728
Ala Phe Phe Leu Ala Ser Ser Gly Arg Pro Gly Pro Val Leu Val Asp
            215                 220                 225 atc ccc aag gac atc cag cag cag atg gcc gtg ccg gtc tgg gac acc      776
Ile Pro Lys Asp Ile Gln Gln Gln Met Ala Val Pro Val Trp Asp Thr
        230                 235                 240 tcg atg aat cta cca ggg tac atc gca cgc ctg ccc aag cca ccc gcg      824
Ser Met Asn Leu Pro Gly Tyr Ile Ala Arg Leu Pro Lys Pro Pro Ala
    245                 250                 255
```

```
aca gaa ttg ctt gag cag gtc ttg cgt ctg gtt ggc gag tca cgg cgc      872
Thr Glu Leu Leu Glu Gln Val Leu Arg Leu Val Gly Glu Ser Arg Arg
260                 265                 270                 275 ccg att ctc tat gtc ggt ggt ggc tgc tct gca tct ggt gac gaa ttg      920
Pro Ile Leu Tyr Val Gly Gly Gly Cys Ser Ala Ser Gly Asp Glu Leu
                280                 285                 290 cgc tgg ttt gtt gag ctg act ggt atc cca gtt aca acc act ctg atg      968
Arg Trp Phe Val Glu Leu Thr Gly Ile Pro Val Thr Thr Thr Leu Met
            295                 300                 305 ggc ctc ggc aat ttc ccc agt gac gac ccg ttg tcc ctg cgc atg ctt     1016
Gly Leu Gly Asn Phe Pro Ser Asp Asp Pro Leu Ser Leu Arg Met Leu
        310                 315                 320 ggg atg cat ggc acg gtg tac gca aat tat gcc gtg gat aag gct gac     1064
Gly Met His Gly Thr Val Tyr Ala Asn Tyr Ala Val Asp Lys Ala Asp
    325                 330                 335 ctg ttg ctt gcg ttt ggt gtg cgg ttt gat gat cgt gtg aca ggg aaa     1112
Leu Leu Leu Ala Phe Gly Val Arg Phe Asp Asp Arg Val Thr Gly Lys
340                 345                 350                 355 att gag gct ttt gca agc agg gcc aag att gtg cac att gac att gat     1160
Ile Glu Ala Phe Ala Ser Arg Ala Lys Ile Val His Ile Asp Ile Asp
                360                 365                 370 cca gca gag att gga aag aac aag caa cca cat gtg tca att tgc gca     1208
Pro Ala Glu Ile Gly Lys Asn Lys Gln Pro His Val Ser Ile Cys Ala
            375                 380                 385 gat gtt aag ctt gct tta cag ggc ttg aat gct ctg cta caa cag agc     1256
Asp Val Lys Leu Ala Leu Gln Gly Leu Asn Ala Leu Leu Gln Gln Ser
        390                 395                 400 aca aca aag aca agt tct gat ttt agt gca tgg cac aat gag ttg gac     1304
Thr Thr Lys Thr Ser Ser Asp Phe Ser Ala Trp His Asn Glu Leu Asp
    405                 410                 415 cag cag aag agg gag ttt cct ctg ggg tac aaa act ttt ggt gaa gag     1352
Gln Gln Lys Arg Glu Phe Pro Leu Gly Tyr Lys Thr Phe Gly Glu Glu
420                 425                 430                 435 atc cca ccg caa tat gcc att cag gtg ctg gat gag ctg acg aaa ggt     1400
Ile Pro Pro Gln Tyr Ala Ile Gln Val Leu Asp Glu Leu Thr Lys Gly
                440                 445                 450 gag gca atc atc gct act ggt gtt ggg cag cac cag atg tgg gcg gca     1448
Glu Ala Ile Ile Ala Thr Gly Val Gly Gln His Gln Met Trp Ala Ala
            455                 460                 465 caa tat tac acc tac aag cgg cca cgg cag tgg ctg tct tcg gct ggt     1496
Gln Tyr Tyr Thr Tyr Lys Arg Pro Arg Gln Trp Leu Ser Ser Ala Gly
        470                 475                 480 ctg ggc gca atg gga ttt ggg ctg cct gct gca gct ggt gct tct gtg     1544
Leu Gly Ala Met Gly Phe Gly Leu Pro Ala Ala Ala Gly Ala Ser Val
    485                 490                 495 gct aac cca ggt gtc aca gtt gtt gat att gat ggg gat ggt agc ttc     1592
Ala Asn Pro Gly Val Thr Val Val Asp Ile Asp Gly Asp Gly Ser Phe
500                 505                 510                 515 ctc atg aac att cag gag ctg gca ttg atc cgc att gag aac ctc cct     1640
Leu Met Asn Ile Gln Glu Leu Ala Leu Ile Arg Ile Glu Asn Leu Pro
                520                 525                 530 gtg aag gtg atg gtg ttg aac aac caa cat ttg ggt atg gtg gtg caa     1688
Val Lys Val Met Val Leu Asn Asn Gln His Leu Gly Met Val Val Gln
            535                 540                 545 ttg gag gat agg ttt tac aag gcg aat agg gcg cat aca tac ttg ggc     1736
Leu Glu Asp Arg Phe Tyr Lys Ala Asn Arg Ala His Thr Tyr Leu Gly
        550                 555                 560 aac ccg gaa tgt gag agc gag ata tat cca gat ttt gtg act att gct     1784
Asn Pro Glu Cys Glu Ser Glu Ile Tyr Pro Asp Phe Val Thr Ile Ala
    565                 570                 575
```

```
aag ggg ttc aat att cct gca gtc cgt gta aca aag aag agt gaa gtc    1832
Lys Gly Phe Asn Ile Pro Ala Val Arg Val Thr Lys Lys Ser Glu Val
580                 585                 590                 595 cgt gcc gcc atc aag aag atg ctc gag act cca ggg cca tac ttg ttg    1880
Arg Ala Ala Ile Lys Lys Met Leu Glu Thr Pro Gly Pro Tyr Leu Leu
                600                 605                 610 gat atc atc gtc ccg cac cag gag cat gtg ctg cct atg atc cca agt    1928
Asp Ile Ile Val Pro His Gln Glu His Val Leu Pro Met Ile Pro Ser
                615                 620                 625 ggg ggc gca ttc aag gac atg atc ctg gat ggt gat ggc agg act gtg    1976
Gly Gly Ala Phe Lys Asp Met Ile Leu Asp Gly Asp Gly Arg Thr Val
                630                 635                 640 tat taatctataa tctgtatgtt ggcaaagcac cagcccggcc tatgtttgac         2029
Tyr ctgaatgacc cataaagagt ggtatgccta tgatgtttgt atgtgctcta tcaataacta  2089
aggtgtcaac tatgaaccat atgctcttct gttttacttg tttgatgtgc ttggcatggt  2149
aatcctaatt agcttcctgc tgtctaggtt tgtagtgtgt tgttttctgt aggcatatgc  2209
atcacaagat atcatgtaag tttcttgtcc tacatatcaa taataagaga ataaagtact  2269
tctatgcaaa aaaaaaaaaa aaaaaaaaaa a                                 2300

<210> SEQ ID NO 4
<211> LENGTH: 644
<212> TYPE: PRT
<213> ORGANISM: Oryza sativa var. kinmaze

<400> SEQUENCE: 4

Met Ala Thr Thr Ala Ala Ala Ala Ala Ala Leu Ser Ala Ala
1               5                   10                  15

Thr Ala Lys Thr Gly Arg Lys Asn His Gln Arg His Val Leu Pro
            20                  25                  30

Ala Arg Gly Arg Val Gly Ala Ala Val Arg Cys Ser Ala Val Ser
        35                  40                  45

Pro Val Thr Pro Pro Ser Pro Ala Pro Pro Ala Thr Pro Leu Arg Pro
    50                  55                  60

Trp Gly Pro Ala Glu Pro Arg Lys Gly Ala Asp Ile Leu Val Glu Ala
65                  70                  75                  80

Leu Glu Arg Cys Gly Val Ser Asp Val Phe Ala Tyr Pro Gly Gly Ala
                85                  90                  95

Ser Met Glu Ile His Gln Ala Leu Thr Arg Ser Pro Val Ile Thr Asn
            100                 105                 110

His Leu Phe Arg His Glu Gln Gly Glu Ala Phe Ala Ala Ser Gly Tyr
        115                 120                 125

Ala Arg Ala Ser Gly Arg Val Gly Val Cys Val Ala Thr Ser Gly Pro
    130                 135                 140

Gly Ala Thr Asn Leu Val Ser Ala Leu Ala Asp Ala Leu Leu Asp Ser
145                 150                 155                 160

Val Pro Met Val Ala Ile Thr Gly Gln Val His Arg Arg Met Ile Gly
                165                 170                 175

Thr Asp Ala Phe Gln Glu Thr Pro Ile Val Glu Val Thr Arg Ser Ile
            180                 185                 190

Thr Lys His Asn Tyr Leu Val Leu Asp Val Glu Asp Ile Pro Arg Val
        195                 200                 205

Ile Gln Glu Ala Phe Phe Leu Ala Ser Ser Gly Arg Pro Gly Pro Val
    210                 215                 220
```

```
Leu Val Asp Ile Pro Lys Asp Ile Gln Gln Gln Met Ala Val Pro Val
225                 230                 235                 240

Trp Asp Thr Ser Met Asn Leu Pro Gly Tyr Ile Ala Arg Leu Pro Lys
                245                 250                 255

Pro Pro Ala Thr Glu Leu Leu Glu Gln Val Leu Arg Leu Val Gly Glu
            260                 265                 270

Ser Arg Arg Pro Ile Leu Tyr Val Gly Gly Cys Ser Ala Ser Gly
        275                 280                 285

Asp Glu Leu Arg Trp Phe Val Glu Leu Thr Gly Ile Pro Val Thr Thr
            290                 295                 300

Thr Leu Met Gly Leu Gly Asn Phe Pro Ser Asp Pro Leu Ser Leu
305                 310                 315                 320

Arg Met Leu Gly Met His Gly Thr Val Tyr Ala Asn Tyr Ala Val Asp
                325                 330                 335

Lys Ala Asp Leu Leu Ala Phe Gly Val Arg Phe Asp Asp Arg Val
            340                 345                 350

Thr Gly Lys Ile Glu Ala Phe Ala Ser Arg Ala Lys Ile Val His Ile
            355                 360                 365

Asp Ile Asp Pro Ala Glu Ile Gly Lys Asn Lys Gln Pro His Val Ser
370                 375                 380

Ile Cys Ala Asp Val Lys Leu Ala Leu Gln Gly Leu Asn Ala Leu Leu
385                 390                 395                 400

Gln Gln Ser Thr Thr Lys Thr Ser Ser Asp Phe Ser Ala Trp His Asn
                405                 410                 415

Glu Leu Asp Gln Gln Lys Arg Glu Phe Pro Leu Gly Tyr Lys Thr Phe
            420                 425                 430

Gly Glu Glu Ile Pro Pro Gln Tyr Ala Ile Gln Val Leu Asp Glu Leu
            435                 440                 445

Thr Lys Gly Glu Ala Ile Ile Ala Thr Gly Val Gly Gln His Gln Met
            450                 455                 460

Trp Ala Ala Gln Tyr Tyr Thr Tyr Lys Arg Pro Arg Gln Trp Leu Ser
465                 470                 475                 480

Ser Ala Gly Leu Gly Ala Met Gly Phe Gly Leu Pro Ala Ala Ala Gly
                485                 490                 495

Ala Ser Val Ala Asn Pro Gly Val Thr Val Val Asp Ile Asp Gly Asp
            500                 505                 510

Gly Ser Phe Leu Met Asn Ile Gln Glu Leu Ala Leu Ile Arg Ile Glu
            515                 520                 525

Asn Leu Pro Val Lys Val Met Val Leu Asn Asn Gln Leu Gly Met
            530                 535                 540

Val Val Gln Leu Glu Asp Arg Phe Tyr Lys Ala Asn Arg Ala His Thr
545                 550                 555                 560

Tyr Leu Gly Asn Pro Glu Cys Glu Ser Glu Ile Tyr Pro Asp Phe Val
                565                 570                 575

Thr Ile Ala Lys Gly Phe Asn Ile Pro Ala Val Arg Val Thr Lys Lys
            580                 585                 590

Ser Glu Val Arg Ala Ala Ile Lys Lys Met Leu Glu Thr Pro Gly Pro
            595                 600                 605

Tyr Leu Leu Asp Ile Ile Val Pro His Gln Glu His Val Leu Pro Met
            610                 615                 620

Ile Pro Ser Gly Gly Ala Phe Lys Asp Met Ile Leu Asp Gly Asp Gly
625                 630                 635                 640

Arg Thr Val Tyr
```

<210> SEQ ID NO 5
<211> LENGTH: 2294
<212> TYPE: DNA
<213> ORGANISM: Oryza sativa var. kinmaze
<220> FEATURE:
<221> NAME/KEY: CDS
<222> LOCATION: (48)..(1979)

<400> SEQUENCE: 5

| | | | | | | | | | | | | | | | | |
|---|---|---|---|---|---|---|---|---|---|---|---|---|---|---|---|---|
| cccaaaccca | gaaaccctcg | ccgccgccgc | cgccgccacc | acccacc | atg | gct | acg | | | | | | | | | 56 |
| | | | | | Met | Ala | Thr | | | | | | | | | |
| | | | | | 1 | | | | | | | | | | | |
| acc | gcc | gcg | gcc | gcg | gcc | gcc | gcc | ctg | tcc | gcc | gcc | gcg | acg | gcc | aag | 104 |
| Thr | Ala | Ala | Ala | Ala | Ala | Ala | Ala | Leu | Ser | Ala | Ala | Ala | Thr | Ala | Lys | |
| | 5 | | | | 10 | | | | | 15 | | | | | | |
| acc | ggc | cgt | aag | aac | cac | cag | cga | cac | cac | gtc | ctt | ccc | gct | cga | ggc | 152 |
| Thr | Gly | Arg | Lys | Asn | His | Gln | Arg | His | His | Val | Leu | Pro | Ala | Arg | Gly | |
| 20 | | | | | 25 | | | | | 30 | | | | | 35 | |
| cgg | gtg | ggg | gcg | gcg | gcg | gtc | agg | tgc | tcg | gcg | gtg | tcc | ccg | gtc | acc | 200 |
| Arg | Val | Gly | Ala | Ala | Val | Arg | Cys | Ser | Ala | Val | Ser | Pro | Val | Thr | | |
| | | | 40 | | | | | 45 | | | | | 50 | | | |
| ccg | ccg | tcc | ccg | gcg | ccg | ccg | gcc | acg | ccg | ctc | cgg | ccg | tgg | ggg | ccg | 248 |
| Pro | Pro | Ser | Pro | Ala | Pro | Pro | Ala | Thr | Pro | Leu | Arg | Pro | Trp | Gly | Pro | |
| | | 55 | | | | | 60 | | | | | 65 | | | | |
| gcc | gag | ccc | cgc | aag | ggc | gcg | gac | atc | ctc | gtg | gag | gcg | ctg | gag | cgg | 296 |
| Ala | Glu | Pro | Arg | Lys | Gly | Ala | Asp | Ile | Leu | Val | Glu | Ala | Leu | Glu | Arg | |
| | 70 | | | | | 75 | | | | | 80 | | | | | |
| tgc | ggc | gtc | agc | gac | gtg | ttc | gcc | tac | ccg | ggc | ggc | gcg | tcc | atg | gag | 344 |
| Cys | Gly | Val | Ser | Asp | Val | Phe | Ala | Tyr | Pro | Gly | Gly | Ala | Ser | Met | Glu | |
| 85 | | | | | 90 | | | | | 95 | | | | | | |
| atc | cac | cag | gcg | ctg | acg | cgc | tcc | ccg | gtc | atc | acc | aac | cac | ctc | ttc | 392 |
| Ile | His | Gln | Ala | Leu | Thr | Arg | Ser | Pro | Val | Ile | Thr | Asn | His | Leu | Phe | |
| 100 | | | | | 105 | | | | | 110 | | | | | 115 | |
| cgc | cac | gag | cag | ggc | gag | gcg | ttc | gcg | gcg | tcc | ggg | tac | gcg | cgc | gcg | 440 |
| Arg | His | Glu | Gln | Gly | Glu | Ala | Phe | Ala | Ala | Ser | Gly | Tyr | Ala | Arg | Ala | |
| | | | 120 | | | | | 125 | | | | | 130 | | | |
| tcc | ggc | cgc | gtc | ggg | gtc | tgc | gtc | gcc | acc | tcc | ggc | ccc | ggg | gca | acc | 488 |
| Ser | Gly | Arg | Val | Gly | Val | Cys | Val | Ala | Thr | Ser | Gly | Pro | Gly | Ala | Thr | |
| | | 135 | | | | | 140 | | | | | 145 | | | | |
| aac | ctc | gtg | tcc | gcg | ctc | gcc | gac | gcg | ctg | ctc | gac | tcc | gtc | ccg | atg | 536 |
| Asn | Leu | Val | Ser | Ala | Leu | Ala | Asp | Ala | Leu | Leu | Asp | Ser | Val | Pro | Met | |
| | 150 | | | | | 155 | | | | | 160 | | | | | |
| gtc | gcc | atc | acg | ggc | cag | gtc | cac | cgc | cgc | atg | atc | ggc | acc | gac | gcc | 584 |
| Val | Ala | Ile | Thr | Gly | Gln | Val | His | Arg | Arg | Met | Ile | Gly | Thr | Asp | Ala | |
| 165 | | | | | 170 | | | | | 175 | | | | | | |
| ttc | cag | gag | acg | ccc | ata | gtc | gag | gtc | acc | cgc | tcc | atc | acc | aag | cac | 632 |
| Phe | Gln | Glu | Thr | Pro | Ile | Val | Glu | Val | Thr | Arg | Ser | Ile | Thr | Lys | His | |
| 180 | | | | | 185 | | | | | 190 | | | | | 195 | |
| aat | tac | ctt | gtc | ctt | gat | gtg | gag | gac | atc | ccc | cgc | gtc | ata | cag | gaa | 680 |
| Asn | Tyr | Leu | Val | Leu | Asp | Val | Glu | Asp | Ile | Pro | Arg | Val | Ile | Gln | Glu | |
| | | | 200 | | | | | 205 | | | | | 210 | | | |
| gcc | ttc | ttc | ctc | gcg | tcc | tcg | ggc | cgt | cct | ggc | ccg | gtg | ctg | gtc | gac | 728 |
| Ala | Phe | Phe | Leu | Ala | Ser | Ser | Gly | Arg | Pro | Gly | Pro | Val | Leu | Val | Asp | |
| | | 215 | | | | | 220 | | | | | 225 | | | | |
| atc | ccc | aag | gac | atc | cag | cag | cag | atg | gcc | gtg | ccg | gtc | tgg | gac | acc | 776 |
| Ile | Pro | Lys | Asp | Ile | Gln | Gln | Gln | Met | Ala | Val | Pro | Val | Trp | Asp | Thr | |
| | 230 | | | | | 235 | | | | | 240 | | | | | |
| tcg | atg | aat | cta | cca | ggg | tac | atc | gca | cgc | ctg | ccc | aag | cca | ccc | gcg | 824 |
| Ser | Met | Asn | Leu | Pro | Gly | Tyr | Ile | Ala | Arg | Leu | Pro | Lys | Pro | Pro | Ala | |
| 245 | | | | | 250 | | | | | 255 | | | | | | |
| aca | gaa | ttg | ctt | gag | cag | gtc | ttg | cgt | ctg | gtt | ggc | gag | tca | cgg | cgc | 872 |

```
                Thr Glu Leu Leu Glu Gln Val Leu Arg Leu Val Gly Glu Ser Arg Arg
                260                 265                 270                 275 ccg att ctc tat gtc ggt ggt ggc tgc tct gca tct ggt gac gaa ttg              920
Pro Ile Leu Tyr Val Gly Gly Gly Cys Ser Ala Ser Gly Asp Glu Leu
                        280                 285                 290 cgc tgg ttt gtt gag ctg act ggt atc cca gtt aca acc act ctg atg             968
Arg Trp Phe Val Glu Leu Thr Gly Ile Pro Val Thr Thr Thr Leu Met
                295                 300                 305 ggc ctc ggc aat ttc ccc agt gac gac ccg ttg tcc ctg cgc atg ctt            1016
Gly Leu Gly Asn Phe Pro Ser Asp Asp Pro Leu Ser Leu Arg Met Leu
        310                 315                 320 ggg atg cat ggc acg gtg tac gca aat tat gcc gtg gat aag gct gac            1064
Gly Met His Gly Thr Val Tyr Ala Asn Tyr Ala Val Asp Lys Ala Asp
            325                 330                 335 ctg ttg ctt gcg ttt ggt gtg cgg ttt gat gat cgt gtg aca ggg aaa            1112
Leu Leu Leu Ala Phe Gly Val Arg Phe Asp Asp Arg Val Thr Gly Lys
340                 345                 350                 355 att gag gct ttt gca agc agg gcc aag att gtg cac att gac att gat            1160
Ile Glu Ala Phe Ala Ser Arg Ala Lys Ile Val His Ile Asp Ile Asp
                        360                 365                 370 cca gca gag att gga aag aac aag caa cca cat gtg tca att tgc gca            1208
Pro Ala Glu Ile Gly Lys Asn Lys Gln Pro His Val Ser Ile Cys Ala
                375                 380                 385 gat gtt aag ctt gct tta cag ggc ttg aat gct ctg cta caa cag agc            1256
Asp Val Lys Leu Ala Leu Gln Gly Leu Asn Ala Leu Leu Gln Gln Ser
            390                 395                 400 aca aca aag aca agt tct gat ttt agt gca tgg cac aat gag ttg gac            1304
Thr Thr Lys Thr Ser Ser Asp Phe Ser Ala Trp His Asn Glu Leu Asp
405                 410                 415 cag cag aag agg gag ttt cct ctg ggg tac aaa act ttt ggt gaa gag            1352
Gln Gln Lys Arg Glu Phe Pro Leu Gly Tyr Lys Thr Phe Gly Glu Glu
420                 425                 430                 435 atc cca ccg caa tat gcc att cag gtg ctg gat gag ctg acg aaa ggt            1400
Ile Pro Pro Gln Tyr Ala Ile Gln Val Leu Asp Glu Leu Thr Lys Gly
                        440                 445                 450 gag gca atc atc gct act ggt gtt ggg cag cac cag atg tgg gcg gca            1448
Glu Ala Ile Ile Ala Thr Gly Val Gly Gln His Gln Met Trp Ala Ala
                455                 460                 465 caa tat tac acc tac aag cgg cca cgg cag tgg ctg tct tcg gct ggt            1496
Gln Tyr Tyr Thr Tyr Lys Arg Pro Arg Gln Trp Leu Ser Ser Ala Gly
            470                 475                 480 ctg ggc gca atg gga ttt ggg ctg cct gct gca gct ggt gct tct gtg            1544
Leu Gly Ala Met Gly Phe Gly Leu Pro Ala Ala Ala Gly Ala Ser Val
485                 490                 495 gct aac cca ggt gtc aca gtt gtt gat att gat ggg gat ggt agc ttc            1592
Ala Asn Pro Gly Val Thr Val Val Asp Ile Asp Gly Asp Gly Ser Phe
500                 505                 510                 515 ctc atg aac att cag gag ctg gca ttg atc cgc att gag aac ctc cct            1640
Leu Met Asn Ile Gln Glu Leu Ala Leu Ile Arg Ile Glu Asn Leu Pro
                        520                 525                 530 gtg aag gtg atg gtg ttg aac aac caa cat ttg ggt atg gtg gtg caa            1688
Val Lys Val Met Val Leu Asn Asn Gln His Leu Gly Met Val Val Gln
                535                 540                 545 tgg gag gat agg ttt tac aag gcg aat agg gcg cat aca tac ttg ggc            1736
Trp Glu Asp Arg Phe Tyr Lys Ala Asn Arg Ala His Thr Tyr Leu Gly
            550                 555                 560 aac ccg gaa tgt gag agc gag ata tat cca gat ttt gtg act att gct            1784
Asn Pro Glu Cys Glu Ser Glu Ile Tyr Pro Asp Phe Val Thr Ile Ala
565                 570                 575 aag ggg ttc aat att cct gca gtc cgt gta aca aag aag agt gaa gtc            1832
```

```
Lys Gly Phe Asn Ile Pro Ala Val Arg Val Thr Lys Ser Glu Val
580                 585                 590                 595 cgt gcc gcc atc aag aag atg ctc gag act cca ggg cca tac ttg ttg    1880
Arg Ala Ala Ile Lys Lys Met Leu Glu Thr Pro Gly Pro Tyr Leu Leu
                600                 605                 610 gat atc atc gtc ccg cac cag gag cat gtg ctg cct atg atc cca att    1928
Asp Ile Ile Val Pro His Gln Glu His Val Leu Pro Met Ile Pro Ile
            615                 620                 625 ggg ggc gca ttc aag gac atg atc ctg gat ggt gat ggc agg act gtg    1976
Gly Gly Ala Phe Lys Asp Met Ile Leu Asp Gly Asp Gly Arg Thr Val
        630                 635                 640 tat taatctataa tctgtatgtt ggcaaagcac cagcccggcc tatgtttgac         2029
Tyr ctgaatgacc cataaagagt ggtatgccta tgatgtttgt atgtgctcta tcaataacta  2089
aggtgtcaac tatgaaccat atgctcttct gttttacttg tttgatgtgc ttggcatggt  2149
aatcctaatt agcttcctgc tgtctaggtt tgtagtgtgt tgttttctgt aggcatatgc  2209
atcacaagat atcatgtaag tttcttgtcc tacatatcaa taataagaga ataaagtact  2269
tctatgtaaa aaaaaaaaaa aaaaa                                        2294

<210> SEQ ID NO 6
<211> LENGTH: 644
<212> TYPE: PRT
<213> ORGANISM: Oryza sativa var. kinmaze

<400> SEQUENCE: 6

Met Ala Thr Thr Ala Ala Ala Ala Ala Ala Leu Ser Ala Ala Ala
1               5                   10                  15

Thr Ala Lys Thr Gly Arg Lys Asn His Gln Arg His His Val Leu Pro
                20                  25                  30

Ala Arg Gly Arg Val Gly Ala Ala Val Arg Cys Ser Ala Val Ser
            35                  40                  45

Pro Val Thr Pro Pro Ser Pro Ala Pro Pro Thr Pro Leu Arg Pro
        50                  55                  60

Trp Gly Pro Ala Glu Pro Arg Lys Gly Ala Asp Ile Leu Val Glu Ala
65                  70                  75                  80

Leu Glu Arg Cys Gly Val Ser Asp Val Phe Ala Tyr Pro Gly Gly Ala
                85                  90                  95

Ser Met Glu Ile His Gln Ala Leu Thr Arg Ser Pro Val Ile Thr Asn
                100                 105                 110

His Leu Phe Arg His Glu Gln Gly Glu Ala Phe Ala Ala Ser Gly Tyr
            115                 120                 125

Ala Arg Ala Ser Gly Arg Val Gly Val Cys Val Ala Thr Ser Gly Pro
        130                 135                 140

Gly Ala Thr Asn Leu Val Ser Ala Leu Ala Asp Ala Leu Leu Asp Ser
145                 150                 155                 160

Val Pro Met Val Ala Ile Thr Gly Gln Val His Arg Arg Met Ile Gly
                165                 170                 175

Thr Asp Ala Phe Gln Glu Thr Pro Ile Val Glu Val Thr Arg Ser Ile
                180                 185                 190

Thr Lys His Asn Tyr Leu Val Leu Asp Val Glu Asp Ile Pro Arg Val
            195                 200                 205

Ile Gln Glu Ala Phe Phe Leu Ala Ser Ser Gly Arg Pro Gly Pro Val
        210                 215                 220

Leu Val Asp Ile Pro Lys Asp Ile Gln Gln Gln Met Ala Val Pro Val
225                 230                 235                 240
```

Trp Asp Thr Ser Met Asn Leu Pro Gly Tyr Ile Ala Arg Leu Pro Lys
            245                 250                 255

Pro Pro Ala Thr Glu Leu Leu Glu Gln Val Leu Arg Leu Val Gly Glu
            260                 265                 270

Ser Arg Arg Pro Ile Leu Tyr Val Gly Gly Gly Cys Ser Ala Ser Gly
            275                 280                 285

Asp Glu Leu Arg Trp Phe Val Glu Leu Thr Gly Ile Pro Val Thr Thr
290                 295                 300

Thr Leu Met Gly Leu Gly Asn Phe Pro Ser Asp Pro Leu Ser Leu
305                 310                 315                 320

Arg Met Leu Gly Met His Gly Thr Val Tyr Ala Asn Tyr Ala Val Asp
                325                 330                 335

Lys Ala Asp Leu Leu Ala Phe Gly Val Arg Phe Asp Asp Arg Val
            340                 345                 350

Thr Gly Lys Ile Glu Ala Phe Ala Ser Arg Ala Lys Ile Val His Ile
            355                 360                 365

Asp Ile Asp Pro Ala Glu Ile Gly Lys Asn Lys Gln Pro His Val Ser
370                 375                 380

Ile Cys Ala Asp Val Lys Leu Ala Leu Gln Gly Leu Asn Ala Leu Leu
385                 390                 395                 400

Gln Gln Ser Thr Thr Lys Thr Ser Ser Asp Phe Ser Ala Trp His Asn
            405                 410                 415

Glu Leu Asp Gln Gln Lys Arg Glu Phe Pro Leu Gly Tyr Lys Thr Phe
            420                 425                 430

Gly Glu Glu Ile Pro Pro Gln Tyr Ala Ile Gln Val Leu Asp Glu Leu
            435                 440                 445

Thr Lys Gly Glu Ala Ile Ile Ala Thr Gly Val Gly Gln His Gln Met
450                 455                 460

Trp Ala Ala Gln Tyr Tyr Thr Tyr Lys Arg Pro Arg Gln Trp Leu Ser
465                 470                 475                 480

Ser Ala Gly Leu Gly Ala Met Gly Phe Gly Leu Pro Ala Ala Ala Gly
            485                 490                 495

Ala Ser Val Ala Asn Pro Gly Val Thr Val Val Asp Ile Asp Gly Asp
            500                 505                 510

Gly Ser Phe Leu Met Asn Ile Gln Glu Leu Ala Leu Ile Arg Ile Glu
            515                 520                 525

Asn Leu Pro Val Lys Val Met Val Leu Asn Asn Gln His Leu Gly Met
530                 535                 540

Val Val Gln Trp Glu Asp Arg Phe Tyr Lys Ala Asn Arg Ala His Thr
545                 550                 555                 560

Tyr Leu Gly Asn Pro Glu Cys Glu Ser Glu Ile Tyr Pro Asp Phe Val
            565                 570                 575

Thr Ile Ala Lys Gly Phe Asn Ile Pro Ala Val Arg Val Thr Lys Lys
            580                 585                 590

Ser Glu Val Arg Ala Ala Ile Lys Lys Met Leu Glu Thr Pro Gly Pro
            595                 600                 605

Tyr Leu Leu Asp Ile Ile Val Pro His Gln Glu His Val Leu Pro Met
            610                 615                 620

Ile Pro Ile Gly Gly Ala Phe Lys Asp Met Ile Leu Asp Gly Asp Gly
625                 630                 635                 640

Arg Thr Val Tyr

<210> SEQ ID NO 7

-continued

```
<211> LENGTH: 2294
<212> TYPE: DNA
<213> ORGANISM: Oryza sativa var. kinmaze
<220> FEATURE:
<221> NAME/KEY: CDS
<222> LOCATION: (48)..(1979)

<400> SEQUENCE: 7
```

| | | | | | | | | | | | | | | |
|---|---|---|---|---|---|---|---|---|---|---|---|---|---|---|
| cccaaaccca | gaaaccctcg | ccgccgccgc | cgccgccacc | acccacc | atg Met 1 | gct Ala | acg Thr | | | | | | | 56 |
| acc Thr | gcc Ala 5 | gcg Ala | gcc Ala | gcg Ala | gcc Ala 10 | gcc Ala | gcc Ala | ctg Leu | tcc Ser | gcc Ala 15 | gcc Ala | gcg Ala | acg Thr | gcc Ala | aag Lys | 104 |
| acc Thr 20 | ggc Gly | cgt Arg | aag Lys | aac Asn | cac His 25 | cag Gln | cga Arg | cac His | cac His | gtc Val 30 | ctt Leu | ccc Pro | gct Ala | cga Arg | ggc Gly 35 | 152 |
| cgg Arg | gtg Val | ggg Gly | gcg Ala 40 | gcg Ala | gcg Ala | gtc Val | agg Arg | tgc Cys 45 | tcg Ser | gcg Ala | gtg Val | tcc Ser | ccg Pro 50 | gtc Val | acc Thr | 200 |
| ccg Pro | ccg Pro | tcc Ser 55 | ccg Pro | gcg Ala | ccg Pro | ccg Pro | gcc Ala 60 | acg Thr | ccg Pro | ctc Leu | cgg Arg | ccg Pro 65 | tgg Trp | ggg Gly | ccg Pro | 248 |
| gcc Ala | gag Glu 70 | ccc Pro | cgc Arg | aag Lys | ggc Gly | gcg Ala 75 | gac Asp | atc Ile | ctc Leu | gtg Val | gag Glu 80 | gcg Ala | ctg Leu | gag Glu | cgg Arg | 296 |
| tgc Cys 85 | ggc Gly | gtc Val | agc Ser | gac Asp | gtg Val 90 | ttc Phe | gcc Ala | tac Tyr | ccg Pro | ggc Gly 95 | ggc Gly | gcg Ala | tcc Ser | atg Met | gag Glu | 344 |
| atc Ile 100 | cac His | cag Gln | gcg Ala | ctg Leu | acg Thr 105 | cgc Arg | tcc Ser | ccg Pro | gtc Val | atc Ile 110 | acc Thr | aac Asn | cac His | ctc Leu | ttc Phe 115 | 392 |
| cgc Arg | cac His | gag Glu | cag Gln | ggc Gly 120 | gag Glu | gcg Ala | ttc Phe | gcg Ala | gcg Ala 125 | tcc Ser | ggg Gly | tac Tyr | gcg Ala | cgc Arg 130 | gcg Ala | 440 |
| tcc Ser | ggc Gly | cgc Arg | gtc Val 135 | ggg Gly | gtc Val | tgc Cys | gtc Val | gcc Ala 140 | acc Thr | tcc Ser | ggc Gly | ccc Pro | ggg Gly 145 | gca Ala | acc Thr | 488 |
| aac Asn | ctc Leu | gtg Val 150 | tcc Ser | gcg Ala | ctc Leu | gcc Ala | gac Asp 155 | gcg Ala | ctg Leu | ctc Leu | gac Asp | tcc Ser 160 | gtc Val | ccg Pro | atg Met | 536 |
| gtc Val | gcc Ala 165 | atc Ile | acg Thr | ggc Gly | cag Gln | gtc Val 170 | cac His | cgc Arg | cgc Arg | atg Met | atc Ile 175 | ggc Gly | acc Thr | gac Asp | gcc Ala | 584 |
| ttc Phe | cag Gln 180 | gag Glu | acg Thr | ccc Pro | ata Ile | gtc Val 185 | gag Glu | gtc Val | acc Thr | cgc Arg | tcc Ser 190 | atc Ile | acc Thr | aag Lys | cac His 195 | 632 |
| aat Asn | tac Tyr | ctt Leu | gtc Val | ctt Leu 200 | gat Asp | gtg Val | gag Glu | gac Asp | atc Ile 205 | ccc Pro | cgc Arg | gtc Val | ata Ile | cag Gln 210 | gaa Glu | 680 |
| gcc Ala | ttc Phe | ttc Phe | ctc Leu 215 | gcg Ala | tcc Ser | tcg Ser | ggc Gly | cgt Arg 220 | cct Pro | ggc Gly | ccg Pro | gtg Val | ctg Leu 225 | gtc Val | gac Asp | 728 |
| atc Ile | ccc Pro | aag Lys 230 | gac Asp | atc Ile | cag Gln | cag Gln | cag Gln 235 | atg Met | gcc Ala | gtg Val | ccg Pro | gtc Val 240 | tgg Trp | gac Asp | acc Thr | 776 |
| tcg Ser | atg Met 245 | aat Asn | cta Leu | cca Pro | ggg Gly | tac Tyr 250 | atc Ile | gca Ala | cgc Arg | ctg Leu | ccc Pro 255 | aag Lys | cca Pro | ccc Pro | gcg Ala | 824 |
| aca Thr 260 | gaa Glu | ttg Leu | ctt Leu | gag Glu | cag Gln 265 | gtc Val | ttg Leu | cgt Arg | ctg Leu | gtt Val 270 | ggc Gly | gag Glu | tca Ser | cgg Arg | cgc Arg 275 | 872 |

```
ccg att ctc tat gtc ggt ggt ggc tgc tct gca tct ggt gac gaa ttg      920
Pro Ile Leu Tyr Val Gly Gly Gly Cys Ser Ala Ser Gly Asp Glu Leu
            280                 285                 290 cgc tgg ttt gtt gag ctg act ggt atc cca gtt aca acc act ctg atg      968
Arg Trp Phe Val Glu Leu Thr Gly Ile Pro Val Thr Thr Thr Leu Met
        295                 300                 305 ggc ctc ggc aat ttc ccc agt gac gac ccg ttg tcc ctg cgc atg ctt     1016
Gly Leu Gly Asn Phe Pro Ser Asp Asp Pro Leu Ser Leu Arg Met Leu
    310                 315                 320 ggg atg cat ggc acg gtg tac gca aat tat gcc gtg gat aag gct gac     1064
Gly Met His Gly Thr Val Tyr Ala Asn Tyr Ala Val Asp Lys Ala Asp
325                 330                 335 ctg ttg ctt gcg ttt ggt gtg cgg ttt gat gat cgt gtg aca ggg aaa     1112
Leu Leu Leu Ala Phe Gly Val Arg Phe Asp Asp Arg Val Thr Gly Lys
340                 345                 350                 355 att gag gct ttt gca agc agg gcc aag att gtg cac att gac att gat     1160
Ile Glu Ala Phe Ala Ser Arg Ala Lys Ile Val His Ile Asp Ile Asp
                360                 365                 370 cca gca gag att gga aag aac aag caa cca cat gtg tca att tgc gca     1208
Pro Ala Glu Ile Gly Lys Asn Lys Gln Pro His Val Ser Ile Cys Ala
            375                 380                 385 gat gtt aag ctt gct tta cag ggc ttg aat gct ctg cta caa cag agc     1256
Asp Val Lys Leu Ala Leu Gln Gly Leu Asn Ala Leu Leu Gln Gln Ser
        390                 395                 400 aca aca aag aca agt tct gat ttt agt gca tgg cac aat gag ttg gac     1304
Thr Thr Lys Thr Ser Ser Asp Phe Ser Ala Trp His Asn Glu Leu Asp
    405                 410                 415 cag cag aag agg gag ttt cct ctg ggg tac aaa act ttt ggt gaa gag     1352
Gln Gln Lys Arg Glu Phe Pro Leu Gly Tyr Lys Thr Phe Gly Glu Glu
420                 425                 430                 435 atc cca ccg caa tat gcc att cag gtg ctg gat gag ctg acg aaa ggt     1400
Ile Pro Pro Gln Tyr Ala Ile Gln Val Leu Asp Glu Leu Thr Lys Gly
                440                 445                 450 gag gca atc atc gct act ggt gtt ggg cag cac cag atg tgg gcg gca     1448
Glu Ala Ile Ile Ala Thr Gly Val Gly Gln His Gln Met Trp Ala Ala
            455                 460                 465 caa tat tac acc tac aag cgg cca cgg cag tgg ctg tct tcg gct ggt     1496
Gln Tyr Tyr Thr Tyr Lys Arg Pro Arg Gln Trp Leu Ser Ser Ala Gly
        470                 475                 480 ctg ggc gca atg gga ttt ggg ctg cct gct gca gct ggt gct tct gtg     1544
Leu Gly Ala Met Gly Phe Gly Leu Pro Ala Ala Ala Gly Ala Ser Val
    485                 490                 495 gct aac cca ggt gtc aca gtt gtt gat att gat ggg gat ggt agc ttc     1592
Ala Asn Pro Gly Val Thr Val Val Asp Ile Asp Gly Asp Gly Ser Phe
500                 505                 510                 515 ctc atg aac att cag gag ctg gca ttg atc cgc att gag aac ctc cct     1640
Leu Met Asn Ile Gln Glu Leu Ala Leu Ile Arg Ile Glu Asn Leu Pro
                520                 525                 530 gtg aag gtg atg gtg ttg aac aac caa cat ttg ggt atg gtg gtg caa     1688
Val Lys Val Met Val Leu Asn Asn Gln His Leu Gly Met Val Val Gln
            535                 540                 545 ttg gag gat agg ttt tac aag gcg aat agg gcg cat aca tac ttg ggc     1736
Leu Glu Asp Arg Phe Tyr Lys Ala Asn Arg Ala His Thr Tyr Leu Gly
        550                 555                 560 aac ccg gaa tgt gag agc gag ata tat cca gat ttt gtg act att gct     1784
Asn Pro Glu Cys Glu Ser Glu Ile Tyr Pro Asp Phe Val Thr Ile Ala
    565                 570                 575 aag ggg ttc aat att cct gca gtc cgt gta aca aag aag agt gaa gtc     1832
Lys Gly Phe Asn Ile Pro Ala Val Arg Val Thr Lys Lys Ser Glu Val
580                 585                 590                 595
```

-continued

```
cgt gcc gcc atc aag aag atg ctc gag act cca ggg cca tac ttg ttg      1880
Arg Ala Ala Ile Lys Lys Met Leu Glu Thr Pro Gly Pro Tyr Leu Leu
            600                 605                 610 gat atc atc gtc ccg cac cag gag cat gtg ctg cct atg atc cca att      1928
Asp Ile Ile Val Pro His Gln Glu His Val Leu Pro Met Ile Pro Ile
            615                 620                 625 ggg ggc gca ttc aag gac atg atc ctg gat ggt gat ggc agg act gtg      1976
Gly Gly Ala Phe Lys Asp Met Ile Leu Asp Gly Asp Gly Arg Thr Val
            630                 635                 640 tat taatctataa tctgtatgtt ggcaaagcac cagcccggcc tatgtttgac           2029
Tyr ctgaatgacc cataaagagt ggtatgccta tgatgtttgt atgtgctcta tcaataacta   2089
aggtgtcaac tatgaaccat atgctcttct gttttacttg tttgatgtgc ttggcatggt   2149
aatcctaatt agcttcctgc tgtctaggtt tgtagtgtgt tgttttctgt aggcatatgc   2209
atcacaagat atcatgtaag tttcttgtcc tacatatcaa taataagaga ataaagtact   2269
tctatgtaaa aaaaaaaaaa aaaaa                                          2294

<210> SEQ ID NO 8
<211> LENGTH: 644
<212> TYPE: PRT
<213> ORGANISM: Oryza sativa var. kinmaze

<400> SEQUENCE: 8

Met Ala Thr Thr Ala Ala Ala Ala Ala Leu Ser Ala Ala
1               5                   10              15

Thr Ala Lys Thr Gly Arg Lys Asn His Gln Arg His Val Leu Pro
                20                  25                  30

Ala Arg Gly Arg Val Gly Ala Ala Val Arg Cys Ser Ala Val Ser
            35                  40                  45

Pro Val Thr Pro Pro Ser Pro Ala Pro Pro Ala Thr Pro Leu Arg Pro
        50                  55                  60

Trp Gly Pro Ala Glu Pro Arg Lys Gly Ala Asp Ile Leu Val Glu Ala
65                  70                  75                  80

Leu Glu Arg Cys Gly Val Ser Asp Val Phe Ala Tyr Pro Gly Gly Ala
                85                  90                  95

Ser Met Glu Ile His Gln Ala Leu Thr Arg Ser Pro Val Ile Thr Asn
            100                 105                 110

His Leu Phe Arg His Glu Gln Gly Glu Ala Phe Ala Ala Ser Gly Tyr
        115                 120                 125

Ala Arg Ala Ser Gly Arg Val Gly Val Cys Val Ala Thr Ser Gly Pro
    130                 135                 140

Gly Ala Thr Asn Leu Val Ser Ala Leu Ala Asp Ala Leu Leu Asp Ser
145                 150                 155                 160

Val Pro Met Val Ala Ile Thr Gly Gln Val His Arg Arg Met Ile Gly
                165                 170                 175

Thr Asp Ala Phe Gln Glu Thr Pro Ile Val Glu Val Thr Arg Ser Ile
            180                 185                 190

Thr Lys His Asn Tyr Leu Val Leu Asp Val Glu Asp Ile Pro Arg Val
        195                 200                 205

Ile Gln Glu Ala Phe Phe Leu Ala Ser Ser Gly Arg Pro Gly Pro Val
    210                 215                 220

Leu Val Asp Ile Pro Lys Asp Ile Gln Gln Gln Met Ala Val Pro Val
225                 230                 235                 240

Trp Asp Thr Ser Met Asn Leu Pro Gly Tyr Ile Ala Arg Leu Pro Lys
```

```
                    245                 250                 255
Pro Pro Ala Thr Glu Leu Leu Glu Gln Val Leu Arg Leu Val Gly Glu
                260                 265                 270

Ser Arg Arg Pro Ile Leu Tyr Val Gly Gly Cys Ser Ala Ser Gly
            275                 280                 285

Asp Glu Leu Arg Trp Phe Val Glu Leu Thr Gly Ile Pro Val Thr Thr
            290                 295                 300

Thr Leu Met Gly Leu Gly Asn Phe Pro Ser Asp Pro Leu Ser Leu
305                 310                 315                 320

Arg Met Leu Gly Met His Gly Thr Val Tyr Ala Asn Tyr Ala Val Asp
                325                 330                 335

Lys Ala Asp Leu Leu Ala Phe Gly Val Arg Phe Asp Asp Arg Val
            340                 345                 350

Thr Gly Lys Ile Glu Ala Phe Ala Ser Arg Ala Lys Ile Val His Ile
            355                 360                 365

Asp Ile Asp Pro Ala Glu Ile Gly Lys Asn Lys Gln Pro His Val Ser
370                 375                 380

Ile Cys Ala Asp Val Lys Leu Ala Leu Gln Gly Leu Asn Ala Leu Leu
385                 390                 395                 400

Gln Gln Ser Thr Thr Lys Thr Ser Ser Asp Phe Ser Ala Trp His Asn
                405                 410                 415

Glu Leu Asp Gln Gln Lys Arg Glu Phe Pro Leu Gly Tyr Lys Thr Phe
            420                 425                 430

Gly Glu Glu Ile Pro Pro Gln Tyr Ala Ile Gln Val Leu Asp Glu Leu
            435                 440                 445

Thr Lys Gly Glu Ala Ile Ile Ala Thr Gly Val Gly Gln His Gln Met
450                 455                 460

Trp Ala Ala Gln Tyr Tyr Thr Tyr Lys Arg Pro Arg Gln Trp Leu Ser
465                 470                 475                 480

Ser Ala Gly Leu Gly Ala Met Gly Phe Gly Leu Pro Ala Ala Ala Gly
                485                 490                 495

Ala Ser Val Ala Asn Pro Gly Val Thr Val Val Asp Ile Asp Gly Asp
            500                 505                 510

Gly Ser Phe Leu Met Asn Ile Gln Glu Leu Ala Leu Ile Arg Ile Glu
            515                 520                 525

Asn Leu Pro Val Lys Val Met Val Leu Asn Asn Gln His Leu Gly Met
            530                 535                 540

Val Val Gln Leu Glu Asp Arg Phe Tyr Lys Ala Asn Arg Ala His Thr
545                 550                 555                 560

Tyr Leu Gly Asn Pro Glu Cys Glu Ser Glu Ile Tyr Pro Asp Phe Val
                565                 570                 575

Thr Ile Ala Lys Gly Phe Asn Ile Pro Ala Val Arg Val Thr Lys Lys
            580                 585                 590

Ser Glu Val Arg Ala Ala Ile Lys Lys Met Leu Glu Thr Pro Gly Pro
            595                 600                 605

Tyr Leu Leu Asp Ile Ile Val Pro His Gln Glu His Val Leu Pro Met
610                 615                 620

Ile Pro Ile Gly Gly Ala Phe Lys Asp Met Ile Leu Asp Gly Asp Gly
625                 630                 635                 640

Arg Thr Val Tyr

<210> SEQ ID NO 9
<211> LENGTH: 21
<212> TYPE: DNA
```

```
<213> ORGANISM: Artificial Sequence
<220> FEATURE:
<223> OTHER INFORMATION: Description of Artificial Sequence: synthetic
      oligonucleotide primer

<400> SEQUENCE: 9
gctctgctac aacagagcac a                                              21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: synthetic
      oligonucleotide primer

<400> SEQUENCE: 10
agtcctgcca tcaccatcca g                                              21

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: synthetic
      oligonucleotide primer

<400> SEQUENCE: 11
ctgggacacc tcgatgaat                                                 19

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: synthetic
      oligonucleotide primer

<400> SEQUENCE: 12
caacaaacca gcgcaattcg tcacc                                          25

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: synthetic
      oligonucleotide primer

<400> SEQUENCE: 13
catcaccaac cacctctt                                                  18

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: synthetic
      oligonucleotide primer

<400> SEQUENCE: 14
aactgggata ccagtcagct c                                              21

<210> SEQ ID NO 15
<211> LENGTH: 16
<212> TYPE: DNA
<213> ORGANISM: Artificial Sequence
<220> FEATURE:
```

```
<223> OTHER INFORMATION: Description of Artificial Sequence: synthetic
      oligonucleotide primer

<400> SEQUENCE: 15
tgtgcttggt gatgga                                                         16

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide primer

<400> SEQUENCE: 16
tcaaggacat gatcctggat gg                                                  22

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: synthetic
      oligonucleotide primer

<400> SEQUENCE: 17
cagcgacgtg ttcgccta                                                       18

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: synthetic
      oligonucleotide primer

<400> SEQUENCE: 18
ccaccgacat agagaatc                                                       18

<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence: synthetic
      oligonucleotide primer

<400> SEQUENCE: 19
acacggactg caggaata                                                       18

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence: synthetic
      oligonucleotide primer

<400> SEQUENCE: 20
ttacaaggcg aatagggc                                                       18

<210> SEQ ID NO 21
<211> LENGTH: 17
<212> TYPE: DNA
<213> ORGANISM: Artificial Sequence
<220> FEATURE:
<223> OTHER INFORMATION: Description of Artificial Sequence: synthetic
      oligonucleotide primer
```

```
<400> SEQUENCE: 21
gcatcttctt gatggcg                                                    17

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence: synthetic
      oligonucleotide primer

<400> SEQUENCE: 22
atgcatggca cggtgtac                                                   18

<210> SEQ ID NO 23
<211> LENGTH: 17
<212> TYPE: DNA
<213> ORGANISM: Artificial Sequence
<220> FEATURE:
<223> OTHER INFORMATION: Description of Artificial Sequence: synthetic
      oligonucleotide primer

<400> SEQUENCE: 23
gattgcctca cctttcg                                                    17

<210> SEQ ID NO 24
<211> LENGTH: 17
<212> TYPE: DNA
<213> ORGANISM: Artificial Sequence
<220> FEATURE:
<223> OTHER INFORMATION: Description of Artificial Sequence: synthetic
      oligonucleotide primer

<400> SEQUENCE: 24
aggtgtcaca gttgttg                                                    17

<210> SEQ ID NO 25
<211> LENGTH: 17
<212> TYPE: DNA
<213> ORGANISM: Artificial Sequence
<220> FEATURE:
<223> OTHER INFORMATION: Description of Artificial Sequence: synthetic
      oligonucleotide primer

<400> SEQUENCE: 25
agaggtggtt ggtgatg                                                    17

<210> SEQ ID NO 26
<211> LENGTH: 17
<212> TYPE: DNA
<213> ORGANISM: Artificial Sequence
<220> FEATURE:
<223> OTHER INFORMATION: Description of Artificial Sequence: synthetic
      oligonucleotide primer

<400> SEQUENCE: 26
gctttgccaa catacag                                                    17

<210> SEQ ID NO 27
<211> LENGTH: 17
<212> TYPE: DNA
<213> ORGANISM: Artificial Sequence
<220> FEATURE:
<223> OTHER INFORMATION: Description of Artificial Sequence: synthetic
      oligonucleotide primer

<400> SEQUENCE: 27
```

```
cagcccaaat cccattg                                               17
```

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence: synthetic
      oligonucleotide primer

<400> SEQUENCE: 28

```
atgtaccctg gtagattc                                              18
```

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide primer
<220> FEATURE:
<221> NAME/KEY: misc_feature
<222> LOCATION: (3)..(3)
<223> OTHER INFORMATION: n is Inosine
<220> FEATURE:
<221> NAME/KEY: misc_feature
<222> LOCATION: (9)..(9)
<223> OTHER INFORMATION: n is Inosine
<220> FEATURE:
<221> NAME/KEY: misc_feature
<222> LOCATION: (15)..(15)
<223> OTHER INFORMATION: n is Inosine
<220> FEATURE:
<221> NAME/KEY: misc_feature
<222> LOCATION: (18)..(18)
<223> OTHER INFORMATION: n is a, c, g, or t

<400> SEQUENCE: 29

```
gtnttygcnt ayccnggngg                                            20
```

<210> SEQ ID NO 30
<211> LENGTH: 19
<212> TYPE: DNA
<213> ORGANISM: Artificial Sequence
<220> FEATURE:
<223> OTHER INFORMATION: Description of Artificial Sequence: synthetic
      oligonucleotide primer

<400> SEQUENCE: 30

```
ggaaacagct atgaccatg                                             19
```

<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide primer

<400> SEQUENCE: 31

```
ccgggagctg catgtgtcag agg                                        23
```

<210> SEQ ID NO 32
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide primer

```
<400> SEQUENCE: 32
gggctggcaa gccacgtttg gtg                                           23

<210> SEQ ID NO 33
<211> LENGTH: 30
<212> TYPE: DNA
<213> ORGANISM: Artificial Sequence
<220> FEATURE:
<223> OTHER INFORMATION: Description of Artificial Sequence: synthetic
      oligonucleotide primer

<400> SEQUENCE: 33
ccccagccgc atgatcggca ccgacgcctt                                    30

<210> SEQ ID NO 34
<211> LENGTH: 27
<212> TYPE: DNA
<213> ORGANISM: Artificial Sequence
<220> FEATURE:
<223> OTHER INFORMATION: Description of Artificial Sequence: synthetic
      oligonucleotide primer

<400> SEQUENCE: 34
cggtgccgat catgcggctg gggacct                                       27

<210> SEQ ID NO 35
<211> LENGTH: 1403
<212> TYPE: DNA
<213> ORGANISM: Nippon-bare

<400> SEQUENCE: 35
acccacgcgt ccgatgtgga ggacatcccc cgcgtcatac aggaagcctt cttcctcgcg    60
tcctcgggcc gtcctggccc ggtgctggtc gacatcccca ggacatcca gcagcagatg   120 gccgtgccgg tctgggacac ctcgatgaat ctaccaggtg acatcgcacg cctgcccaag   180
ccacccgcga cagaattgct tgagcaggtc ttgcgtctgg ttggcgagtc acggcgcccg   240
attctctatg tcggtggtgg ctgctctgca tctggtgacg aattgcgctg gtttgttgag   300
ctgactggta tcccagttac aaccactctg atgggcctcg gcaatttccc cagtgacgac   360
ccgttgtccc tgcgcatgct tgggatgcat ggcacggtgt acgcaaatta tgccgtggat   420
aaggctgacc tgttgcttgc gtttggtgtg cggtttgatg atcgtgtgac agggaaaatt   480
gaggcttttg caagcagggc caagattgtg cacattgaca ttgatccagc agagattgga   540
aagaacaagc aaccacatgt gtcaatttgc gcagatgtta agcttgcttt acagggcttg   600
aatgctctgc tacaacagag cacaacaaag acaagttctg atttagtgc atggcacaat   660 gagttggacc agcagaagag ggagtttcct ctggggtaca aaacttttgg tgaagagatc   720
ccaccgcaat atgccattca ggtgctggat gagctgacga aggtgaggc aatcatcgct   780 actggtgttg gcagcacca gatgtgggcg gcacaatatt acacctacaa gcggccacgg   840
cagtggctgt cttcggctgg tctgggcgca atgggatttg gctgcctgc tgcagctggt   900 gcttctgtgg ctaacccagg tgtcacagtt gttgatattg atgggatgg tagcttcctc   960 atgaacattc aggagctggc attgatccgc attgagaacc tccctgtgaa ggtgatggtg  1020
ttgaacaacc aacatttggg tatggtggtg caatgggagg ataggtttta caaggcgaat  1080
agggcgcata catacttggg caacccggaa tgtgagagcg agatatatcc agattttgtg  1140
acctattgct aaggggttca atattcctgc agtccgtgta acaaagaaga gtgaagtccg  1200
tgccgccatc aagaagatgc tcgagactcc agggccatac ttgttggata tcatcgtccc  1260
```

```
gcaccaggag catgtgctgc ctatgatccc aagtgggggc gcattcaagg acatgatcct    1320
ggatggtgat ggcaggactg tgtattaatc tataatctgt atgttggcaa agcaccagcc    1380
cggcctatgt ttgacctgaa tga                                            1403
```

<210> SEQ ID NO 36
<211> LENGTH: 1404
<212> TYPE: DNA
<213> ORGANISM: Maize

<400> SEQUENCE: 36

```
catcgtcgag gtcacccgct ccatcaccaa gcacaactac ctggtcctcg acgtcgacga      60
catcccccgc gtcgtgcagg aggccttctt cctcgcatcc tctggtcgcc ggggccggt     120 gcttgttgac atccccaagg acatccagca gcagatggcg gtgccggcct gggacacgcc    180
catgagtctg cctgggtaca tcgcgcgcct tcccaagcct cccgcgactg aatttcttga    240
gcaggtgctg cgtcttgttg gtgaatcacg gcgccctgtt ctttatgttg gcggtggctg    300
tgcagcatca ggtgaggagt tgtgccgctt tgtggagttg actggaatcc cagtcacaac    360
tactcttatg ggccttggca acttccccag cgacgaccca ctgtcactgc gcatgcttgg    420
tatgcatggc acagtgtatg caaattatgc agtggataag gccgatctgt tgcttgcatt    480
tggtgtgcgg tttgatgatc gtgtgacagg gaaaattgag gcttttgcag gcagagctaa    540
gattgtgcac attgatattg atcctgctga gattggcaag aacaagcagc acatgtgtc     600 catctgtgca gatgttaagc ttgctttgca gggcatgaat actcttctgg aaggaagcac    660
atcaaagaag agctttgact tcggctcatg gcatgatgaa ttggatcagc aaaagaggga    720
gtttcccctt ggatataaaa tcttcaatga ggaaatccag ccacaatatg ctattcaggt    780
tcttgatgag ttgacgaagg gggaggccat cattgccaca ggtgttgggc agcaccagat    840
gtgggcggca cagtattaca cttacaagcg gccaaggcag tggctgtctt cagctggtct    900
tggggctatg ggatttggtt tgccggctgc tgctggtgct gctgtggcca acccaggtgt    960
cactgttgtt gacatcgacg gagatggtag cttcctcatg aacattcagg agctagctat   1020
gatccgtatt gagaacctcc cagtcaaggt ctttgtgcta acaaccagc acctcgggat    1080 ggtggtgcag tgggaggaca ggttctataa ggccaataga gcacacacat tcttgggaaa   1140
cccagagaac gaaagtgaga tatatccaga ttttgtggca attgctaaag ggttcaacat   1200
tccagcagtc cgtgtgacaa agaagagcga agtccatgca gcaatcaaga agatgcttga   1260
ggctccaggg ccgtacctct tggatataat cgtcccgcac caggagcatg tgttgcctat   1320
gatccctagt ggtggggctt tcaaggatat gatcctggat ggtgatggca ggactgtgta   1380
ttgatccgtt gactgcaggt cgac                                           1404
```

<210> SEQ ID NO 37
<211> LENGTH: 2279
<212> TYPE: DNA
<213> ORGANISM: Oryza sativa

<400> SEQUENCE: 37

```
ctcgccgccg ccgccgccgc caccacccac catggctacg accgccgcgg ccgcggccgc      60
cgccctgtcc gccgccgcga cggccaagac cggccgtaag aaccaccagc gacaccacgt     120
ccttcccgct cgaggccggg tgggggcggc ggcggtcagg tgctcggcgg tgtccccggt     180 cacccgccg tccccggcgc cgccggccac gccgctccgg ccgtggggc cggccgagcc      240 ccgcaagggc gcggacatcc tcgtggaggc gctggagcgg tgcggcgtca gcgacgtgtt     300
```

```
cgcctacccg ggcggcgcgt ccatggagat ccaccaggcg ctgacgcgct ccccggtcat      360
caccaaccac ctcttccgcc acgagcaggg cgaggcgttc gcggcgtccg ggtacgcgcg      420
cgcgtccggc cgcgtcgggg tctgcgtcgc cacctccggc cccggggcaa ccaacctcgt      480
gtccgcgctc gccgacgcgc tgctcgactc cgtcccgatg gtcgccatca cgggccaggt      540
cccccgccgc atgatcggca ccgacgcctt ccaggagacg cccatagtcg aggtcacccg      600
ctccatcacc aagcacaatt accttgtcct tgatgtggag acatccccc gcgtcataca      660 ggaagccttc ttcctcgcgt cctcgggccg tcctggcccg gtgctggtcg acatccccaa      720
ggacatccag cagcagatgg ccgtgccggt ctgggacacc tcgatgaatc taccagggta      780
catcgcacgc ctgcccaagc cacccgcgac agaattgctt gagcaggtct tgcgtctggt      840
tggcgagtca cggcgcccga ttctctatgt cggtggtggc tgctctgcat ctggtgacga      900
attgcgctgg tttgttgagc tgactggtat cccagttaca accactctga tgggcctcgg      960
caatttcccc agtgacgacc cgttgtccct gcgcatgctt gggatgcatg cacggtgta      1020 cgcaaattat gccgtggata aggctgacct gttgcttgcg tttggtgtgc ggtttgatga     1080
tcgtgtgaca gggaaaattg aggcttttgc aagcagggcc aagattgtgc acattgacat     1140
tgatccagca gagattggaa agaacaagca accacatgtg tcaatttgcg cagatgttaa     1200
gcttgcttta cagggcttga atgctctgct acaacagagc acaacaaaga caagttctga     1260
ttttagtgca tggcacaatg agttggacca gcagaagagg gagtttcctc tggggtacaa     1320 aactttggt gaagagatcc caccgcaata tgccattcag gtgctggatg agctgacgaa      1380
aggtgaggca atcatcgcta ctggtgttgg gcagcaccag atgtgggcgg cacaatatta     1440
cacctacaag cggccacggc agtggctgtc ttcggctggt ctgggcgcaa tgggatttgg     1500
gctgcctgct gcagctggtg cttctgtggc taacccaggt gtcacagttg ttgatattga     1560 tgggatggt agcttcctca tgaacattca ggagctggca ttgatccgca ttgagaacct     1620
ccctgtgaag gtgatggtgt tgaacaacca acatttgggt atggtggtgc aattggagga     1680
taggttttac aaggcgaata gggcgcatac atacttgggc aacccggaat gtgagagcga     1740
gatatatcca gattttgtga ctattgctaa ggggttcaat attcctgcag tccgtgtaac     1800
aaagaagagt gaagtccgtg ccgccatcaa gaagatgctc gagactccag gccatactt     1860 gttggatatc atcgtcccgc accaggagca tgtgctgcct atgatcccaa ttggggcgc     1920 attcaaggac atgatcctgg atggtgatgg caggactgtg tattaatcta taatctgtat     1980
gttggcaaag caccagcccg gcctatgttt gacctgaatg acccataaag agtggtatgc     2040
ctatgatgtt tgtatgtgct ctatcaataa ctaaggtgtc aactatgaac catatgctct     2100
tctgttttac ttgtttgatg tgcttggcat ggtaatccta attagcttcc tgctgtctag     2160
gtttgtagtg tgttgttttc tgtaggcata tgcatcacaa gatatcatgt aagtttcttg     2220
tcctacatat caataataag agaataaagt acttctatgt aaaaaaaaaa aaaaaaaa      2279
```

<210> SEQ ID NO 38
<211> LENGTH: 2301
<212> TYPE: DNA
<213> ORGANISM: Oryza sativa

<400> SEQUENCE: 38

```
cccaaaccca gaaaccctcg ccgccgccgc cgccgccacc acccaccatg gctacgaccg       60
ccgcggccgc ggccgccgcc ctgtccgccg ccgcgacggc caagaccggc cgtaagaacc      120
accagcgaca ccacgtccct cccgctcgag gccgggtggg ggcggcggcg gtcaggtgct      180
```

```
cggcggtgtc cccggtcacc ccgccgtccc cggcgccgcc ggccacgccg ctccggccgt    240
gggggccggc cgagccccgc aagggcgcgg acatcctcgt ggaggcgctg gagcggtgcg    300
gcgtcagcga cgtgttcgcc tacccgggcg cgcgtccat ggagatccac caggcgctga    360
cgcgctcccc ggtcatcacc aaccacctct tccgccacga gcagggcgag gcgttcgcgg    420
cgtccgggta cgcgcgcgcg tccggccgcg tcggggtctg cgtcgccacc tccggccccg    480
gggcaaccaa cctcgtgtcc gcgctcgccg acgcgctgct cgactccgtc ccgatggtcg    540
ccatcacggg ccaggtcccc cgccgcatga tcggcaccga cgccttccag gagacgccca    600
tagtcgaggt caccccgctcc atcaccaagc acaattacct tgtccttgat gtggaggaca    660
tccccccgcgt catacaggaa gccttcttcc tcgcgtcctc gggccgtcct ggcccggtgc    720
tggtcgacat ccccaaggac atccagcagc agatggccgt gccggtctgg gacacctcga    780
tgaatctacc agggtacatc gcacgcctgc ccaagccacc cgcgacagaa ttgcttgagc    840
aggtcttgcg tctggttggc gagtcacggc gcccgattct ctatgtcggt ggtggctgct    900
ctgcatctgg tgacgaattg cgctggtttg ttgagctgac tggtatccca gttacaacca    960
ctctgatggg cctcggcaat ttccccagtg acgacccgtt gtccctgcgc atgcttggga   1020
tgcatggcac ggtgtacgca aattatgccg tggataaggc tgacctgttg cttgcgtttg   1080
gtgtgcggtt tgatgatcgt gtgacaggga aaattgaggc ttttgcaagc agggccaaga   1140
ttgtgcacat tgacattgat ccagcagaga ttggaaagaa caagcaacca catgtgtcaa   1200
tttgcgcaga tgttaagctt gctttacagg gcttgaatgc tctgctacaa cagagcacaa   1260
caaagacaag ttctgatttt agtgcatggc acaatgagtt ggaccagcag aagagggagt   1320
ttcctctggg gtacaaaact tttggtgaag agatcccacc gcaatatgcc attcaggtgc   1380
tggatgagct gacgaaaggt gaggcaatca tcgctactgg tgttgggcag caccagatgt   1440
gggcggcaca atattacacc tacaagcggc cacggcagtg gctgtcttcg gctggtctgg   1500
gcgcaatggg atttgggctg cctgctgcag ctggtgcttc tgtggctaac ccaggtgtca   1560
cagttgttga tattgatggg gatggtagct tcctcatgaa cattcaggag ctggcattga   1620
tccgcattga gaacctccct gtgaaggtga tggtgttgaa caaccaacat ttgggtatgg   1680
tggtgcaatg ggaggatagg ttttacaagg cgaatagggc gcatacatac ttgggcaacc   1740
cggaatgtga gagcgagata tatccagatt ttgtgactat tgctaagggg ttcaatattc   1800
ctgcagtccg tgtaacaaag aagagtgaag tccgtgccgc catcaagaag atgctcgaga   1860
ctccagggcc atacttgttg gatatcatcg tcccgcacca ggagcatgtg ctgcctatga   1920
tcccaagtgg gggcgcattc aaggacatga tcctggatgg tgatggcagg actgtgtatt   1980
aatctataat ctgtatgttg gcaaagcacc agcccggcct atgtttgacc tgaatgaccc   2040
ataaagagtg gtatgcctat gatgtttgta tgtgctctat caataactaa ggtgtcaact   2100
atgaaccata tgctcttctg ttttacttgt ttgatgtgct tggcatggta atcctaatta   2160
gcttcctgct gtctaggttt gtagtgtgtt gttttctgta ggcatatgca tcacaagata   2220
tcatgtaagt ttcttgtcct acatatcaat aataagagaa taaagtactt ctatgcaaaa   2280
aaaaaaaaaa aaaaaaaaaa a                                              2301
```

<210> SEQ ID NO 39  
<211> LENGTH: 644  
<212> TYPE: PRT  
<213> ORGANISM: Oryza sativa
<400> SEQUENCE: 39

-continued

```
Met Ala Thr Thr Ala Ala Ala Ala Ala Leu Ser Ala Ala
1               5               10              15

Thr Ala Lys Thr Gly Arg Lys Asn His Gln Arg His His Val Leu Pro
            20                  25                  30

Ala Arg Gly Arg Val Gly Ala Ala Val Arg Cys Ser Ala Val Ser
        35                  40                  45

Pro Val Thr Pro Pro Ser Pro Ala Pro Pro Ala Thr Pro Leu Arg Pro
        50                  55                  60

Trp Gly Pro Ala Glu Pro Arg Lys Gly Ala Asp Ile Leu Val Glu Ala
65                      70                  75                  80

Leu Glu Arg Cys Gly Val Ser Asp Val Phe Ala Tyr Pro Gly Gly Ala
                85                  90                  95

Ser Met Glu Ile His Gln Ala Leu Thr Arg Ser Pro Val Ile Thr Asn
                100                 105                 110

His Leu Phe Arg His Glu Gln Gly Glu Ala Phe Ala Ala Ser Gly Tyr
            115                 120                 125

Ala Arg Ala Ser Gly Arg Val Gly Val Cys Val Ala Thr Ser Gly Pro
            130                 135                 140

Gly Ala Thr Asn Leu Val Ser Ala Leu Ala Asp Ala Leu Leu Asp Ser
145                 150                 155                 160

Val Pro Met Val Ala Ile Thr Gly Gln Val Pro Arg Arg Met Ile Gly
                165                 170                 175

Thr Asp Ala Phe Gln Glu Thr Pro Ile Val Glu Val Thr Arg Ser Ile
            180                 185                 190

Thr Lys His Asn Tyr Leu Val Leu Asp Val Glu Asp Ile Pro Arg Val
            195                 200                 205

Ile Gln Glu Ala Phe Phe Leu Ala Ser Ser Gly Arg Pro Gly Pro Val
    210                 215                 220

Leu Val Asp Ile Pro Lys Asp Ile Gln Gln Gln Met Ala Val Pro Val
225                 230                 235                 240

Trp Asp Thr Ser Met Asn Leu Pro Gly Tyr Ile Ala Arg Leu Pro Lys
                245                 250                 255

Pro Pro Ala Thr Glu Leu Leu Glu Gln Val Leu Arg Leu Val Gly Glu
                260                 265                 270

Ser Arg Arg Pro Ile Leu Tyr Val Gly Gly Gly Cys Ser Ala Ser Gly
    275                 280                 285

Asp Glu Leu Arg Trp Phe Val Glu Leu Thr Gly Ile Pro Val Thr Thr
    290                 295                 300

Thr Leu Met Gly Leu Gly Asn Phe Pro Ser Asp Asp Pro Leu Ser Leu
305                 310                 315                 320

Arg Met Leu Gly Met His Gly Thr Val Tyr Ala Asn Tyr Ala Val Asp
            325                 330                 335

Lys Ala Asp Leu Leu Leu Ala Phe Gly Val Arg Phe Asp Asp Arg Val
            340                 345                 350

Thr Gly Lys Ile Glu Ala Phe Ala Ser Arg Ala Lys Ile Val His Ile
        355                 360                 365

Asp Ile Asp Pro Ala Glu Ile Gly Lys Asn Lys Gln Pro His Val Ser
        370                 375                 380

Ile Cys Ala Asp Val Lys Leu Ala Leu Gln Gly Leu Asn Ala Leu Leu
385                 390                 395                 400

Gln Gln Ser Thr Thr Lys Thr Ser Ser Asp Phe Ser Ala Trp His Asn
            405                 410                 415

Glu Leu Asp Gln Gln Lys Arg Glu Phe Pro Leu Gly Tyr Lys Thr Phe
            420                 425                 430
```

-continued

```
Gly Glu Glu Ile Pro Pro Gln Tyr Ala Ile Gln Val Leu Asp Glu Leu
        435                 440                 445

Thr Lys Gly Glu Ala Ile Ile Ala Thr Gly Val Gly Gln His Gln Met
    450                 455                 460

Trp Ala Ala Gln Tyr Tyr Thr Tyr Lys Arg Pro Arg Gln Trp Leu Ser
465                 470                 475                 480

Ser Ala Gly Leu Gly Ala Met Gly Phe Gly Leu Pro Ala Ala Ala Gly
                485                 490                 495

Ala Ser Val Ala Asn Pro Gly Val Thr Val Val Asp Ile Asp Gly Asp
            500                 505                 510

Gly Ser Phe Leu Met Asn Ile Gln Glu Leu Ala Leu Ile Arg Ile Glu
        515                 520                 525

Asn Leu Pro Val Lys Val Met Val Leu Asn Asn Gln His Leu Gly Met
    530                 535                 540

Val Val Gln Trp Glu Asp Arg Phe Tyr Lys Ala Asn Arg Ala His Thr
545                 550                 555                 560

Tyr Leu Gly Asn Pro Glu Cys Glu Ser Glu Ile Tyr Pro Asp Phe Val
                565                 570                 575

Thr Ile Ala Lys Gly Phe Asn Ile Pro Ala Val Arg Val Thr Lys Lys
            580                 585                 590

Ser Glu Val Arg Ala Ala Ile Lys Lys Met Leu Glu Thr Pro Gly Pro
        595                 600                 605

Tyr Leu Leu Asp Ile Ile Val Pro His Gln Glu His Val Leu Pro Met
    610                 615                 620

Ile Pro Ser Gly Gly Ala Phe Lys Asp Met Ile Leu Asp Gly Asp Gly
625                 630                 635                 640

Arg Thr Val Tyr
```